(12) United States Patent
Birk et al.

(10) Patent No.: US 9,532,892 B2
(45) Date of Patent: Jan. 3, 2017

(54) BARIATRIC DEVICE AND METHOD FOR WEIGHT LOSS

(75) Inventors: Janel Birk, Oxnard, CA (US); Daniel Dongelmans, Oxnard, CA (US)

(73) Assignee: Apollo Endosurgery, Inc., Austin, TX (US)

( * ) Notice: Subject to any disclaimer, the term of this patent is extended or adjusted under 35 U.S.C. 154(b) by 1038 days.

(21) Appl. No.: 13/503,273

(22) PCT Filed: Jul. 13, 2010

(86) PCT No.: PCT/US2010/041774
§ 371 (c)(1),
(2), (4) Date: Apr. 20, 2012

(87) PCT Pub. No.: WO2011/049651
PCT Pub. Date: Apr. 28, 2011

(65) Prior Publication Data
US 2012/0221037 A1 Aug. 30, 2012

Related U.S. Application Data

(60) Provisional application No. 61/253,816, filed on Oct. 21, 2009, provisional application No. 61/262,045, filed on Nov. 17, 2009, provisional application No. 61/262,040, filed on Nov. 17, 2009, provisional application No. 61/264,651, filed on Nov. 25, 2009.

(51) Int. Cl.
*A61F 5/00* (2006.01)
*A61F 2/04* (2013.01)

(52) U.S. Cl.
CPC ............. *A61F 5/003* (2013.01); *A61F 5/0003* (2013.01); *A61F 5/0013* (2013.01); *A61F 5/0036* (2013.01); *A61F 5/0079* (2013.01); *A61F 2002/045* (2013.01)

(58) Field of Classification Search
CPC .... A61F 5/0003; A61F 5/0013; A61F 5/0036; A61F 2002/045
USPC ........... 606/191, 151; 604/8, 9, 174; 600/37; 623/23.68, 23.64
See application file for complete search history.

(56) References Cited

U.S. PATENT DOCUMENTS

| | | |
|---|---|---|
| 4,416,267 A | 11/1983 | Garren et al. |
| 4,607,618 A | 8/1986 | Angelchik |
| 4,648,383 A | 3/1987 | Angelchik |
| 4,739,758 A | 4/1988 | Lai et al. |
| 4,774,956 A | 10/1988 | Kruse et al. |

(Continued)

FOREIGN PATENT DOCUMENTS

| | | |
|---|---|---|
| DE | 102007025312 | 11/2008 |
| EP | 1397998 | 3/2004 |

(Continued)

*Primary Examiner* — Melanie Tyson
*Assistant Examiner* — Rachel S Highland
(74) *Attorney, Agent, or Firm* — Gordon & Jacobson, P.C.

(57) ABSTRACT

A bariatric device for use in inducing weight loss, comprising a cardiac element, a pyloric element, and a connecting element between the two other elements, wherein the connecting element provides structure between the cardiac and pyloric elements, keeping them largely in place and at least intermittently touching and applying pressure to the stomach's cardiac, adjacent fundic and pyloric regions, respectively, which produces a satiety signal to the user, giving the recipient a feeling of fullness and reducing his or her hunger feelings.

8 Claims, 46 Drawing Sheets

(56) References Cited

U.S. PATENT DOCUMENTS

| | | | |
|---|---|---|---|
| 4,844,068 A | 7/1989 | Arata et al. |
| 4,899,747 A | 2/1990 | Garren et al. |
| 4,925,446 A | 5/1990 | Garay et al. |
| 5,259,399 A | 11/1993 | Brown |
| 5,312,343 A | 5/1994 | Krog et al. |
| 5,820,584 A | 10/1998 | Crabb |
| 6,264,700 B1 | 7/2001 | Kilcoyne et al. |
| 6,322,538 B1 | 11/2001 | Elbert et al. |
| 6,454,785 B2 | 9/2002 | De Hoyos Garza |
| 6,540,789 B1 | 4/2003 | Silverman et al. |
| 6,579,301 B1 | 6/2003 | Bales et al. |
| 6,675,809 B2 | 1/2004 | Stack et al. |
| 6,733,512 B2 | 5/2004 | McGhan |
| 6,845,776 B2 | 1/2005 | Stack et al. |
| 6,981,978 B2 | 1/2006 | Gannoe |
| 6,981,980 B2 | 1/2006 | Sampson et al. |
| 6,994,095 B2 | 2/2006 | Burnett |
| 7,008,419 B2 | 3/2006 | Shadduck |
| 7,033,384 B2 | 4/2006 | Gannoe et al. |
| 7,037,344 B2 | 5/2006 | Kagan et al. |
| 7,056,305 B2 | 6/2006 | Garza Alvarez |
| 7,090,699 B2 | 8/2006 | Geitz |
| 7,214,233 B2 | 5/2007 | Gannoe et al. |
| 7,220,237 B2 | 5/2007 | Gannoe et al. |
| 7,220,284 B2 | 5/2007 | Kagan et al. |
| 7,223,277 B2 | 5/2007 | DeLegge |
| 7,320,696 B2 | 1/2008 | Gazi et al. |
| 7,347,875 B2 | 3/2008 | Levine et al. |
| 7,354,454 B2 | 4/2008 | Stack et al. |
| 7,476,256 B2 | 1/2009 | Meade et al. |
| 7,510,559 B2 | 3/2009 | Deem et al. |
| 7,608,114 B2 | 10/2009 | Levine et al. |
| 7,682,330 B2 | 3/2010 | Meade et al. |
| 7,695,446 B2 | 4/2010 | Levine et al. |
| 7,699,863 B2 | 4/2010 | Marco et al. |
| 7,753,870 B2 | 7/2010 | Demarais et al. |
| 7,771,382 B2 | 8/2010 | Levine et al. |
| 7,794,447 B2 | 9/2010 | Dann et al. |
| 7,815,589 B2 | 10/2010 | Meade et al. |
| 7,837,643 B2 | 11/2010 | Levine et al. |
| 7,841,503 B2 | 11/2010 | Sonnenschein et al. |
| 7,931,693 B2 | 4/2011 | Binmoeller |
| 7,981,162 B2 | 7/2011 | Stack et al. |
| 8,029,455 B2 | 10/2011 | Stack et al. |
| 8,032,223 B2 | 10/2011 | Imran |
| 2003/0109935 A1 | 6/2003 | Geitz |
| 2003/0153905 A1 | 8/2003 | Edwards et al. |
| 2004/0044357 A1 | 3/2004 | Gannoe et al. |
| 2004/0092892 A1 | 5/2004 | Kagan et al. |
| 2004/0117031 A1 | 6/2004 | Stack et al. |
| 2004/0122452 A1 | 6/2004 | Deem et al. |
| 2004/0122453 A1 | 6/2004 | Deem et al. |
| 2004/0243152 A1* | 12/2004 | Taylor ................ A61F 5/0079 606/151 |
| 2005/0049718 A1 | 3/2005 | Dann et al. |
| 2005/0055039 A1 | 3/2005 | Burnett et al. |
| 2005/0085923 A1 | 4/2005 | Levine et al. |
| 2005/0096692 A1 | 5/2005 | Linder et al. |
| 2005/0192614 A1 | 9/2005 | Binmoeller |
| 2005/0197714 A1 | 9/2005 | Sayet |
| 2005/0228504 A1* | 10/2005 | Demarais ................ 623/23.65 |
| 2005/0267595 A1 | 12/2005 | Chen et al. |
| 2005/0267596 A1 | 12/2005 | Chen et al. |
| 2005/0273060 A1 | 12/2005 | Levy et al. |
| 2006/0178691 A1 | 8/2006 | Binmoeller |
| 2006/0252983 A1 | 11/2006 | Lembo et al. |
| 2007/0010864 A1 | 1/2007 | Dann et al. |
| 2007/0016262 A1 | 1/2007 | Gross et al. |
| 2007/0021761 A1 | 1/2007 | Phillips |
| 2007/0078476 A1 | 4/2007 | Hull, Sr. et al. |
| 2007/0083224 A1 | 4/2007 | Hively |
| 2007/0100368 A1 | 5/2007 | Quijano et al. |
| 2007/0118168 A1 | 5/2007 | Lointier et al. |
| 2007/0156013 A1 | 7/2007 | Birk |
| 2007/0173881 A1 | 7/2007 | Birk et al. |
| 2007/0185374 A1 | 8/2007 | Kick et al. |
| 2007/0239284 A1 | 10/2007 | Skerven et al. |
| 2007/0265598 A1 | 11/2007 | Karasik |
| 2007/0293716 A1 | 12/2007 | Baker et al. |
| 2008/0015618 A1 | 1/2008 | Sonnenschein et al. |
| 2008/0058840 A1 | 3/2008 | Albrecht et al. |
| 2008/0058887 A1 | 3/2008 | Griffin et al. |
| 2008/0097513 A1 | 4/2008 | Kaji et al. |
| 2008/0208241 A1 | 8/2008 | Weiner et al. |
| 2008/0221595 A1 | 9/2008 | Surti |
| 2008/0234718 A1 | 9/2008 | Paganon et al. |
| 2008/0234834 A1 | 9/2008 | Meade et al. |
| 2008/0243166 A1 | 10/2008 | Paganon et al. |
| 2008/0249635 A1 | 10/2008 | Weitzner et al. |
| 2008/0255678 A1 | 10/2008 | Cully et al. |
| 2008/0262529 A1 | 10/2008 | Jacques |
| 2009/0012553 A1 | 1/2009 | Swain et al. |
| 2009/0082644 A1 | 3/2009 | Li |
| 2009/0093767 A1 | 4/2009 | Kelleher |
| 2009/0149879 A1 | 6/2009 | Dillon |
| 2009/0198210 A1 | 8/2009 | Burnett et al. |
| 2009/0259246 A1 | 10/2009 | Eskaros et al. |
| 2009/0275973 A1 | 11/2009 | Chen et al. |
| 2009/0287231 A1 | 11/2009 | Brooks et al. |
| 2009/0299486 A1 | 12/2009 | Shohat et al. |
| 2009/0312597 A1 | 12/2009 | Bar et al. |
| 2010/0030017 A1 | 2/2010 | Baker et al. |
| 2010/0049224 A1 | 2/2010 | Vargas |
| 2010/0100115 A1 | 4/2010 | Soetermans et al. |
| 2010/0121371 A1 | 5/2010 | Brooks et al. |
| 2010/0168782 A1 | 7/2010 | Hancock |
| 2010/0249822 A1 | 9/2010 | Nihalani |
| 2010/0256775 A1 | 10/2010 | Belhe et al. |
| 2010/0256776 A1 | 10/2010 | Levine et al. |
| 2010/0305590 A1 | 12/2010 | Holmes et al. |
| 2010/0331756 A1 | 12/2010 | Meade et al. |

FOREIGN PATENT DOCUMENTS

| | | |
|---|---|---|
| EP | 1774929 | 4/2007 |
| FR | 2892297 | 4/2007 |
| FR | 2941617 | 8/2010 |
| WO | WO8800027 | 1/1988 |
| WO | WO0032092 | 6/2000 |
| WO | WO2005094257 | 10/2005 |
| WO | WO2005097012 | 10/2005 |
| WO | WO2005110280 | 11/2005 |
| WO | WO2006044640 | 4/2006 |
| WO | WO2006111961 | 10/2006 |
| WO | WO2006118744 | 11/2006 |
| WO | WO2007027812 | 3/2007 |
| WO | WO2007053556 | 5/2007 |
| WO | WO2007076021 | 7/2007 |
| WO | WO2007092390 | 8/2007 |
| WO | WO2007110866 | 10/2007 |
| WO | WO2008101048 | 8/2008 |
| WO | WO2008112894 | 9/2008 |
| WO | WO2008132745 | 11/2008 |
| WO | WO2010042062 | 4/2010 |
| WO | WO2010047712 | 7/2010 |
| WO | WO2010087757 | 8/2010 |
| WO | WO2010117641 | 10/2010 |

\* cited by examiner

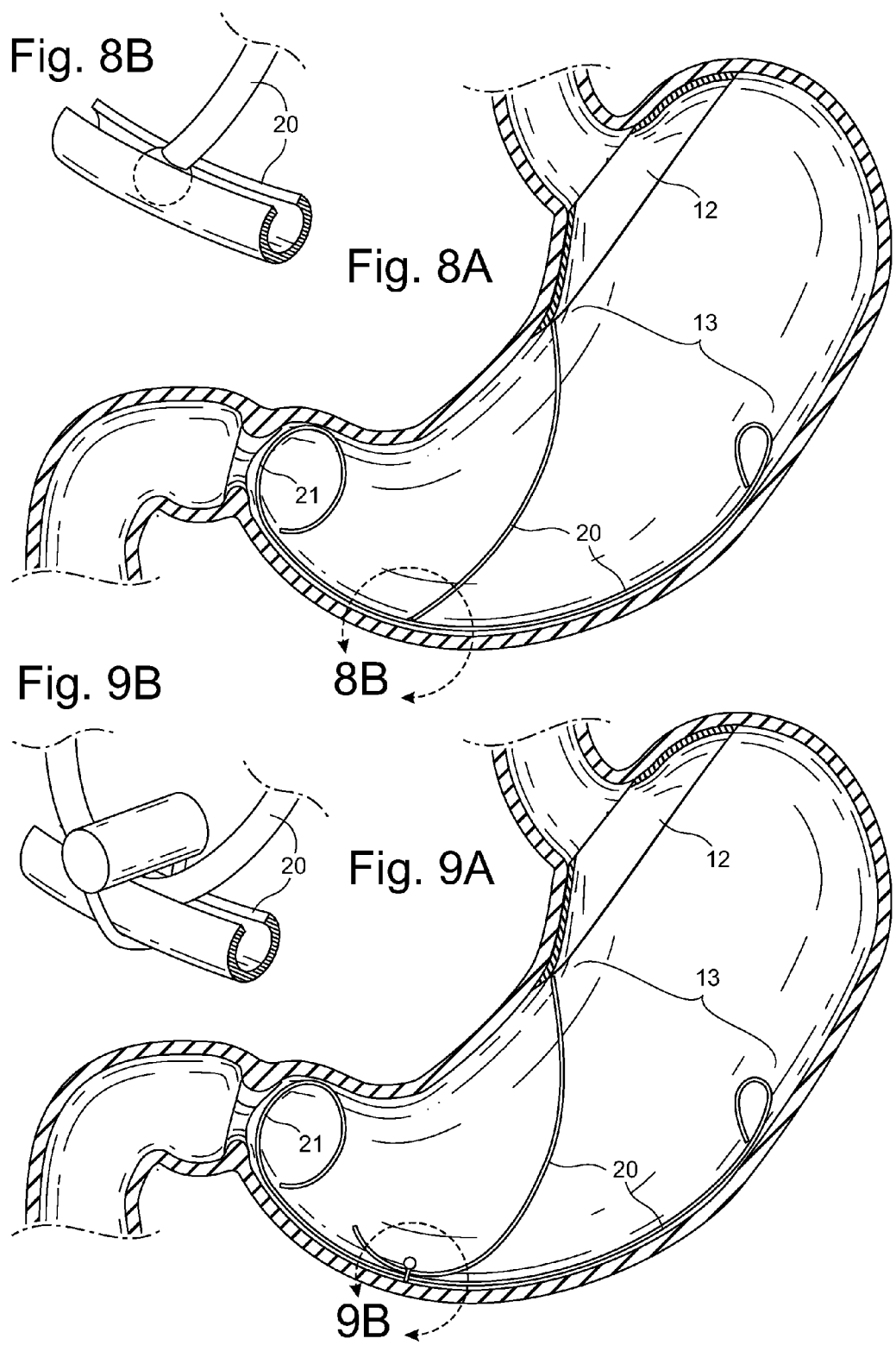

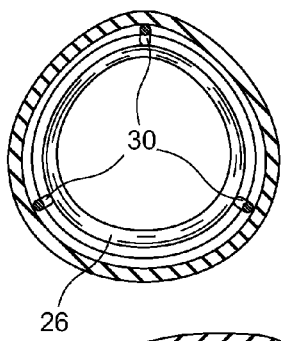
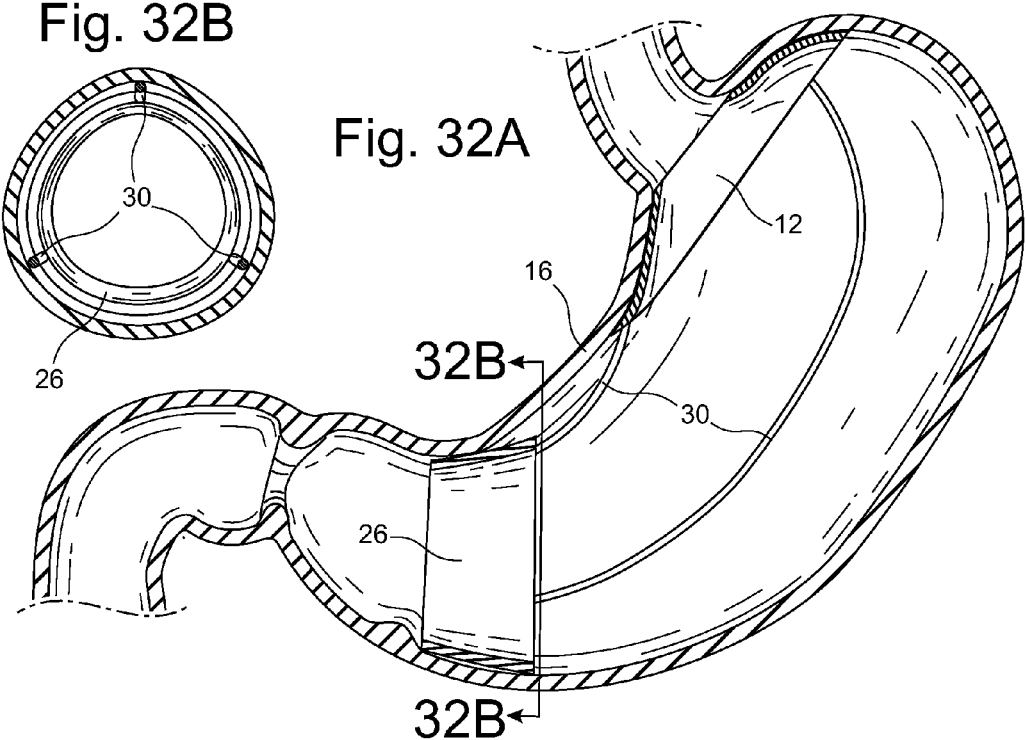
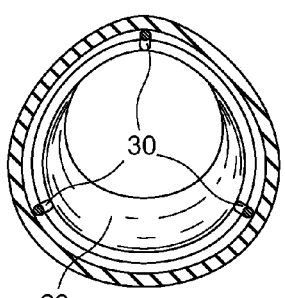
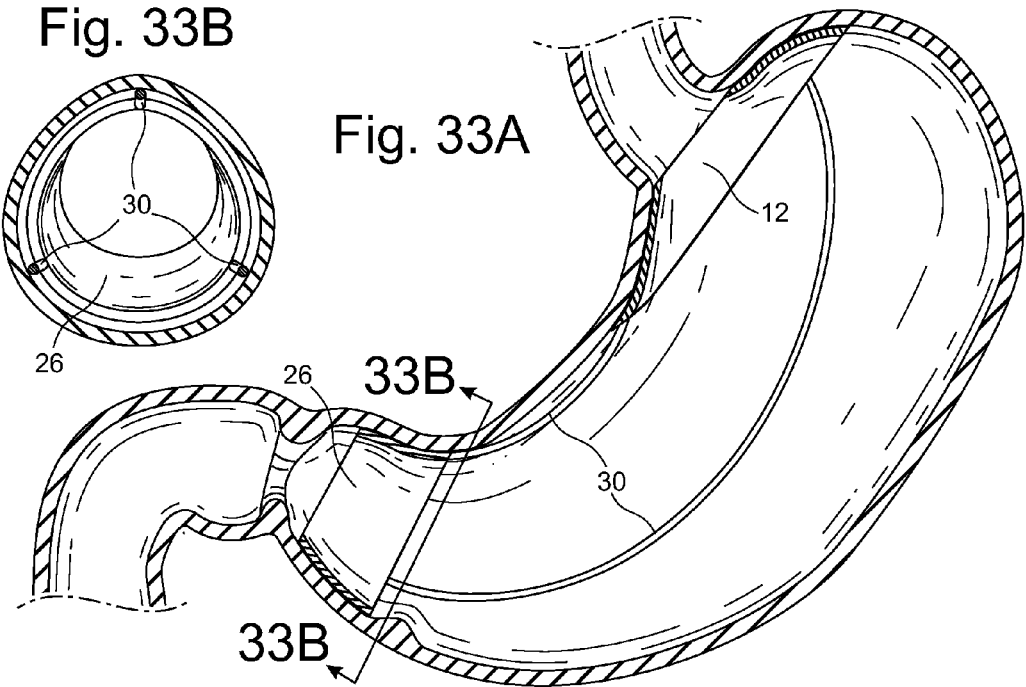

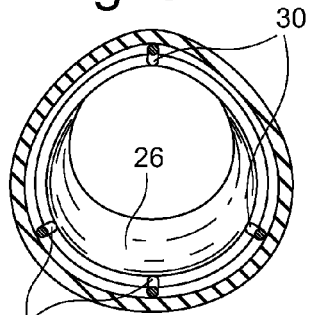
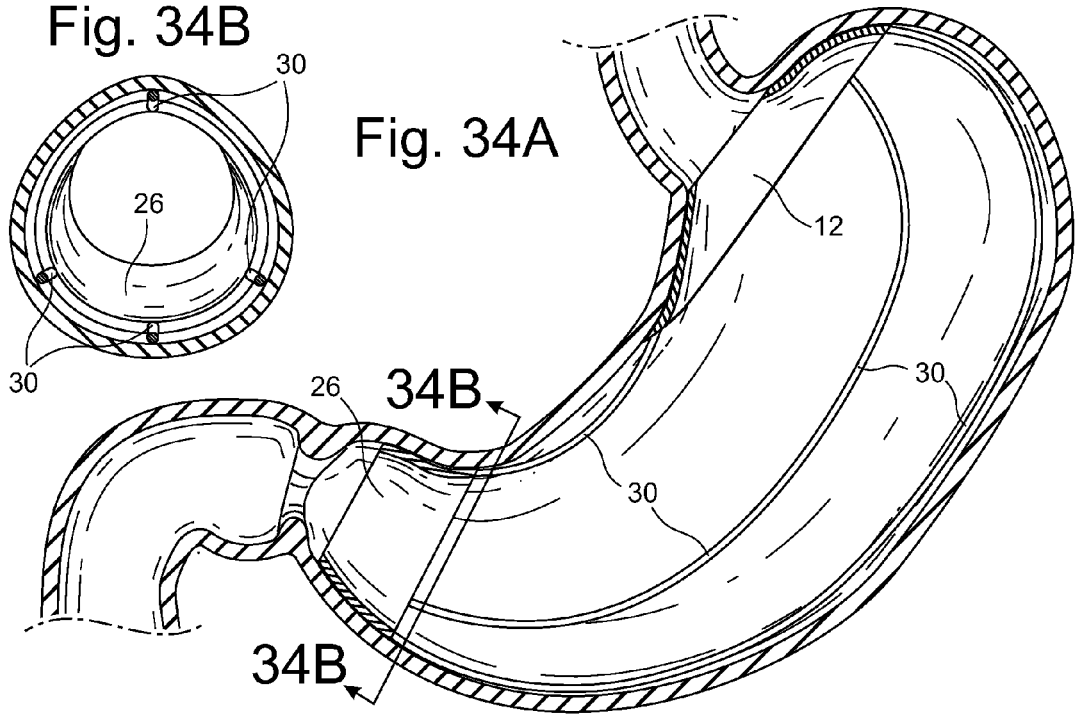
Fig. 34B
Fig. 34A
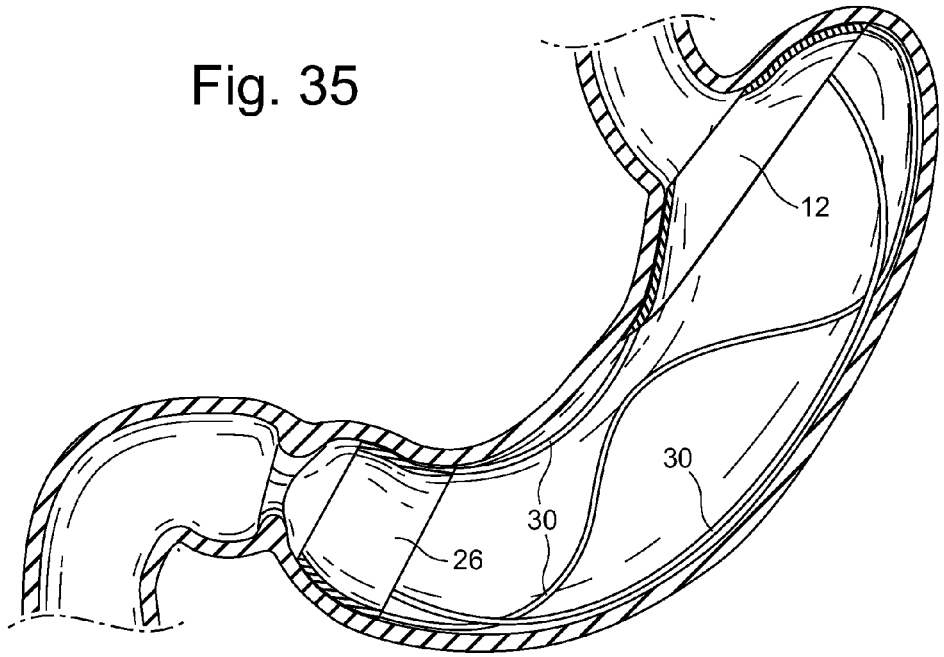
Fig. 35

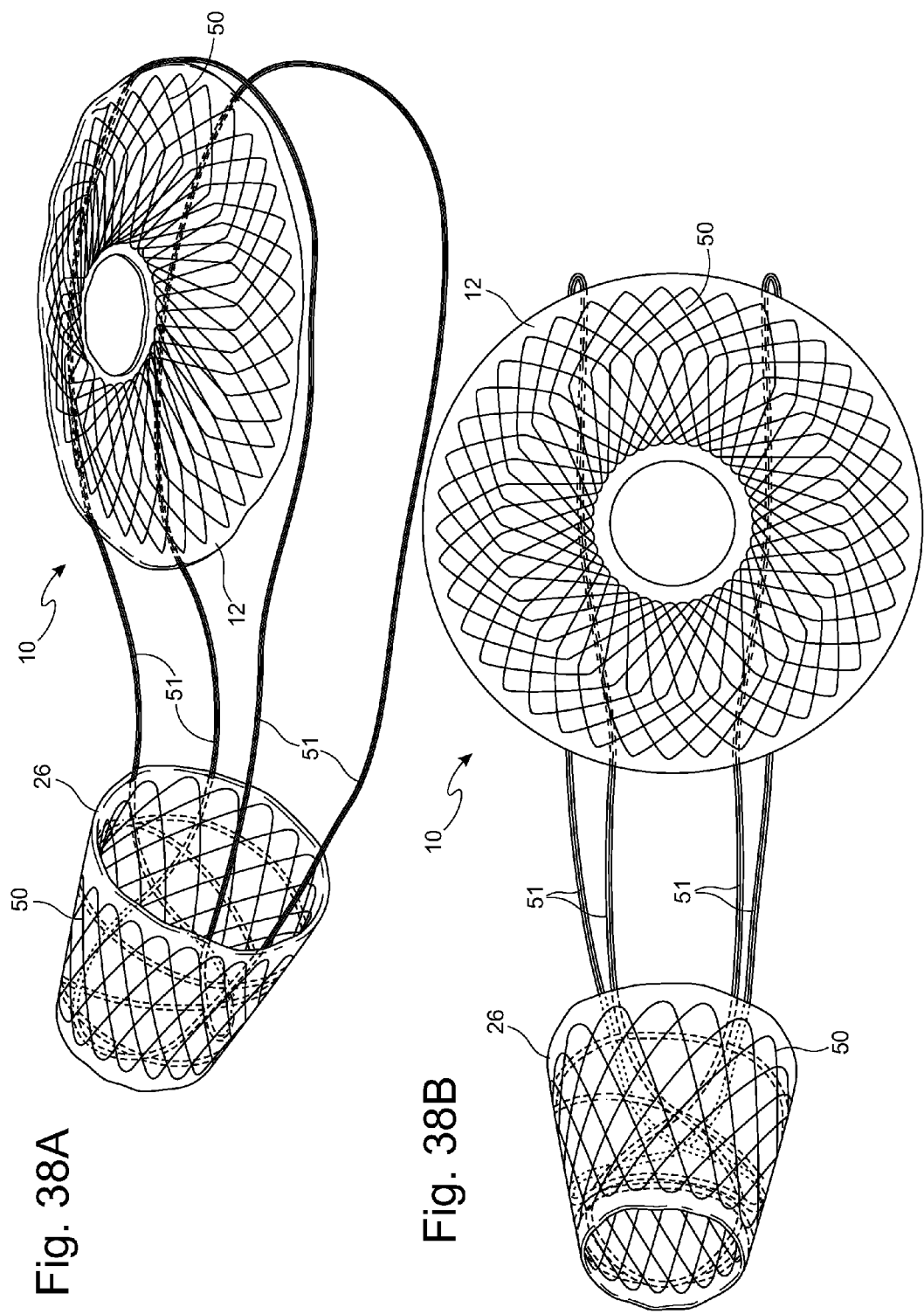

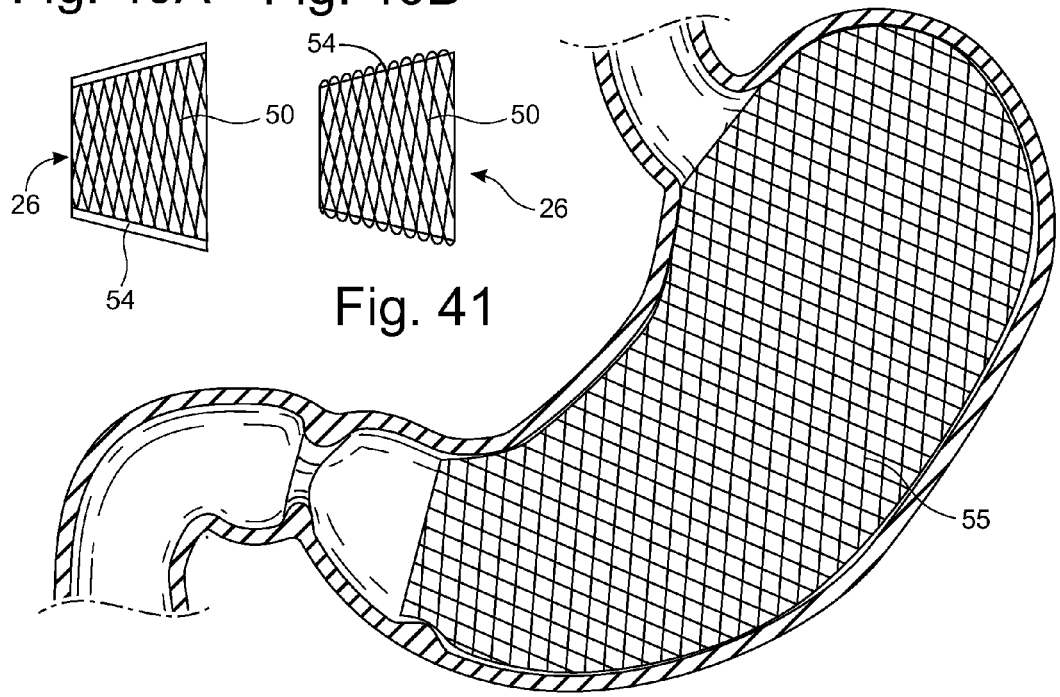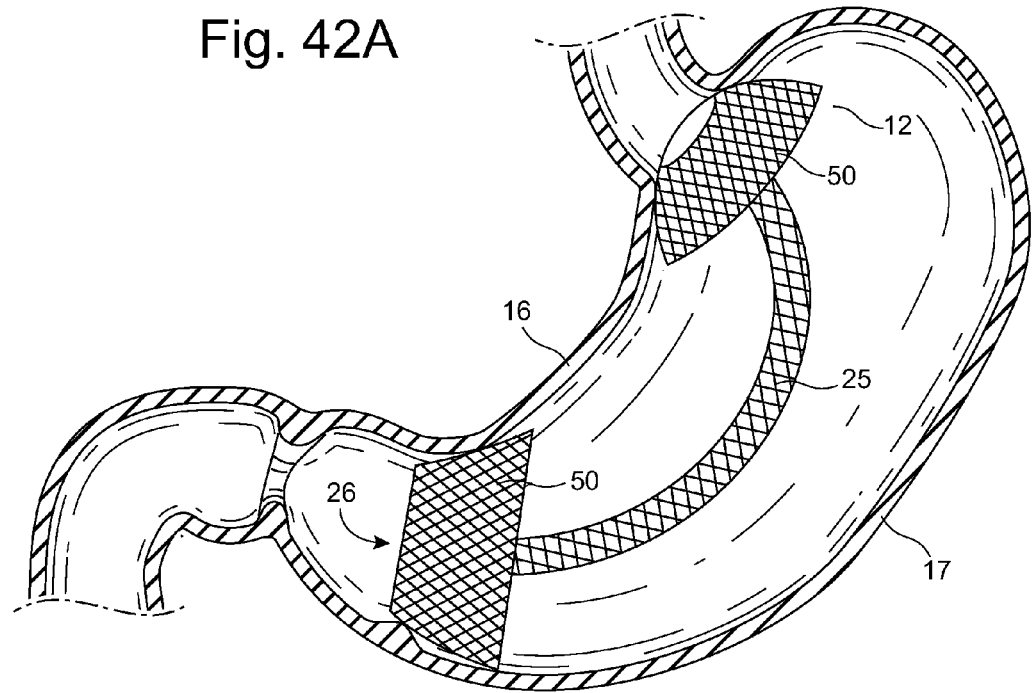

Fig. 47A
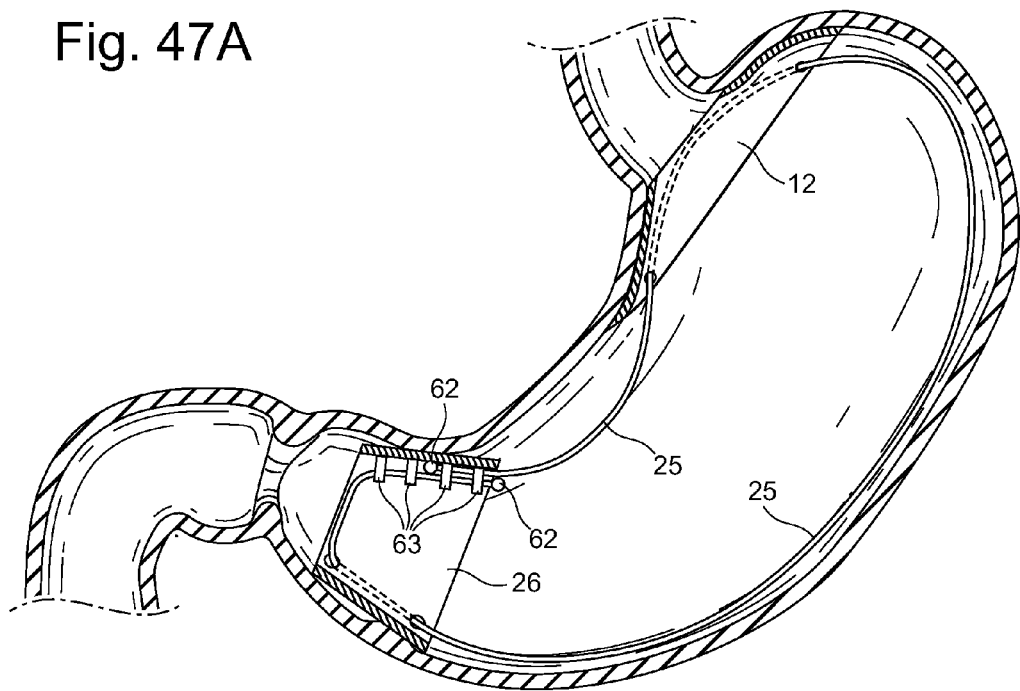
Fig. 47B
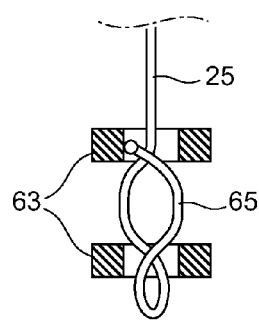
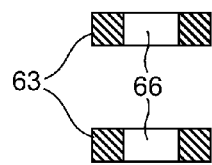
Fig. 47C
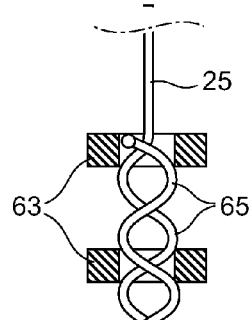
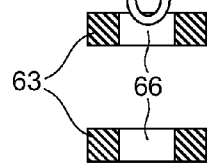
Fig. 47D
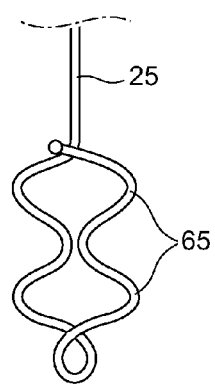

Fig. 54
Fig. 53
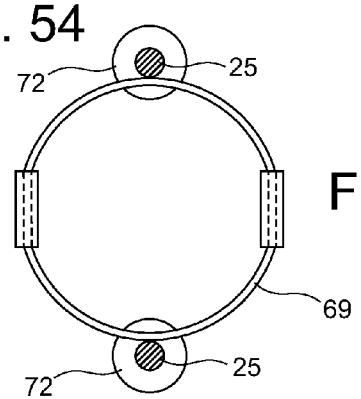
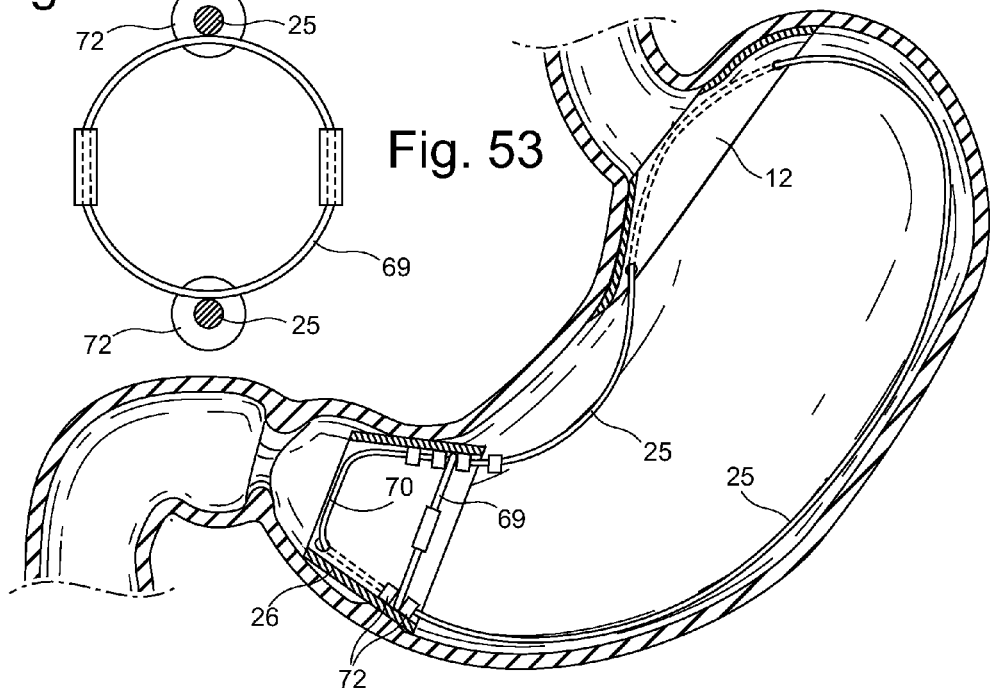
Fig. 55
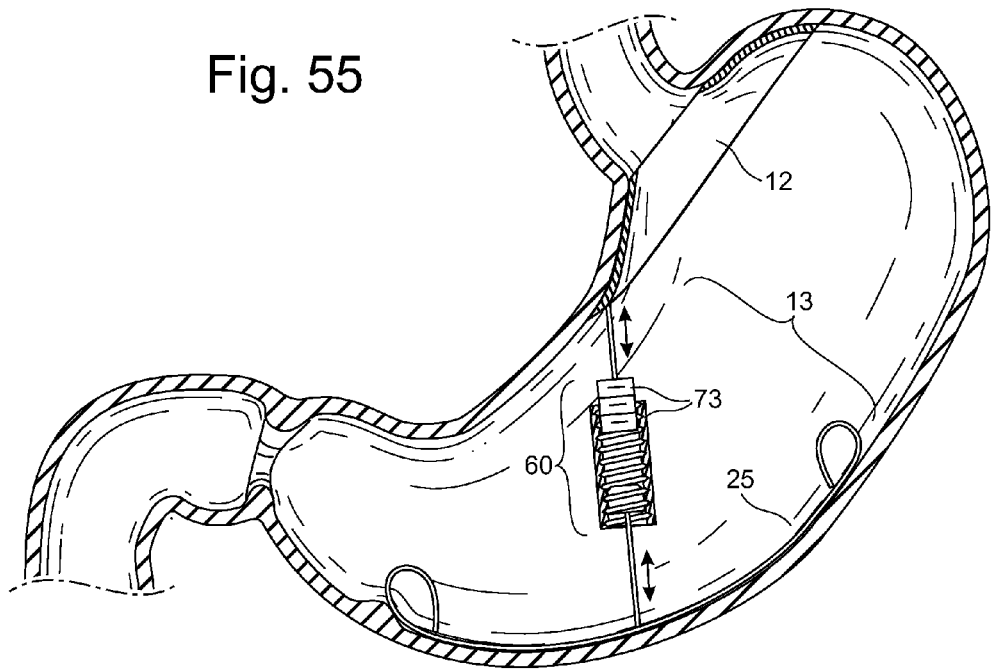

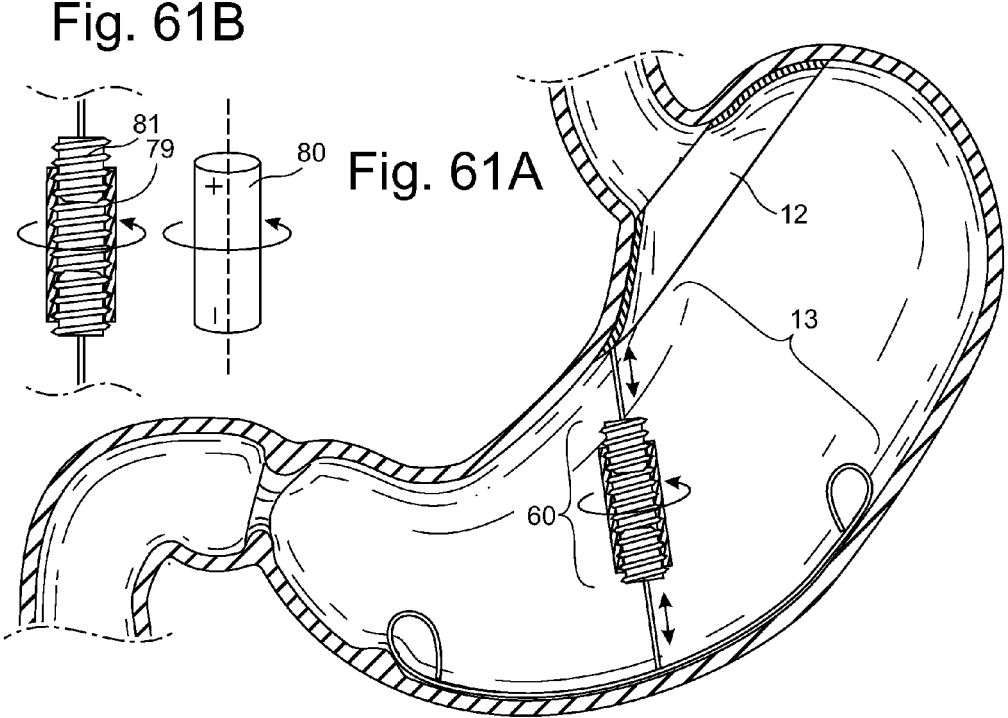
Fig. 61B
Fig. 61A
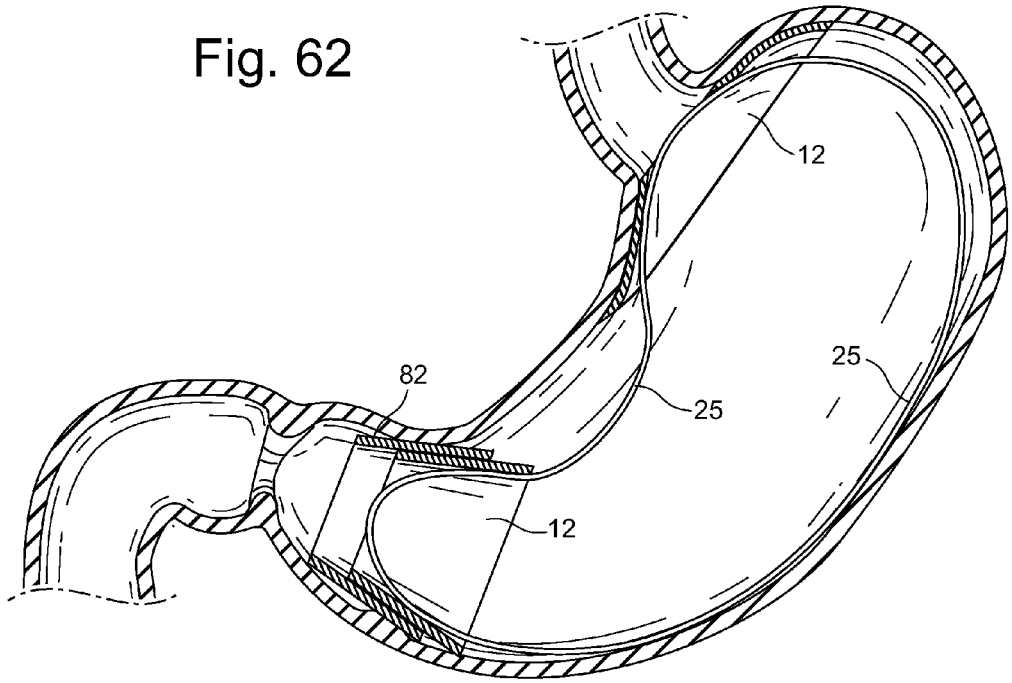
Fig. 62

Fig. 66
Fig. 67
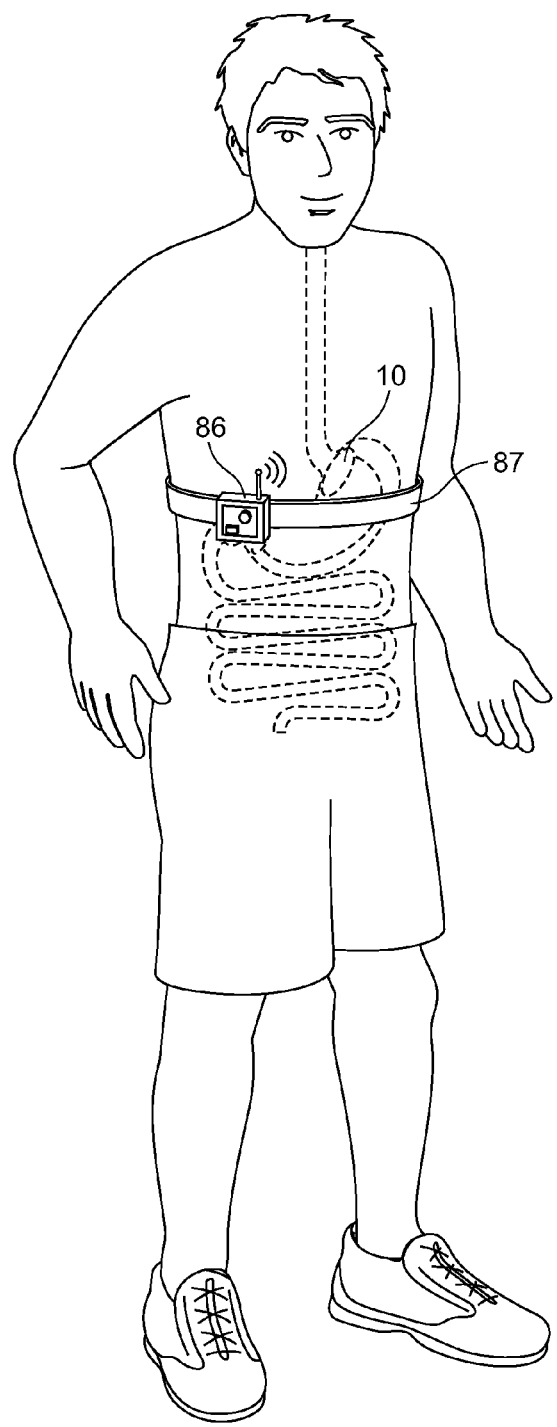
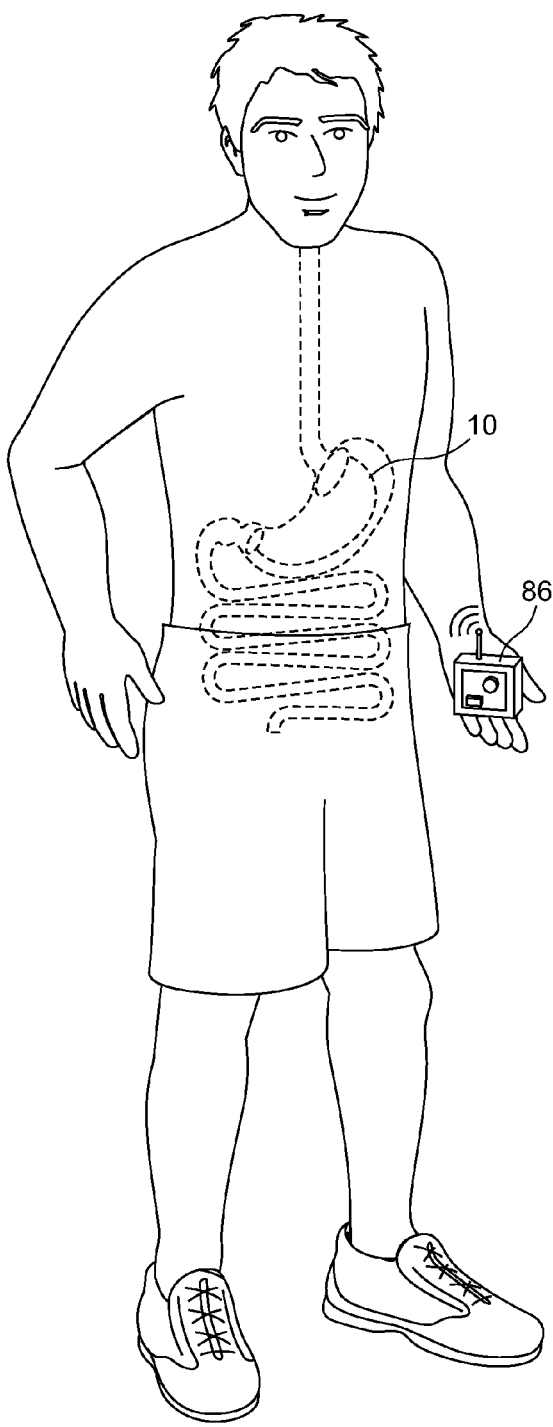

Fig. 78
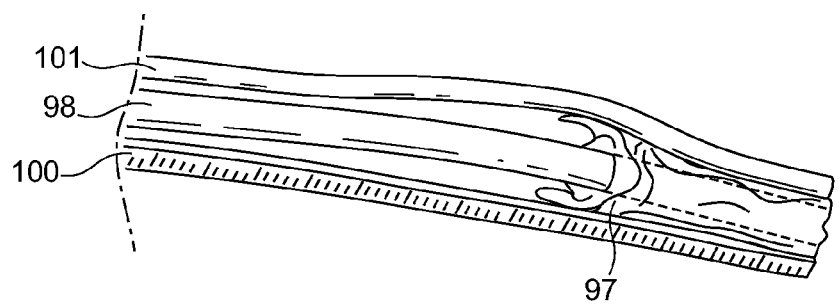
Fig. 79
Fig. 80
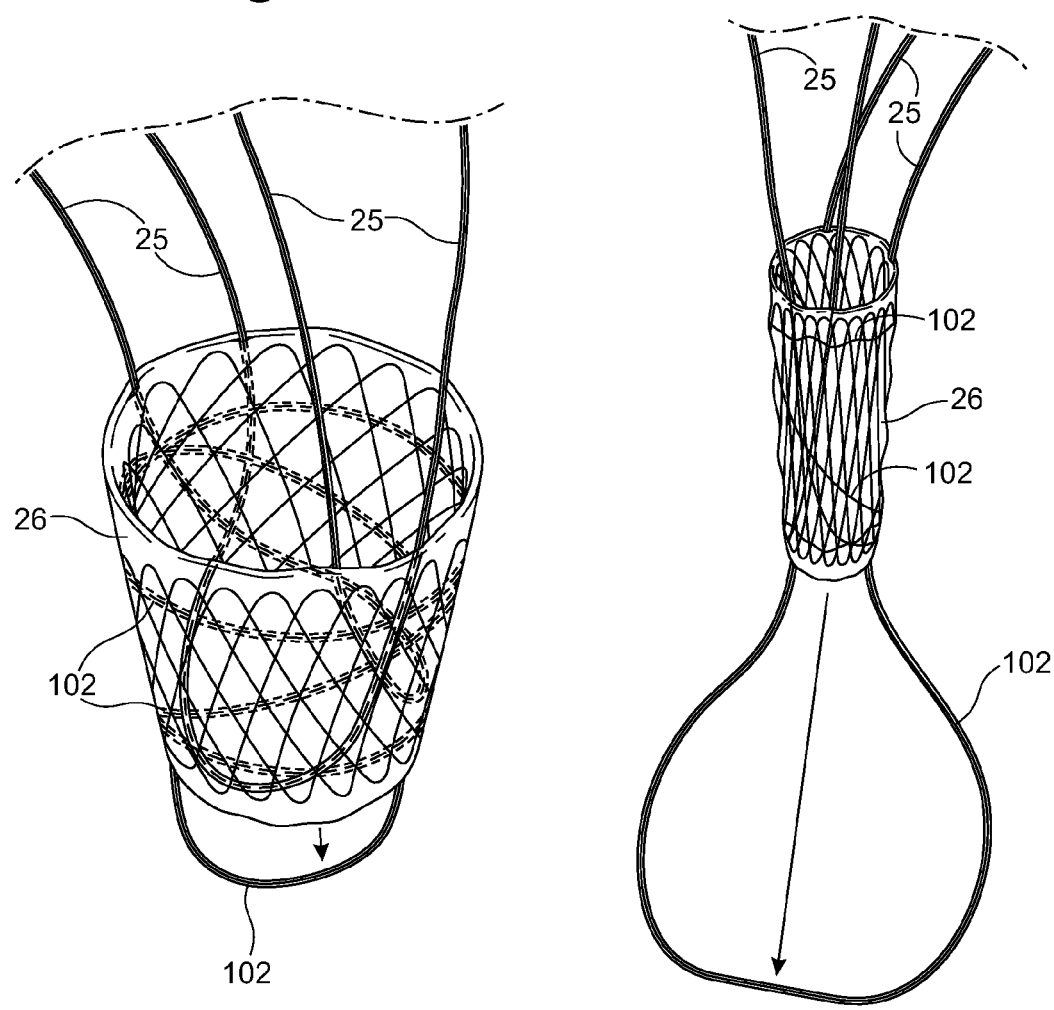

BARIATRIC DEVICE AND METHOD FOR WEIGHT LOSS

RELATED APPLICATION

This application is a national stage application under 35 USC §371 of PCT Patent Application No. PCT/US2010/041774, filed Jul. 13, 2010, which claims the benefit of U.S. Provisional Application No. 61/253,816, filed Oct. 21, 2009, U.S. Provisional Application No. 61/262,040, filed Nov. 17, 2009, U.S. Provisional Application No. 61/262,045, filed Nov. 17, 2009, and U.S. Provisional Application No. 61/264,651, filed Nov. 25, 2009.

TECHNICAL FIELD

This invention relates to a bariatric device for weight loss, and ancillary items such as sizing, deployment, and removal apparatus.

BACKGROUND

Obesity has been steadily increasing worldwide and poses serious health risks, which if untreated, can become life threatening. There are various methods for reducing weight such as diet, exercise, and medications but often the weight loss is not sustained. Significant advances have been made in the surgical treatment of obesity. Surgical procedures such as the gastric bypass and gastric banding have produced substantial and lasting weight loss for obese patients. These procedures and products have been shown to significantly reduce health risks over time, and are currently the gold standard for bariatric treatment.

Although surgical intervention has been shown to be successful at managing weight loss, both procedures are invasive and carry the risks of surgery. Gastric bypass is a highly invasive procedure which creates a small pouch by segmenting and/or removing a large portion of the stomach and rerouting the intestines permanently. Gastric bypass and its variations have known complications. Gastric banding is an invasive procedure which creates a small pouch in the upper stomach by wrapping a band around the stomach to segment it from the lower stomach. Although the procedure is reversible, it also carries known complications.

Less invasive or non-invasive devices that are removable and capable of significant weight loss are desirable.

SUMMARY

The bariatric device described herein induces weight loss by engaging the upper and lower regions of the stomach. One embodiment of the bariatric device disclosed herein is based on applying force or pressure on or around the cardiac opening or gastroesophogeal (GE) junction and upper stomach. It may also include pressure in the lower esophagus. The device can be straightened or compressed to allow for introduction down the esophagus and then change into the desired shape inside the stomach. This device may not require any sutures or fixation and would orient inside the stomach based on the device's geometry. The device may be constructed of 2 main elements:

1) A cardiac element that contacts or intermittently contacts the upper stomach around the GE junction and may also contact the lower esophagus.

2) A positioning element that maintains the position of the first element in the stomach.

One of the purposes of the cardiac element which contacts the upper stomach or cardia is to at least intermittently apply direct force or pressure to this region of the stomach. Applying force or pressure to this region of the stomach replicates the forces and pressures that are generated during eating and swallowing. It also engages or stimulates the stretch receptors that are present in this region of the stomach. During eating, as the stomach fills, peristalsis starts and generates higher pressures in the stomach for digestion, which activates the stretch receptors to induce a satiety response, and may also trigger a neurohormonal response to cause satiety or weight loss. The cardiac element replicates this type of pressure on the stretch receptors. The cardiac element could take the form of many different shapes such as a ring, a cone, a frusto-cone, a sphere, an oval, an ovoid, a pyramid, an open or closed polyhedron, a square, a spiral, a kidney shape, multiple protuberances, multiple spheres or multiples of any shape or other structure. It could also be an inflatable balloon or contain an inflatable balloon. This balloon could be spherical, or it could be a torus or a sphere with channels on the side to allow food to pass, or it could be a cone or other. For the purpose of the claims of this patent, the "upper stomach" includes the cardiac region (a band of tissue in the stomach that surrounds the gastroesophogeal (GE) junction), and the fundus adjacent to the cardiac region, and may be either of these two areas, or both.

Some of the purposes of the positioning element are to provide structure for the device to maintain its relative placement location, provide support for the cardiac element to apply constant, intermittent, or indirect pressure against the upper stomach, and to prevent the device from migrating into the duodenum or small intestine. The positioning element may also be constructed in such a manner as to impart an outwardly biasing force between the stomach and the cardiac element, so that the cardiac element can maintain at least intermittent pressure against the upper stomach, including the cardiac region and the adjacent portion of the fundus. This positioning element would be preferentially in the stomach above the pyloric valve. The positioning element could also take the form of a wire, a taper, a tube, a ribbon, a spiral of a single diameter, a spiral of varying diameter, an I-beam, or other suitable shapes. Similarly, the positioning element could comprise multiple members to improve its structural integrity. The positioning element could be generally curved to match the greater curve or lesser curve of the stomach, or both, or could be straight, or a combination of any of the above. Similar to the cardiac element, the positioning element could also take several different shapes, such as a ring, a cone, a sphere, an oval, a kidney shape, a pyramid, a square, a spiral, multiple protuberances, multiple spheres or multiples of any shape or other. It could also be an inflatable balloon or contain an inflatable balloon. This balloon could be spherical, or it could be a torus or a sphere with channels on the side to allow food to pass, or it could be a cone, a portion of a cone or other shape. The positioning element could be a combination of a curved wire and a balloon or any combination of the above mentioned forms. The form and structure of the cardiac and positioning elements may vary to adapt appropriately for their purpose. The positioning element may activate stretch receptors or a neurohormonal response to induce satiety or another mechanism of weight loss by contacting or stretching certain portions of the stomach, to induce satiety, delayed gastric emptying or another mechanism of weight loss.

After eating or drinking, the stomach goes through peristalsis to grind up the consumed food, and to propel the contents through the pyloric valve into the duodenum.

Peristalsis causes the stomach to constantly change shape, length and diameter. Due to this constant motion, it is anticipated that this embodiment will move within the stomach. The positioning element may slide back and forth along the greater curve, the lesser curve or along the side walls of the stomach. The positioning element may intermittently engage the lower stomach or pyloric valve, but be of a large enough size to prevent passage through the valve into the duodenum. The positioning element may include elements that are compressible to allow them to pass from a larger portion of the stomach into a smaller portion of the stomach such as from the body into the pyloric region, while exerting pressure or intermittent pressure on the cardiac element. Alternatively, the positioning element could have limited compressibility to maintain its position within the stomach.

In another embodiment of the bariatric device disclosed herein, the device may be constructed of three main elements:

1) A cardiac element that engages the upper stomach around the GE junction including the cardiac region and adjacent fundus and may include the lower esophagus.

2) A pyloric element that engages the pyloric region which includes the pyloric antrum or lower stomach.

3) A connecting element that connects the cardiac and pyloric elements.

One of the purposes of the cardiac element which contacts the upper stomach or cardiac region would be to apply at least intermittent pressure or force to engage a satiety response and/or cause a neurohormonal response to cause a reduction in weight. This element could take the form of many different shapes such as a ring, a cone, frusto-cone, a sphere, an oval, a pyramid, a square, a spiral, multiple protuberances, multiple spheres or multiples of any shape or other suitable shapes. It could also be an inflatable balloon or contain an inflatable balloon. This balloon could be spherical, or it could be a torus or a sphere with channels on the side to allow food to pass, or it could be a cone, a portion of a cone or other shapes. The cardiac element may be in constant or intermittent contact with the upper stomach based on the device moving in the stomach during peristalsis.

Some of the purposes of the pyloric element are to engage the pyloric region or lower stomach, and to act in conjunction with the connecting element to provide support for the cardiac element to apply constant, intermittent, or indirect pressure against the upper stomach and or GE junction and lower esophagus. It is also to prevent the device from migrating into the duodenum or small intestine. This pyloric element would be preferentially placed at or above the pyloric valve and could be in constant or intermittent contact with the pyloric region based on movement of the stomach. Depending on the size relative to the stomach, this element may apply radial force, or contact force or pressure to the lower stomach which may also cause a satiety or neurohormonal response. Due to peristalsis of the stomach, the bariatric device may toggle back and forth in the stomach which may cause intermittent contact with the upper and lower stomach regions. The device may also have features to accommodate for the motion to allow for constant contact with the upper and lower regions. Similar to the cardiac element, the pyloric element could take several different shapes such as a ring, a cone, a frusto-cone, a sphere, an oval, a pyramid, a square, a spiral, multiple protuberances, multiple spheres or multiples of any shape or other. It could also be an inflatable balloon. This balloon could be spherical, or it could be a torus or a sphere with channels on the side to allow food to pass, or it could be a cone, a portion of a cone or other shape. This element may activate stretch receptors or a neurohormonal response to induce satiety or another mechanism of weight loss by contacting or stretching certain portions of the stomach, to induce satiety, delayed gastric emptying or another mechanism of weight loss. The form and structure of the cardiac and pyloric elements may vary to adapt appropriately for their purpose. For example, the cardiac element may be a ring while the pyloric element may be a cone or frusto-cone.

Some of the purposes of the connecting element are to connect the cardiac and pyloric elements, to provide structure for the device to maintain its relative placement location, and to provide tension, pressure, or an outwardly biasing force between the pyloric and cardiac elements. The connecting element could take several different forms such as a long curved wire, a curved cylinder of varying diameters, a spiral of a single diameter, a spiral of varying diameter, a ribbon, an I-beam, a tube, a taper, a loop, a curved loop or other. Similarly, the connecting element could comprise multiple members to improve its structural integrity and positioning within the stomach. The connecting element could be generally curved to match the greater curve or lesser curve of the stomach, both, or could be straight, or a combination of any of the above. The connecting element could also be an inflatable balloon or incorporate an inflatable balloon.

The connecting and/or positioning elements 25, 13 could also be self-expanding or incorporate a portion that is self expanding. Self expansion would allow the element or a portion of the element to be compressible, but also allow it to expand back into its original shape to maintain its function and position within the stomach, as well as the function and position of the other element(s). Self expansion would allow the elements to compress for placement down the esophagus, and then expand its original shape in the stomach. This will also allow the element to accommodate peristalsis once the device is in the stomach. This self-expansion construction of the connecting and positioning elements may impart an outwardly biasing force on the cardiac element, the pyloric element, or both.

In any of the embodiments disclosed herein, the device may be straightened or collapsed for insertion down the esophagus, and then reformed to the desired shape in the stomach to apply pressure at the upper and lower stomach regions or other regions as described above. At least a portion of the device could be made of a shape memory alloys such as Nitinol (nickel titanium), low density polyethylene or polymers to allow for it to compress or flex and then rebound into shape in the stomach. For placement of the device into the stomach, a flexible polymer tube, such as a large diameter overtube, could be placed down the esophagus to protect the esophagus and stomach. The device could then be straightened and placed into the tube for delivery into the stomach, and then would regain its proper shape in the stomach once it exits the tube. Another variation for placement would be a custom delivery catheter to compress the device during placement and then allow the device to deploy out of the catheter once in the stomach.

The bariatric device could be made of many different materials. Elements of the device could be made with materials with spring properties that have adequate strength to hold their shape after reforming, and/or impart an outwardly biasing force. The materials would also need to be acid resistant to withstand the acidic environment of the stomach. Elements of the device could be made of Nitinol, shape memory plastics, shape memory gels, stainless steel, titanium, silicone, elastomers, teflons, polyurethanes, polynorborenes, styrene butadiene co-polymers, cross-linked polyethylenes, cross-linked polycyclooctenes, polyethers, polyacrylates, polyamides, polysiloxanes, polyether amides, polyether esters, and urethane-butadiene co-polymers, other polymers, or combinations of the above, or other suitable materials. For good distribution of stress to the stomach wall or to reduce contact friction, the device could be coated with another material or could be placed into a sleeve of acid resistant materials such as teflons, PTFE, ePTFE, FEP, silicone, elastomers or other polymers. This would allow for a small wire to be cased in a thicker sleeve of acid resistant materials to allow for a better distribution of force across a larger surface area.

The device could take many forms after it reshapes.

BRIEF DESCRIPTION OF DRAWINGS

FIG. 8A depicts a side view of a side view of an embodiment the bariatric device of the present invention having a positioning element, located within a cross-section of a stomach.

FIG. 8B depicts a perspective view of a closeup of part of the positioning element shown in FIG. 8A.

FIG. 9A depicts a side view of a side view of an embodiment the bariatric device of the present invention having a positioning element, located within a cross-section of a stomach.

FIG. 9B depicts a perspective view of a closeup of part of the positioning element shown in FIG. 9A.

FIG. 32A depicts a side view of an embodiment of the bariatric device of the present invention, located within a cross-section of a stomach.

FIG. 32B depicts an internal end view of a pyloric element of an embodiment of the bariatric device of the present invention, located within a cross-section of a stomach shown in FIG. 32A.

FIG. 33A depicts a side view of an embodiment of the bariatric device of the present invention, located within a cross-section of a stomach.

FIG. 33B depicts an internal end view of a pyloric element of an embodiment of the bariatric device of the present invention, located within a cross-section of a stomach shown in FIG. 33A.

FIG. 34A depicts a side view of an embodiment of the bariatric device of the present invention, located within a cross-section of a stomach.

FIG. 34B depicts an internal end view of a pyloric element of an embodiment of the bariatric device of the present invention, located within a cross-section of a stomach shown in FIG. 34A.

FIG. 35 depicts a side view of the embodiment of the present invention shown in FIG. 34A, located within a cross-section of a stomach that is undergoing contraction due to peristalsis.

FIG. 38A depicts an underside perspective view of an embodiment of the bariatric device of the present invention of the present invention.

FIG. 38B depicts a top view of an embodiment of the bariatric device of the present invention of the present invention.

FIG. 40A depicts a side view of a pyloric element of an embodiment of the present invention.

FIG. 40B depicts a side view of a pyloric element of an embodiment of the present invention.

FIG. 41 depicts a side view of an embodiment of the bariatric device of the present invention, located within a cross-section of a stomach.

FIG. 42A depicts a side view of an embodiment of the bariatric device of the present invention, located within a cross-section of a stomach.

FIG. 47A depicts a side view of an embodiment of the bariatric device of the present invention, located within a cross-section of a stomach.

FIG. 47B depicts a side view of a retainer strap and clip adjustment mechanism of an embodiment of the present invention.

FIG. 47C depicts a side view of a retainer strap and clip adjustment mechanism of an embodiment of the present invention.

FIG. 47D depicts a side view of a retainer strap and clip adjustment mechanism of an embodiment of the present invention.

FIG. 53 depicts a side view of an embodiment of the present invention having an adjustment mechanism in the pyloric element, located within a cross-section of a stomach.

FIG. 54 depicts an end view of the adjustment mechanism in the pyloric element of the embodiment shown in FIG. 53.

FIG. 55 depicts a side view of an embodiment of the bariatric device of the present invention, located within a cross-section of a stomach.

FIG. 61A depicts a side view of an embodiment of the present invention, with a magnetic adjustment mechanism in cross section view, located within a cross-section of a stomach.

FIG. 61B depicts a closeup cross-section view of the magnetic adjustment mechanism shown in FIG. 61A, next to a controller magnet.

FIG. 62 depicts a side view of an embodiment of the present invention, equipped with adjustment cones in the pyloric element shown in cross section, located within a cross-section of a stomach.

FIG. 66 depicts a remote controller of an embodiment of the present invention, worn next to the user's body.

FIG. 67 depicts a remote controller of an embodiment of the present invention, used without wearing or placing adjacent to the body.

FIG. 78 depicts a closeup side view of the stomach measurement device shown in FIG. 77, showing the frusto-conical member in a deflated state.

FIG. 79 depicts a perspective view of a pyloric element equipped with a constriction element, in an embodiment of the present invention.

FIG. 80 depicts a perspective view of the pyloric element shown in FIG. 79, with the constriction element engaged to constrict the pyloric element.

DETAILED DESCRIPTION OF THE INVENTION

The detailed description set forth below in connection with the appended drawings is intended as a description of presently-preferred embodiments of the invention and is not intended to represent the only forms in which the present invention may be constructed or utilized. The description sets forth the functions and the sequence of steps for constructing and operating the invention in connection with the illustrated embodiments. It is to be understood, however, that the same or equivalent functions and sequences may be accomplished by different embodiments that are also intended to be encompassed within the spirit and scope of the invention.

Figure 1:
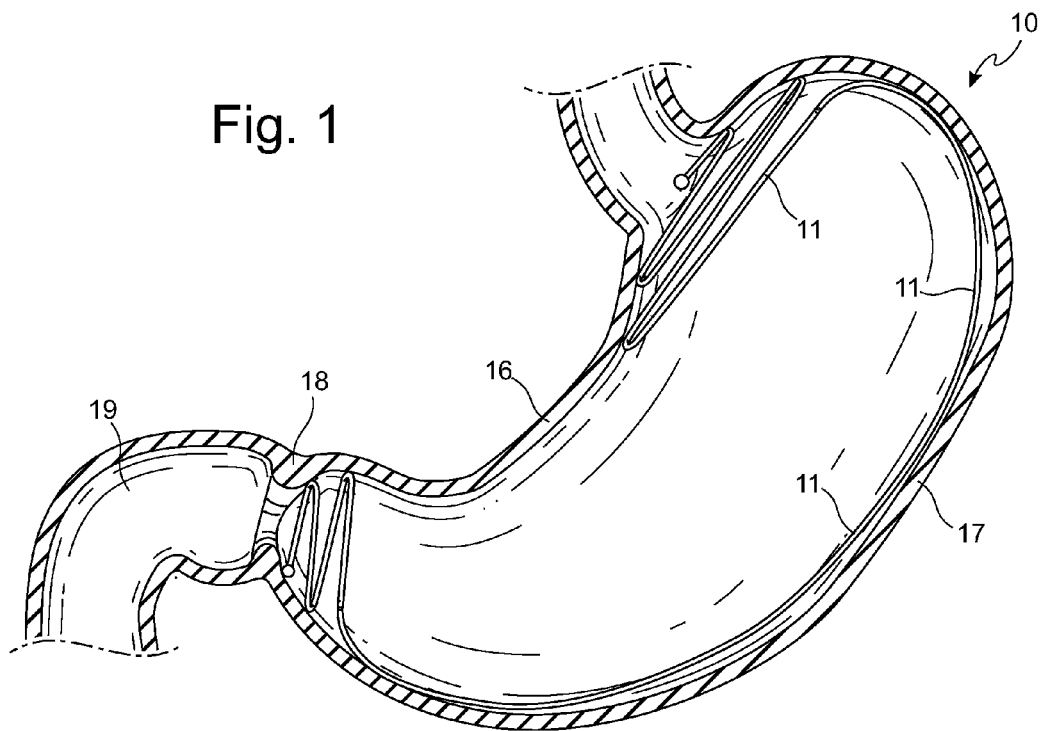
FIG. 1 depicts a side view of a single wire embodiment the bariatric device of the present invention located within a cross-section of a stomach.
Figure 2:
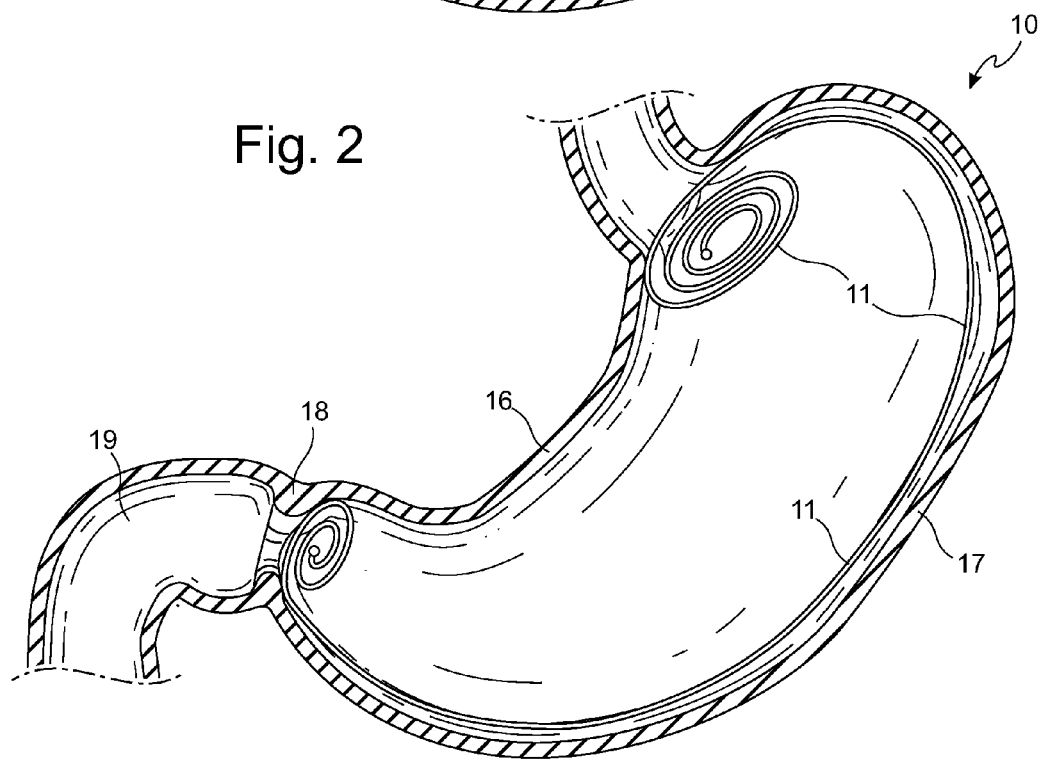
FIG. 2 depicts a side view of an alternative single wire embodiment the bariatric device of the present invention located within a cross-section of a stomach.

The most basic embodiment of the bariatric device 10 may have a single piece of Nitinol wire 11 which is shape set into a shape, but can be pulled under tension into a generally narrow and straight form, to allow for insertion of the device 10 through the esophagus. In such an embodiment, the elements may all be seamlessly integrated as one wire structure. See FIGS. 1 and 2. Depending on the size of the stomach, the shape set wire may impart an outwardly biasing force to the proximal and distal elements of the bariatric device 10, which may vary during peristalsis.

Figure 3:
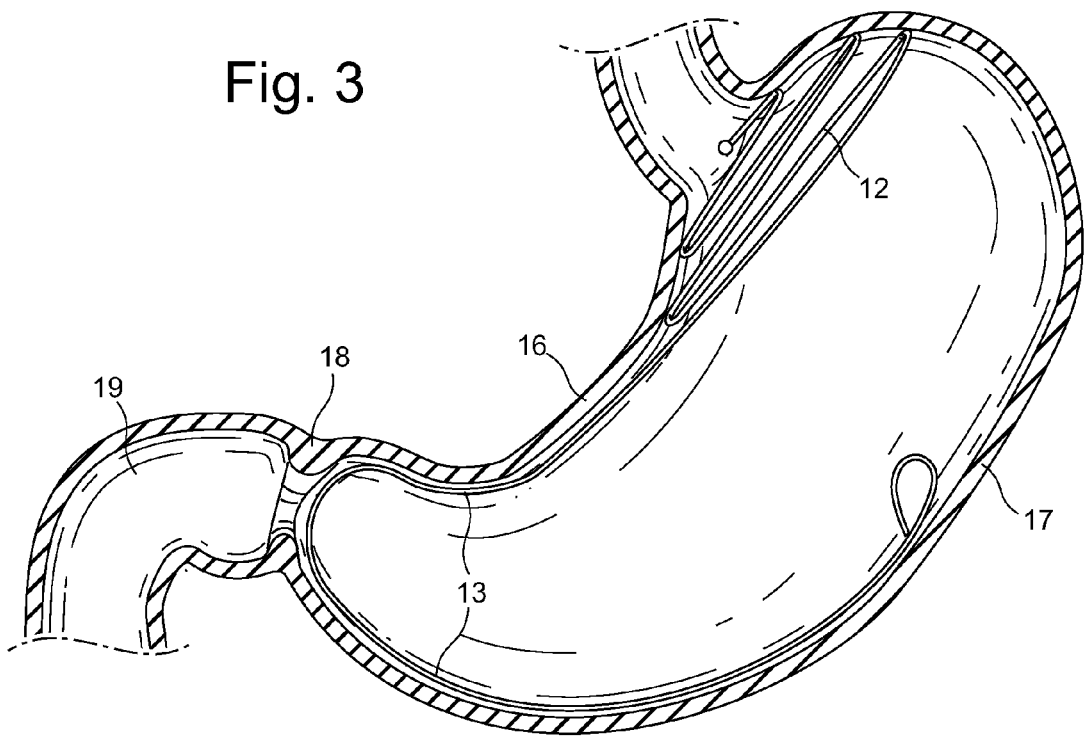
FIG. 3 depicts a side view of an embodiment the bariatric device of the present invention located within a cross-section of a stomach.
Figure 4:
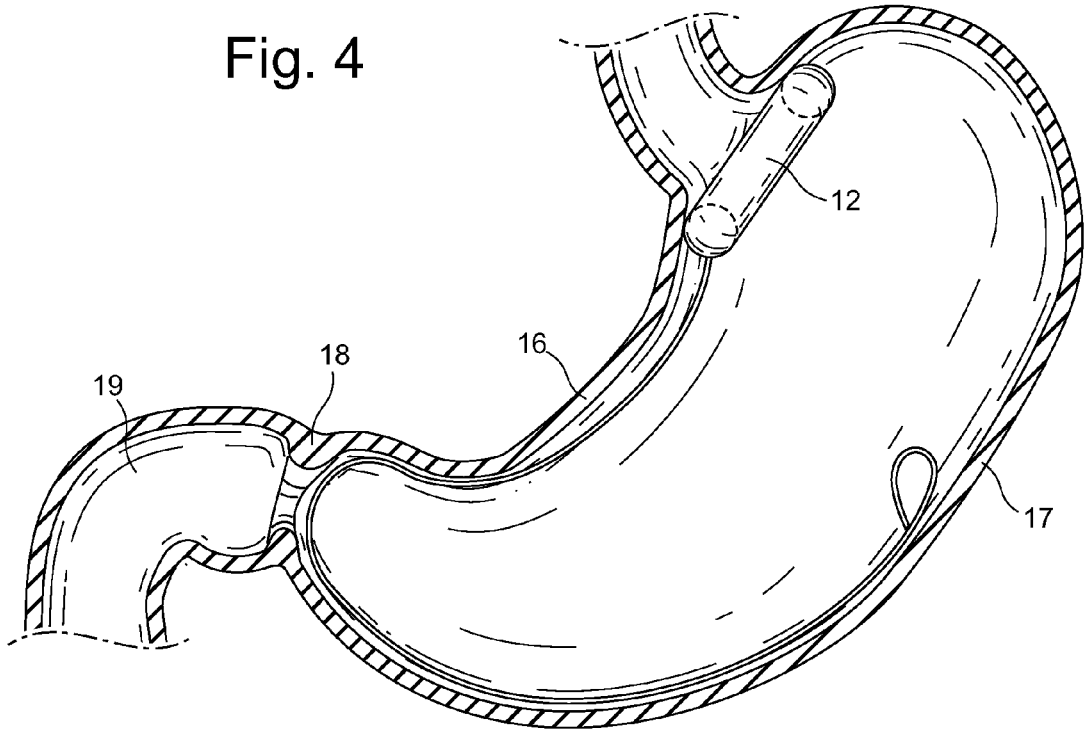
FIG. 4 depicts a side view of a side view of an embodiment the bariatric device of the present invention located within a cross-section of a stomach.
Figure 5:
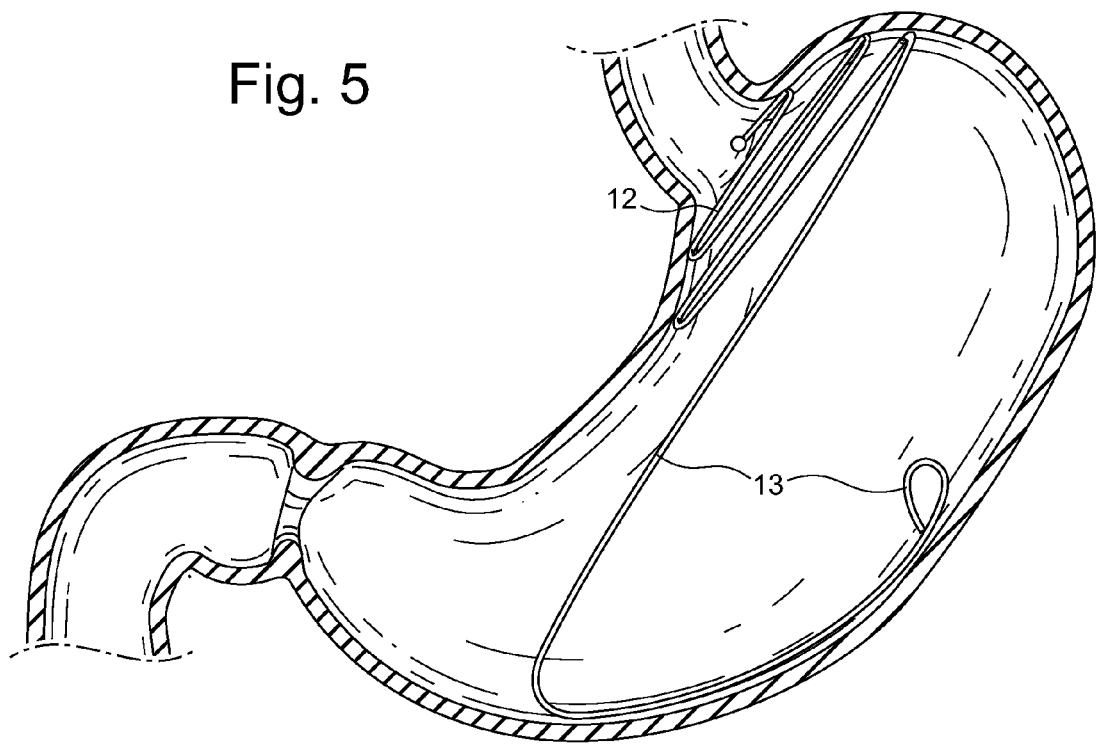
FIG. 5 depicts a side view of a side view of an embodiment the bariatric device of the present invention located within a cross-section of a stomach.

As for the two-element embodiment (cardiac element 12 and positioning element 13), when tension to stretch the device 10 is released, it may coil into a ring, cone or spiral at one end near the upper stomach or cardia, and curve into a shape to relatively match the lesser and greater curve of the stomach 16, 17 and be of sufficient size to not migrate across the pyloric valve 18 into the duodenum 19. See FIGS. 3 and 4. The positioning element 13 could also have a straighter section that does not follow the lesser curve 16, but does follow the greater curve 17. See FIG. 5. In this embodiment, the positioning element 13 could also be in a different plane such that is perpendicular to that shown in FIGS. 3, 4, and 5, or the device 10 could contain multiple members that were in the same plane and perpendicular to the plane shown in FIGS. 3, 4, and 5. To use a plane perpendicular, the element could follow the midline of the stomach between the greater and lesser curves 17, 16, and would contact the posterior and anterior walls of the stomach.

Figure 6:
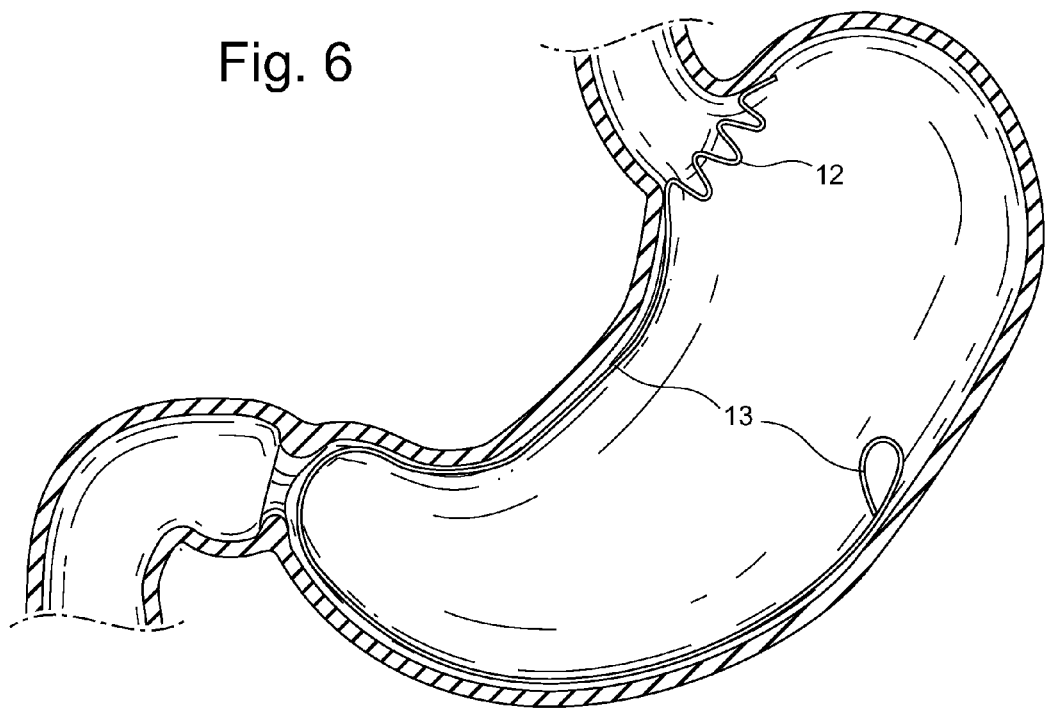
FIG. 6 depicts a side view of a side view of an embodiment the bariatric device of the present invention located within a cross-section of a stomach.
Figure 7:
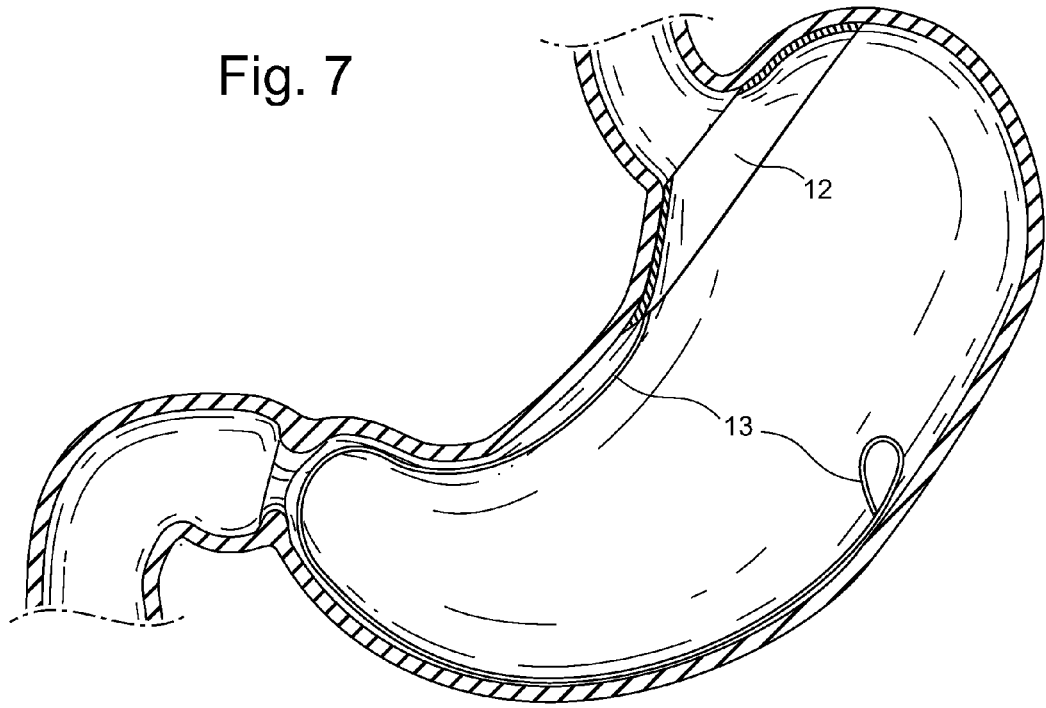
FIG. 7 depicts a side view of a side view of embodiment the bariatric device of the present invention located within a cross-section of a stomach.

As noted above, the cardiac element 12 may be in the form of a ring, which can be formed from a single Nitinol wire 11, or a wide variety of other suitable materials, such as silicone, Nitinol encased in silicone, etc. Preferably, the ring can be compressed or collapsed for insertion through the esophagus, then regain or reform its shape after placement in the stomach. The ring could lock or not lock after forming, or could be continuous prior to placement. A variation may have the ring closed, locked, or continuous prior to placement down the esophagus. See FIG. 4. The ring could be compressed enough to fit within a placement tube or delivery catheter for placement through the esophagus. The cross-section of the ring could be round, flat, oval, convoluted, wavy or knobby to add pressure points that continuously move to stimulate the upper stomach or cardia during peristalsis and reduce the potential for overstressing a certain area. See FIG. 6. The cardiac element 12 could also be a cone of flexible material or combinations of materials. See FIG. 7. The device 10 need not be fixed into place but may be moveable within the stomach. Once the device 10 is placed, preferably, it is generally self-seating to ensure that it sits in the correct general areas similar to the way a contact lens re-seats itself on the cornea even after it is moderately pushed off center. Since the stomach is nonsymmetrical, the device 10 could be formed to have a bias to ensure that it seats into the upper stomach or cardia and within the lower stomach as needed. Similarly, the action of peristalsis would create additional satiety signals to be sent each time a wave passes by the device 10 it could slip around in the stomach varying the pressure placed on the upper and lower stomach over time pending the force of peristalsis.

Figure 10:
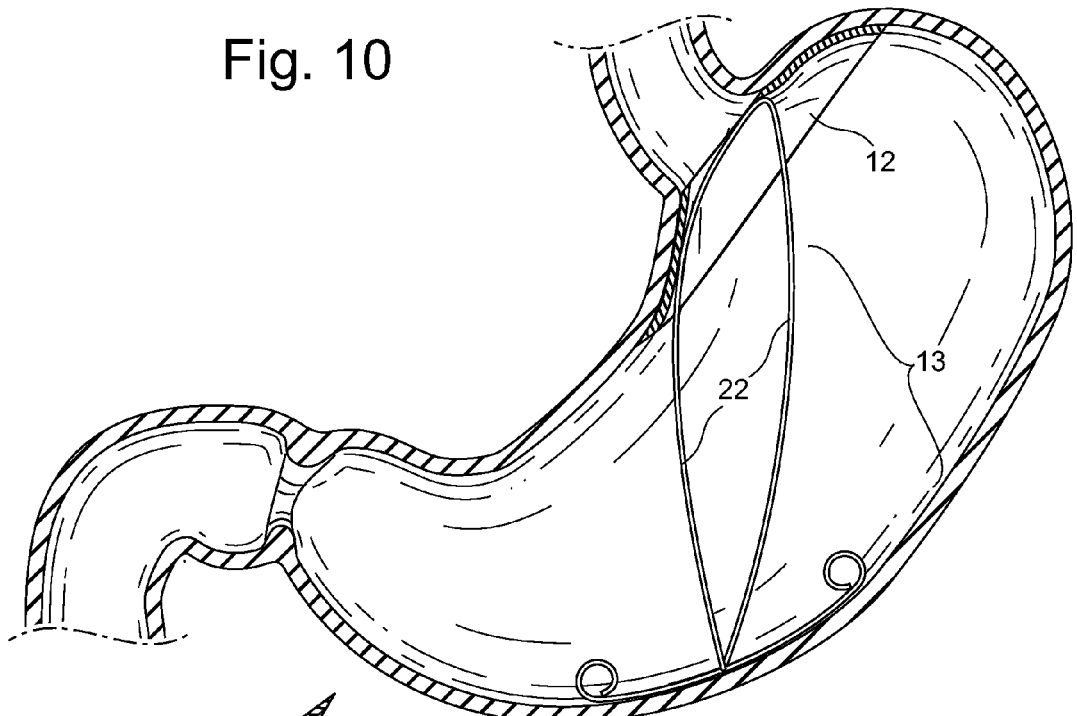
FIG. 10 depicts a side view of an embodiment the bariatric device of the present invention located within a cross-section of a stomach.
Figure 11B:
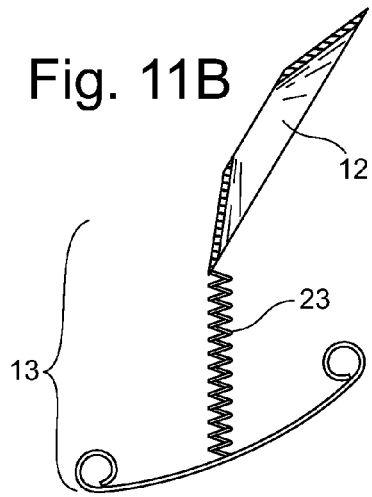
FIG. 11B depicts a side view of an embodiment the bariatric device of the present invention.
Figure 11A:
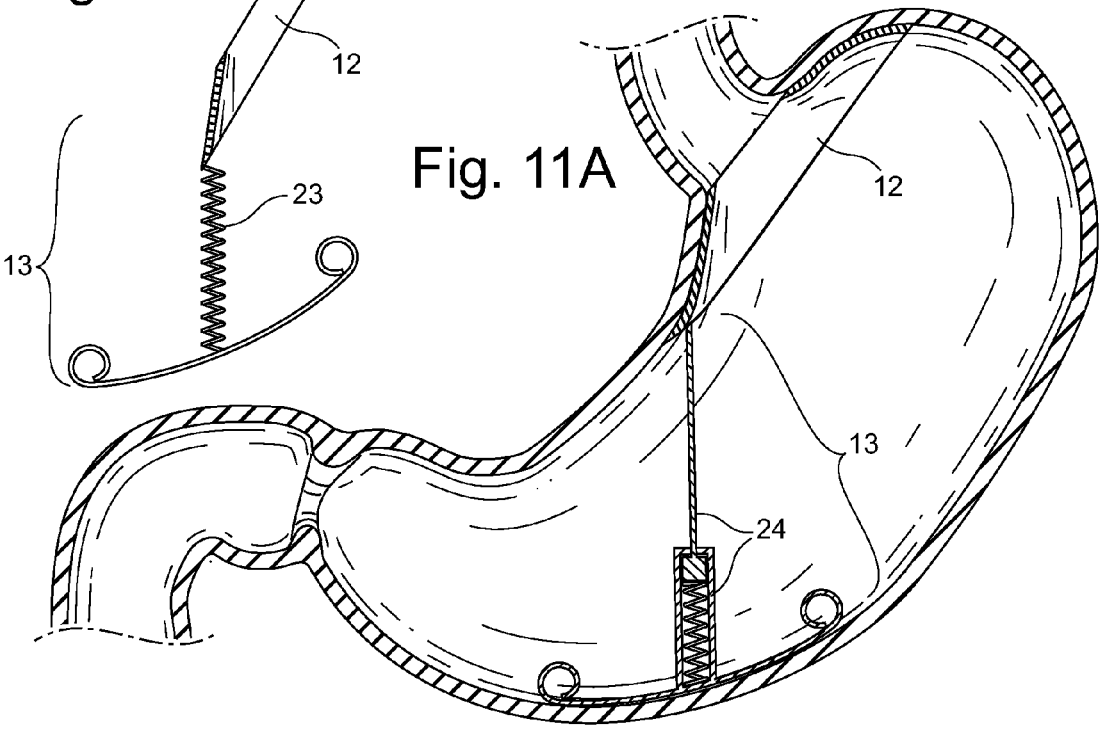
FIG. 11A depicts a side view of an embodiment the bariatric device of the present invention located within a cross-section of a stomach.

The positioning element 13 could comprise two or more positioning members 20. For example, a member 20 could follow the curve of the greater curve 17 and the other member 20 could provide the support between the first member and the cardiac element 12. To further improve the design, the two members 20 of the positioning element 13 could articulate and or rotate relative to one another to accommodate for the movement of the stomach. See FIGS. 8A, 8B, 9A and 9B. As shown, the positioning element 13 could also contain a pyloric feature 21 that could translate along the great curve in the pyloric region 42 and prevent the device 10 from passing through the pyloric valve 18. Another variation for the positioning element 13 with multiple members would be to have a member that is a loop 22 and is attached to a member with a support that follows the greater curve 17. See FIG. 10. The loop member 22 could flex in shape to change in length and width to accommodate for the stomachs movement during peristalsis. The positioning member could also be a spiral spring 23 or spring plunger assembly 24. See FIGS. 11A and 11B. This member could also have a manual mechanism for adjusting the maximum length, such as having a set screw block the distance that the plunger could travel. Details on various adjusting mechanisms are discussed below.

The positioning element 13 could also be a spiral or spring, or multiple spirals or multiple springs to create a flexible structure. See FIG. 11B. The positioning element 13 could also be bisected into two members that stack, telescope or articulate, such as those shown in FIGS. 8A-9B. The positioning element 13 could also have a joint such as a ball and socket type joint 29 or may be connected by magnets. As mentioned above, these devices could also contain an additional positioning element 13 that is in a plane perpendicular or other angle to that shown in the figures, so that the positioning element 13 contacts the midline of the stomach between the greater and lesser curves 17, 16, and contacts the posterior and anterior walls of the stomach.

In any of the embodiments discussed herein, the positioning and/or connecting elements 13, 25 may be constructed of materials, or in such a manner, that may impart an outwardly biasing force, to push on the cardiac and/or positioning or pyloric elements. Such outwardly biasing force may impart constant or intermittent pressure to various parts of the stomach, through the cardiac element 12, the pyloric element 26, the positioning or connecting elements 13, 25, or any combination thereof.

Figure 13:
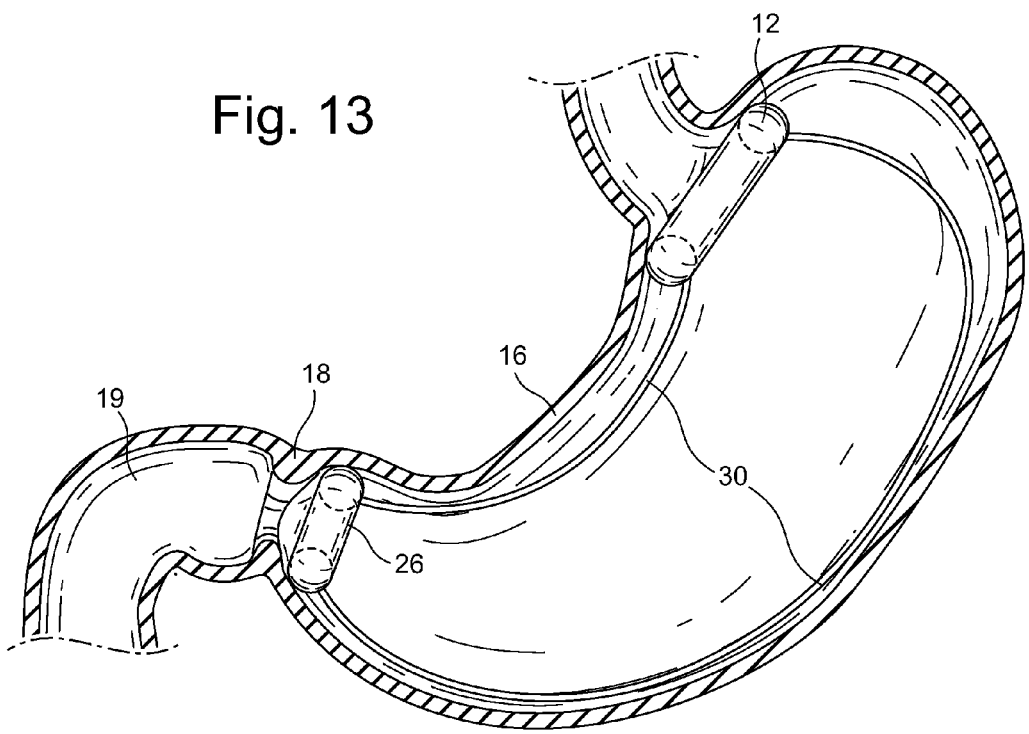
FIG. 13 depicts a side view of an embodiment of the bariatric device of the present invention, located within a cross-section of a stomach.
Figure 14:
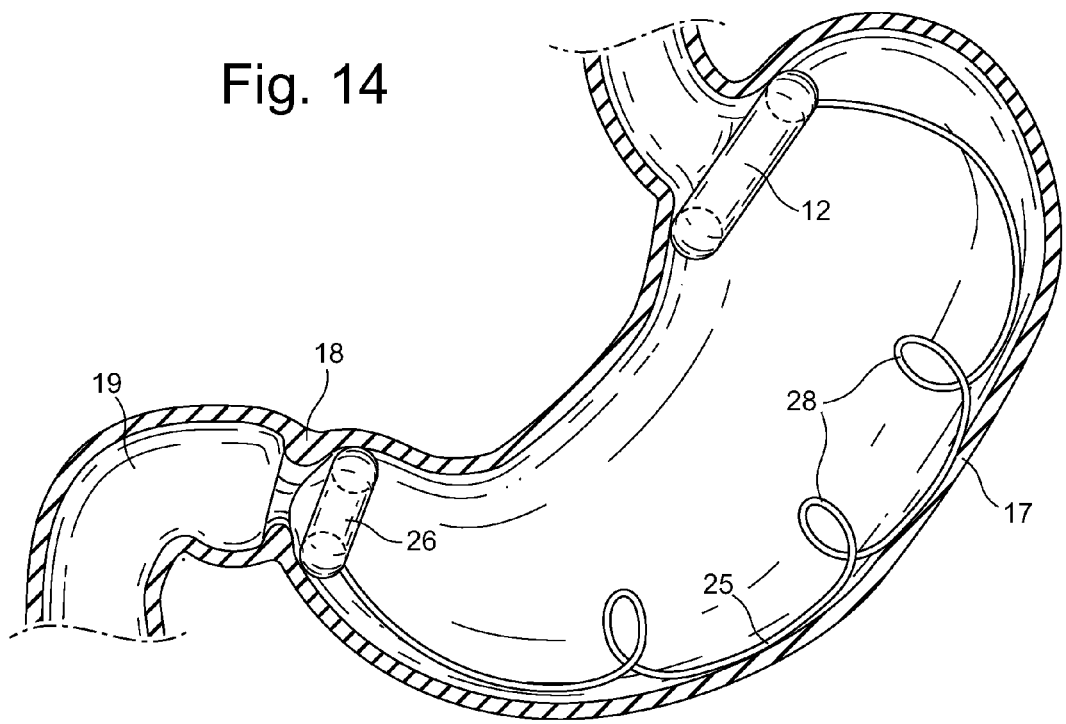
FIG. 14 depicts a side view of an embodiment of the bariatric device of the present invention, located within a cross-section of a stomach.

In the three-element embodiment (cardiac, pyloric, and connecting elements 12, 26, 25), the three elements may all be seamlessly integrated as one wire structure. When tension to flex, compress or stretch the device 10 is released, it may coil into a ring or loop near the cardia 40, and coil into a ring or loop near the pyloric region 42, with a curved member to connect the two elements that is shaped to relatively match the greater curve 17 of the stomach. The curve could also match the lesser curve 16 of the stomach or both. See FIGS. 12 and 13. The connecting element 25 could curve into a single ring, or it could curve into a spiral. See FIG. 14.

Figure 15:
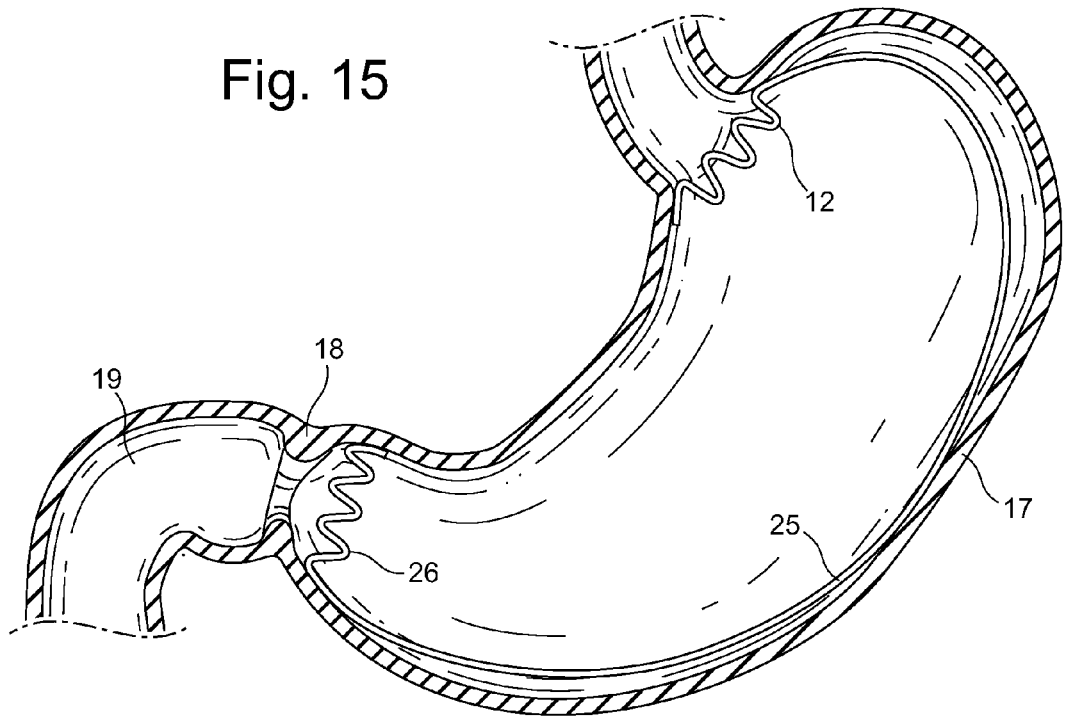
FIG. 15 depicts a side view of an embodiment of the bariatric device of the present invention, located within a cross-section of a stomach.
Figure 16:
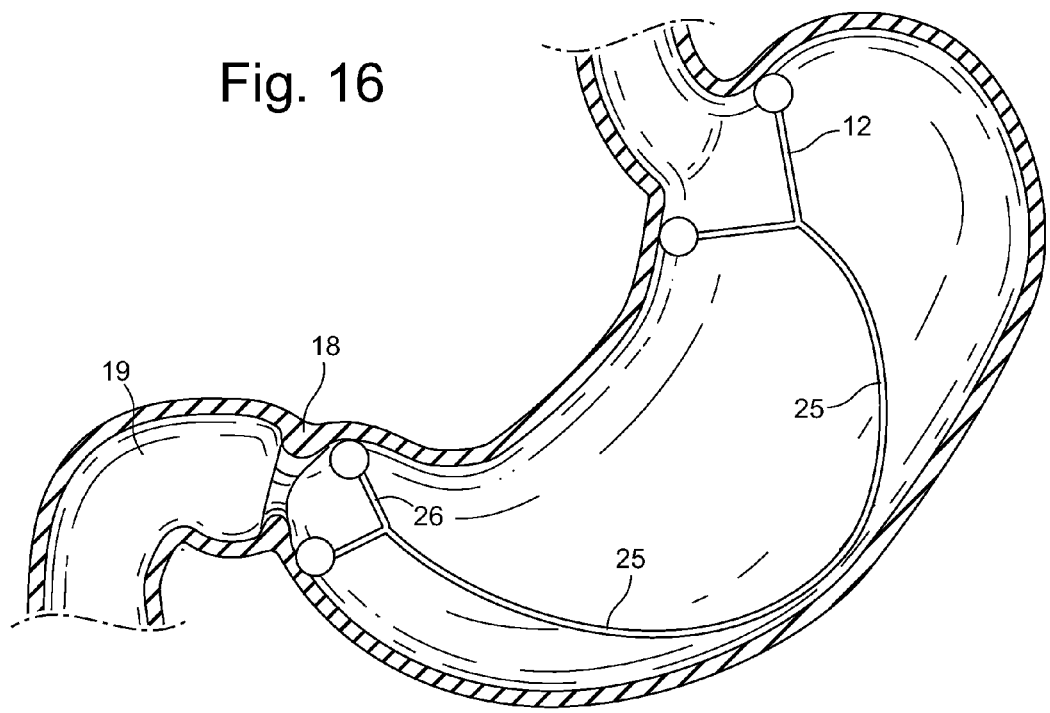
FIG. 16 depicts a side view of an embodiment of the bariatric device of the present invention, located within a cross-section of a stomach.
Figure 17:
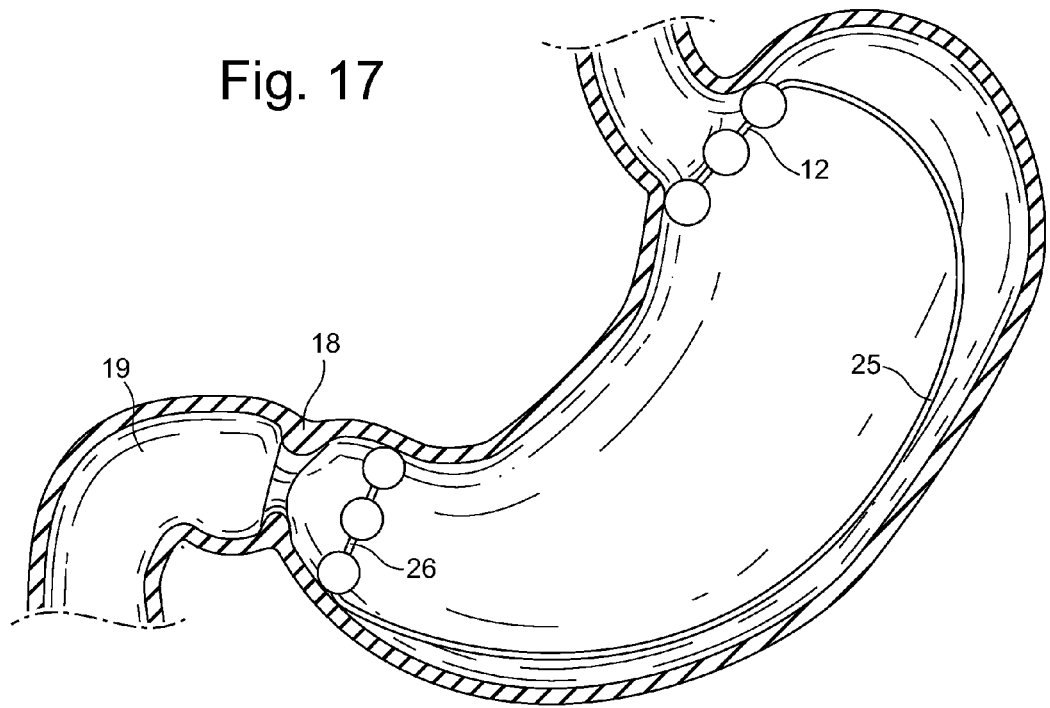
FIG. 17 depicts a side view of an embodiment of the bariatric device of the present invention, located within a cross-section of a stomach.

As in other embodiments, the rings at each end could lock or not lock after forming, the rings may be closed, locked or continuous prior to placement down the esophagus, and could be compressed enough to fit within a placement tube for placement through the esophagus. See FIGS. 12 and 13. As with other embodiments, the elements of the bariatric device 10 may have a variety of shapes to add pressure points that continuously move to stimulate the cardiac region 40 during peristalsis. See FIGS. 15, 16, and 17. The device 10 need not be fixed into place but may be moveable, and generally self-seating. The device 10 may have a bias to fit the nonsymmetrical stomach shape and ensure that it seats into the cardiac region 40 and pyloric region 42. Similarly, the action of peristalsis could create additional satiety signals as the device 10 moved in the stomach varying the pressure placed on the cardiac region 40 and/or the pyloric region 42 over time.

Figure 12:
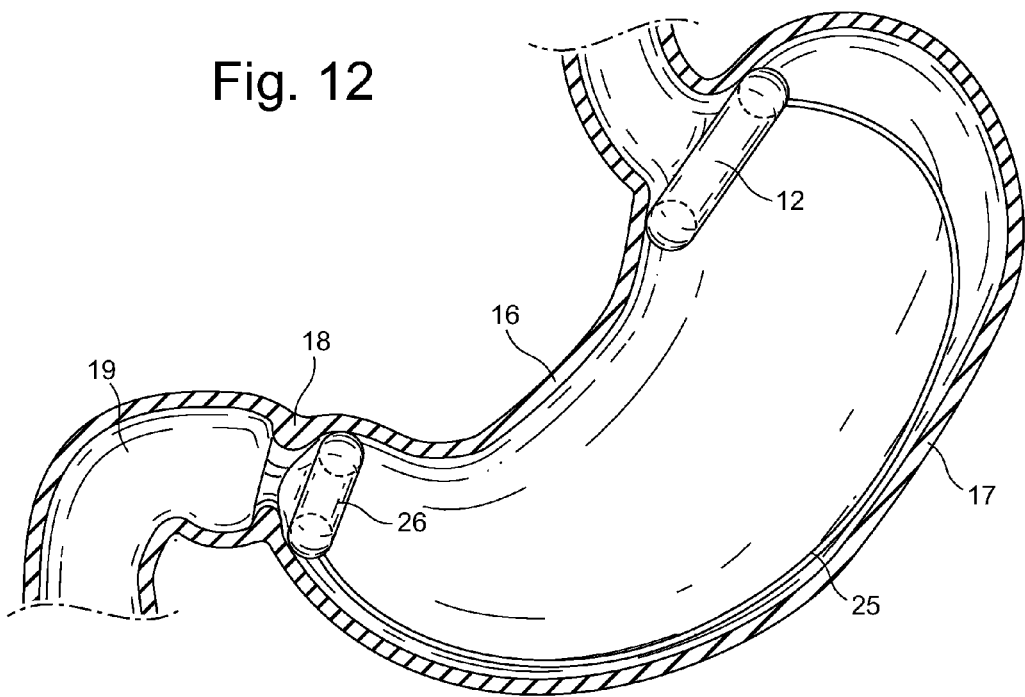
FIG. 12 depicts a side view of an embodiment of the bariatric device of the present invention located within a cross-section of a stomach.
Figure 18:
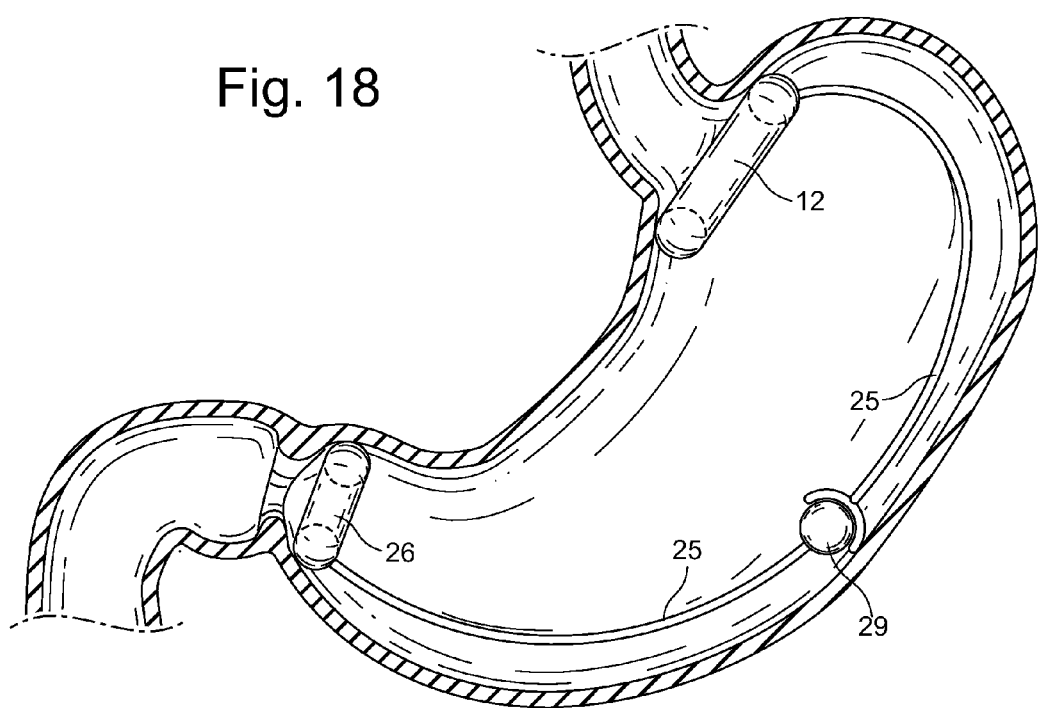
FIG. 18 depicts a side view of an embodiment of the bariatric device of the present invention, located within a cross-section of a stomach.

In the three-element design shown in FIG. 12, the connecting element 25 connecting the two rings could follow the natural curve of the stomach to match the greater or lesser curve of the stomach 17, 16, or could have both. This would aid in the seating of the device 10 in the stomach after placement. The connecting element 25 could have one or more connecting members 30 connecting the cardiac and pyloric elements 12, 26. See FIG. 13. However, these members 30 should be flexible enough to allow for natural peristalsis to occur, natural sphincter function to occur and to not cause erosion or irritation of the stomach wall or significant migration into the esophagus or duodenum 19. There could also be struts or supports that help to support the geometric shape of the rings to the connecting element 25. The connecting element 25 could also be a spiral 28 or multiple spirals to create a flexible structure. See FIG. 14. The connecting element 25 could also be bisected into two members that stack, telescope or articulate. The connecting element 25 could also have a joint such as a ball and socket type joint 29 or may be connected by magnets. See FIG. 18.

Figure 19:
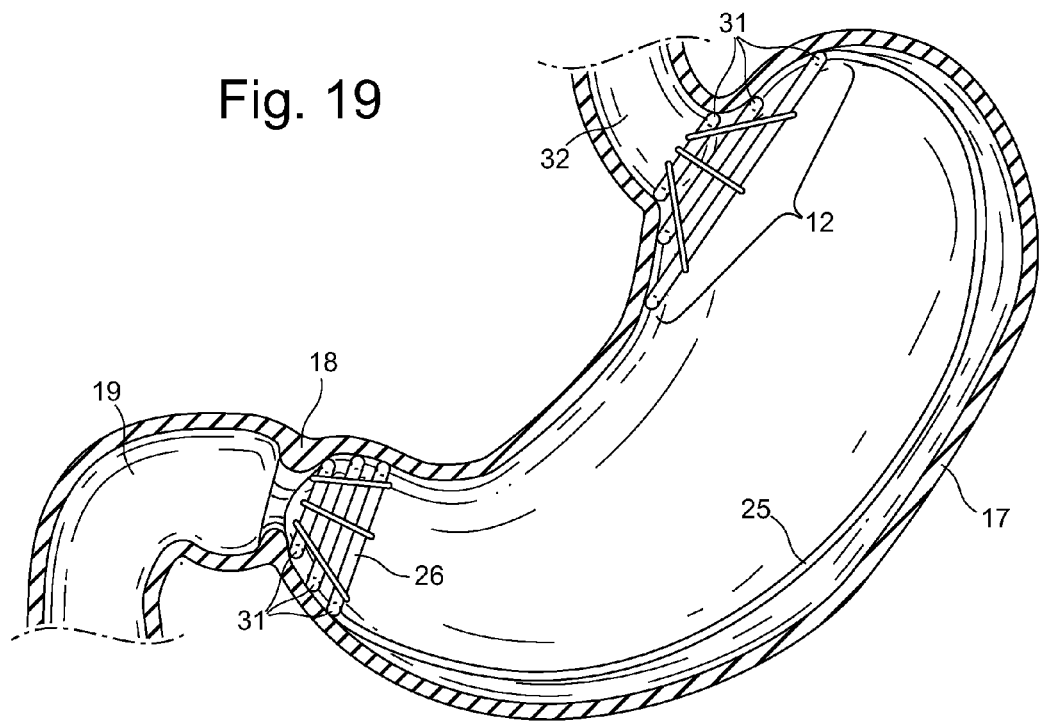
FIG. 19 depicts a side view of an embodiment of the bariatric device of the present invention, located within a cross-section of a stomach.

In another variation of the embodiments, there could be several rings 31 at each end of the device 10 to create an area of pressure at the upper stomach or cardia 40. See FIG. 19. The rings 31 should be sized appropriately to ensure that they do not protrude or slip into the esophagus 32 or into the duodenum 19, unless a variation of this embodiment is designed to have some portion of the device 10 enter those regions. This will allow the device 10 to apply pressure to the upper stomach or cardia 40 without fixation or sutures. The force against the pyloric region 42 and/or lower stomach will provide the counterforce against the upper stomach or cardia 40. At the same time, the force or contact against the pyloric region 42 and/or lower stomach may signal the body to stop eating. This force would mimic having a meal in the stomach with subsequent peristalsis, and sending the signal to stop eating. The multiple rings 31 could take the form of a spiral or could be separate rings 31 connected together. After reforming in the stomach, the rings 31 could lock, not lock, or be continuous. There are several ways that these elements could lock to form a ring.

Another option for the cardiac element 12 would be to have a surface that contacts the upper stomach or cardia 40 such as a hemispherical or conical shaped shell 33 or balloon. The shape could also be asymmetrical but similar to a cone or hemisphere. This could be a thin walled element and could contain a lumen or no lumen through which food could pass. See FIG. 20. In the case where there is no opening, the food would have to pass over the hemisphere or cone 33 which would have adequate flexibility to allow the food to pass into the stomach. This may require the esophagus 32 to work harder to pass the food over the element and could better stimulate the stretch receptors in the stomach and indirectly in the esophagus. In another alternative, the hemispherical shell 33 could have multiple grooves or channels to aid in allowing food to pass. In the case where there is a lumen in the cardiac element 12, it could be open or it could have a valve 35 that requires some force to allow food to pass through. An option could also be to have an esophageal member 36 that extends into the esophagus 32 for additional esophageal stimulation. This esophageal member 36 could be tethered by a thin structural member to support the esophageal member 36, but not prevent the esophageal sphincter from closing. As mentioned above, this may require the esophagus 32 to work harder to pass the food and may better stimulate the stretch receptors in the stomach and indirectly in the esophagus. This esophageal member 36 could be a large tube, a small tube, a ring, a small sphere, multiple small spheres, or other suitable shapes. This type of embodiment could also be adapted for the 2 element design, where the cardiac element 12 is connected to a positional feature as shown in FIG. 21. All aspects of the above embodiment would apply towards this embodiment as well.

Figure 20:
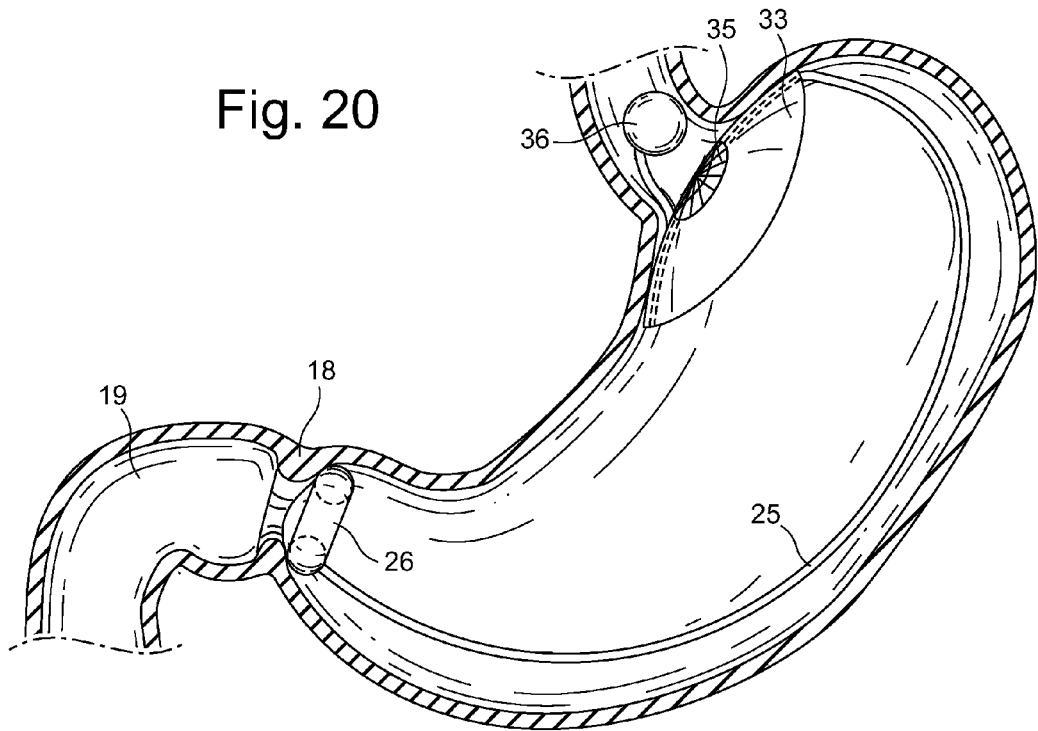
FIG. 20 depicts a side view of an embodiment of the bariatric device of the present invention, located within a cross-section of a stomach.
Figure 21:
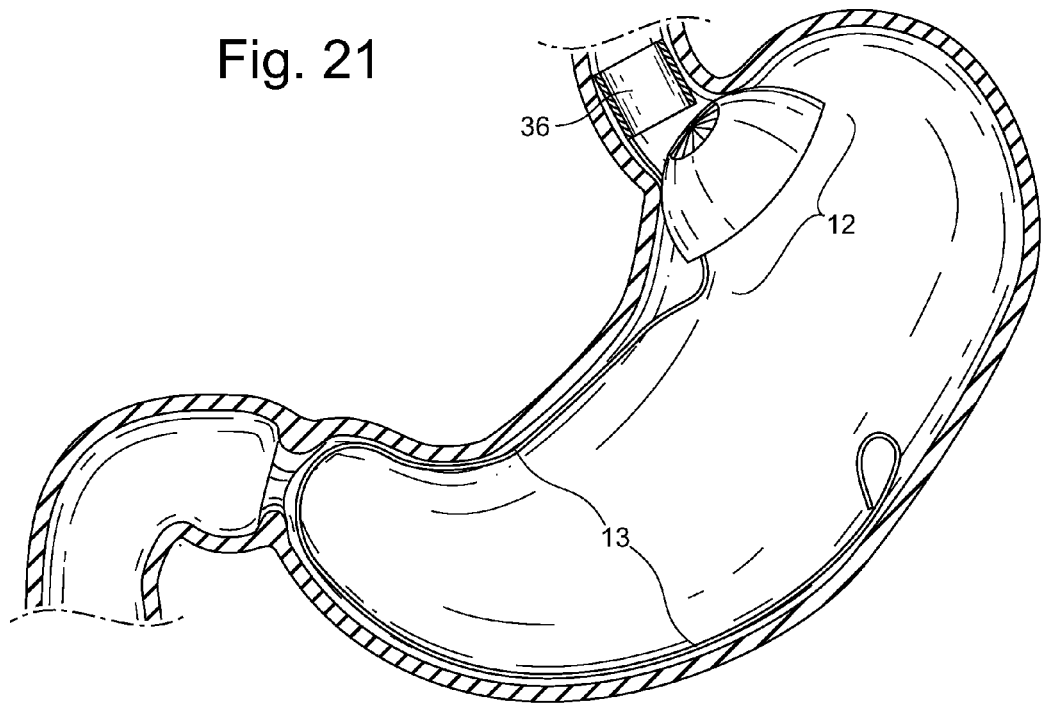
FIG. 21 depicts a side view of an embodiment of the bariatric device of the present invention, located within a cross-section of a stomach.
Figure 83:
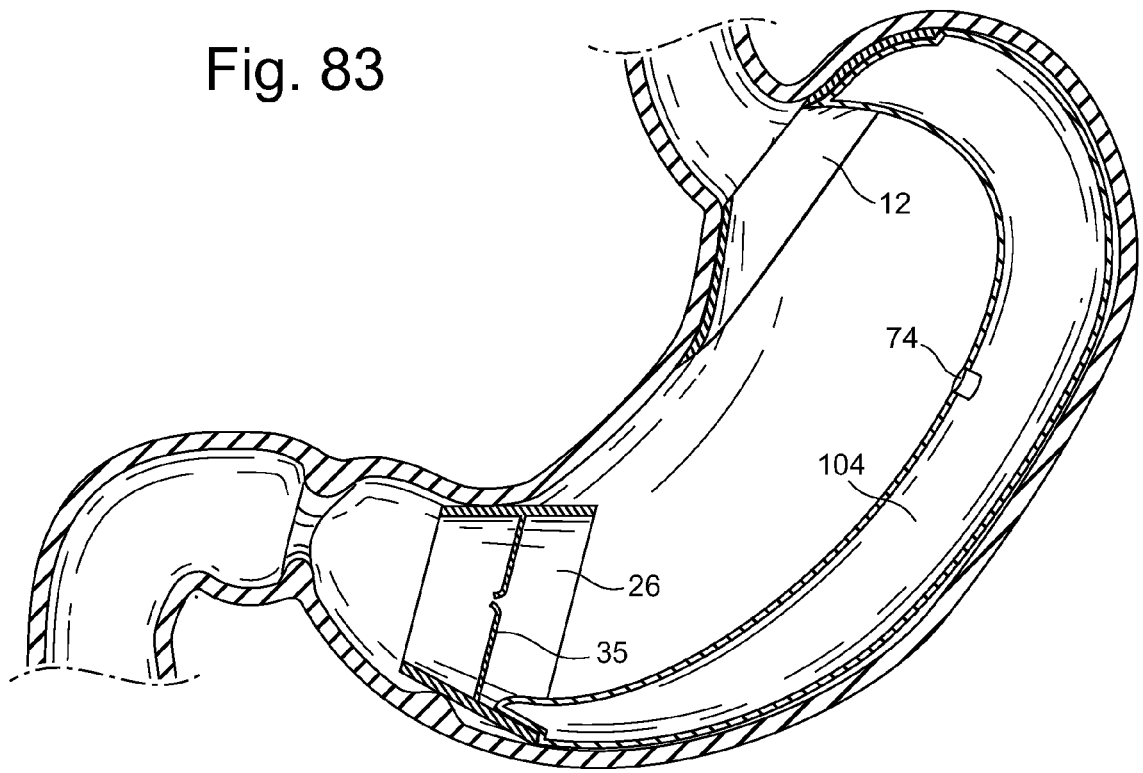
FIG. 83 depicts a cross-section view of an embodiment of a bariatric device within the scope of the present invention showing a pyloric element with a valve passing across the midsection of the pyloric element to slow down the passage of food.

The pyloric element 26 could contain a lumen or could contain a valve similar to the valve shown in FIG. 20 for the cardiac element 12. This could reduce the speed of food passing through the pyloric element 26 if desired. This valve 35 could be a thin membrane of silicone with a single or multiple slits punch through the center, or other types of valves could be used. FIG. 83 shows a pyloric element with a valve 35 passing across the midsection of the pyloric element 26 to slow down the passage of food.

The connecting element could also be an inflatable balloon 104 or incorporate an inflatable balloon. FIG. 83 depicts a connecting element 25 that could be comprised of an inflatable balloon 104. This inflatable body 104 could be compressed for placement and then inflated with a fluid to provide structure and adjustability after placement in the stomach. An inflation element 74 such as an injection port may be attached to the balloon where an instrument could be used to add or remove fluid to the inflatable balloon 104. The positioning element 13 could also contain or comprise an inflatable balloon.

Figure 22:
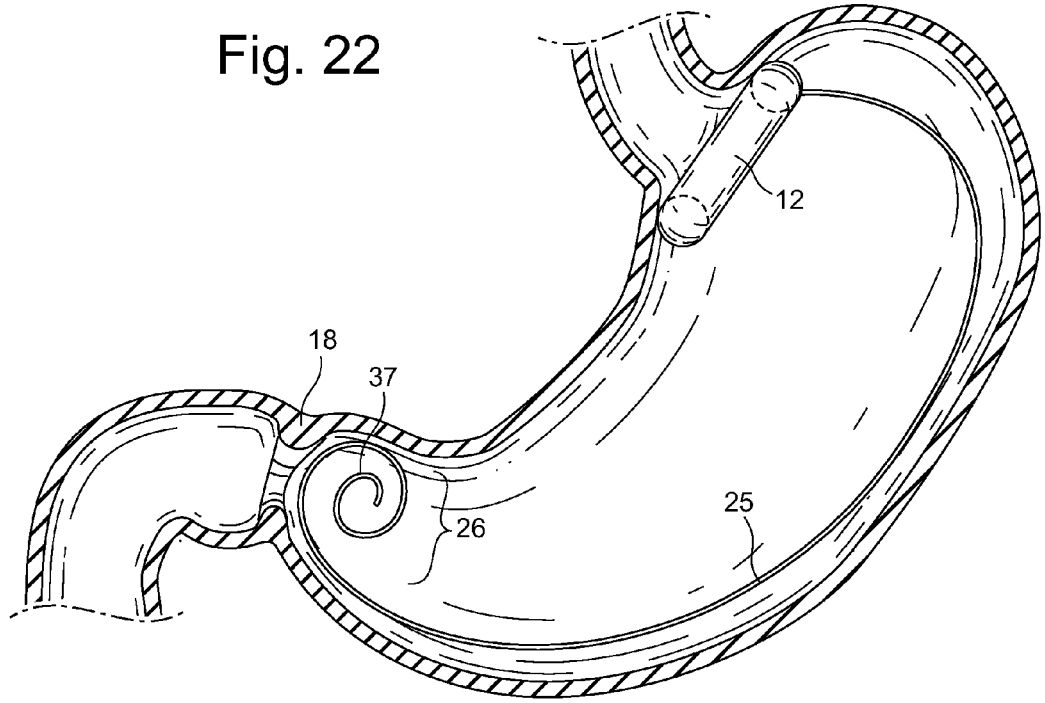
FIG. 22 depicts a side view of an embodiment of the bariatric device of the present invention, located within a cross-section of a stomach.

With respect to the three-element design, another alternative embodiment for the pyloric element 26 would be to change the orientation to allow the axis of the loop 37 to be perpendicular to the axis of the pyloric valve 18 similar to some embodiments described for the two-element design. This may simplify manufacturing construction yet perform the same function. In such an embodiment, the pyloric element 26 could have the loop in a single plane, two crossed planes, or multiple planes. See FIG. 22.

Figure 23A:
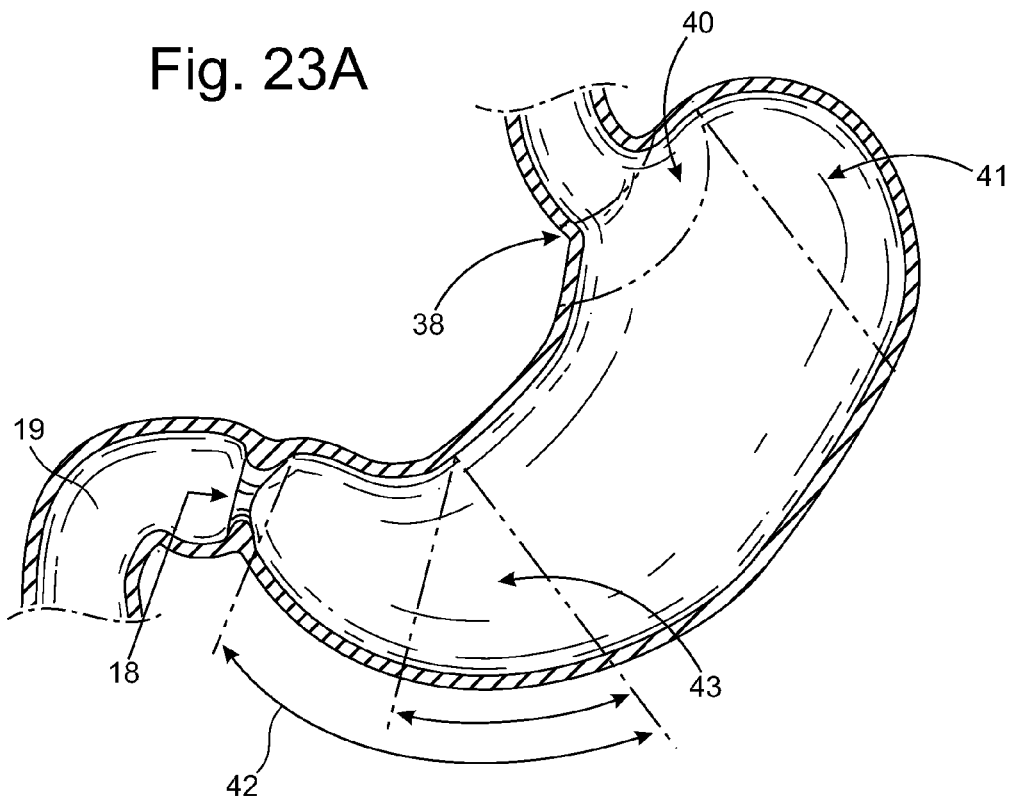
FIG. 23A depicts a side view of a cross-section of a stomach, identifying anatomical features.
Figure 23B:
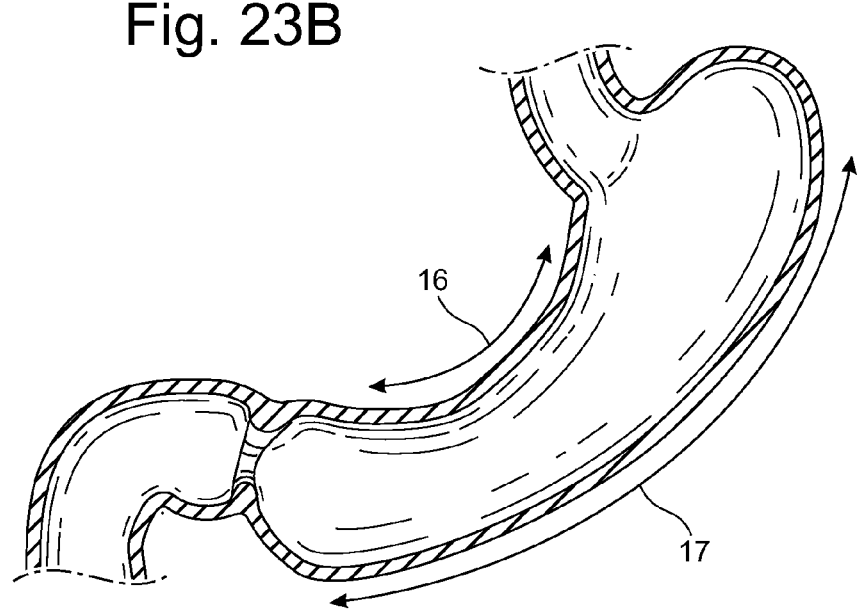
FIG. 23B depicts a side view of a cross-section of a stomach showing its approximate shape when undergoing contractions due to peristalsis.

As mentioned above, the stomach experiences peristaltic waves when something is swallowed. FIG. 23A depicts a stomach cross-section showing the Z line and gastroesophageal ("GE") junction 38, the cardia or cardiac region 40, the fundus 41, the pyloric region 42, the pyloric antrum 43, the pyloric valve 18, and the duodenum 19. FIG. 23B depicts the stomach's lesser curve 16 and greater curve 17. FIGS. 23A and 23B respectively show a representation of the stomach profile when the stomach is at rest and when the stomach is fully contracted during peristalsis and the change in stomach diameter and length. Due to the change in stomach profile, it may be advantageous to have a design that can flex to change with the stomach profile to allow the design to slide or translate along the greater curve 17 or flex as needed, but maintain the relative position of the cardiac element 12. As mentioned above, the two-element device 10 could also contain a member or an additional positioning element 13 that is in a plane perpendicular or other angle to that shown in the figures, so that the element contacts the midline of the stomach between the greater and lesser curves 17, 16, and contacts the posterior and anterior walls of the stomach. This would maintain the position within the stomach with less flex needed to maintain the position with the greatest motion taking place along the greater curve 17, and least motion taking place along the lesser curve 16.

Figure 24:
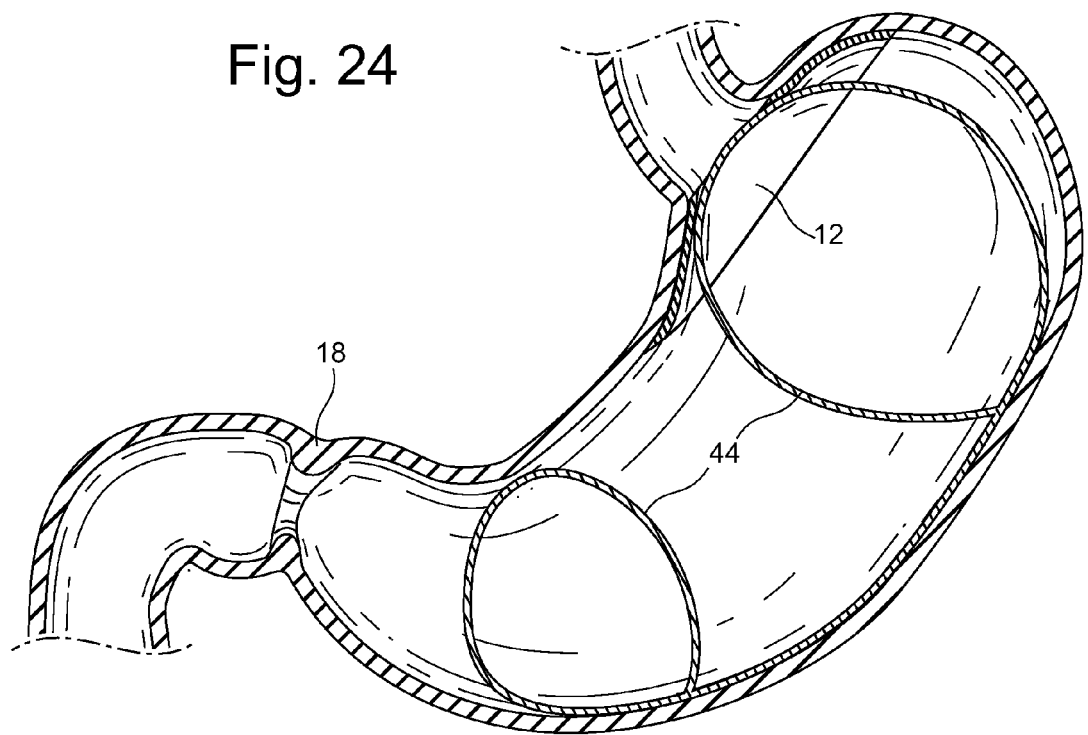
FIG. 24 depicts a side view of an embodiment of the bariatric device of the present invention, located within a cross-section of a stomach.
Figure 25:
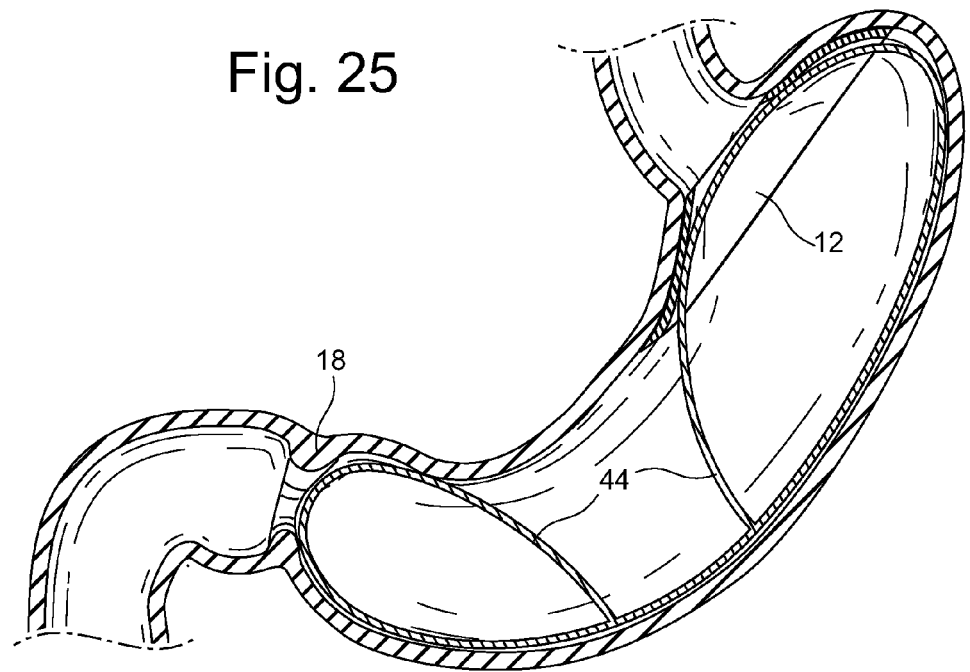
FIG. 25 depicts a side view of the embodiment of the present invention shown in FIG. 24, located within a cross-section of a stomach that is undergoing contraction due to peristalsis.

FIGS. 24 and 25 show an alternate embodiment of the two-element design to adapt to stomach profile changes. In FIG. 24, it shows the cardiac element 12 engaging the upper stomach region while the positioning element 13 is a spring with two closed loops 44 at each end which can compress and flex to accommodate peristalsis within the stomach. FIG. 25 shows these loops 44 compressing during peristalsis to allow the device 10 to maintain its relative position in the stomach and preventing it from migrating past the pyloric valve 18.

Figure 26:
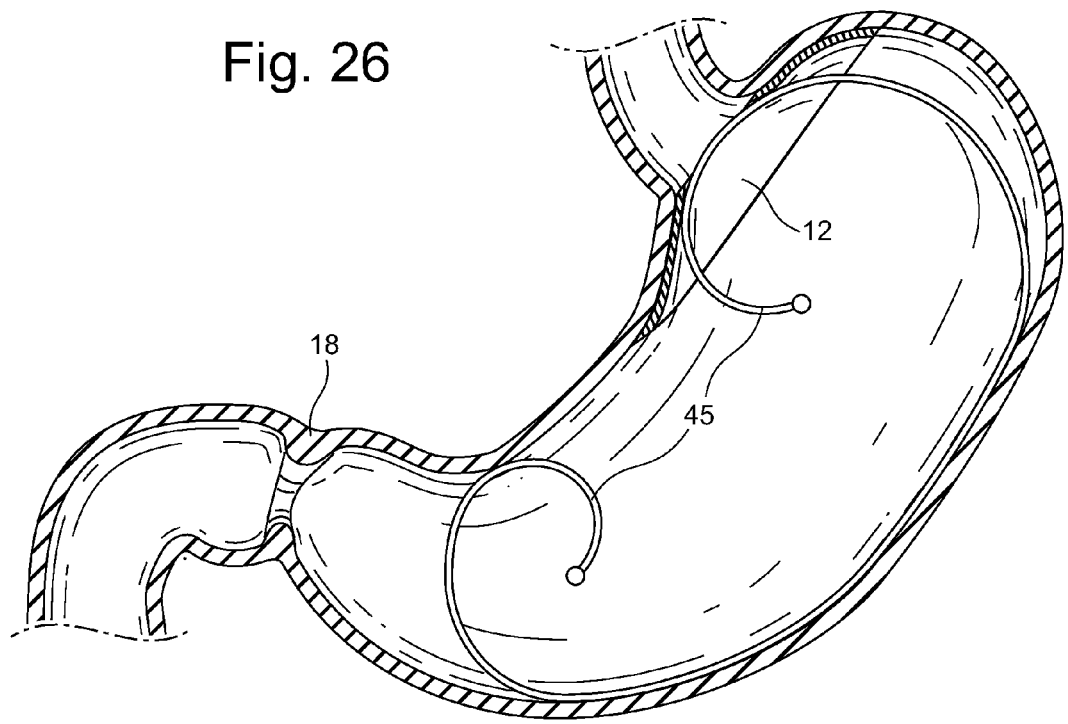
FIG. 26 depicts a side view of an embodiment of the bariatric device of the present invention, located within a cross-section of a stomach.
Figure 27:
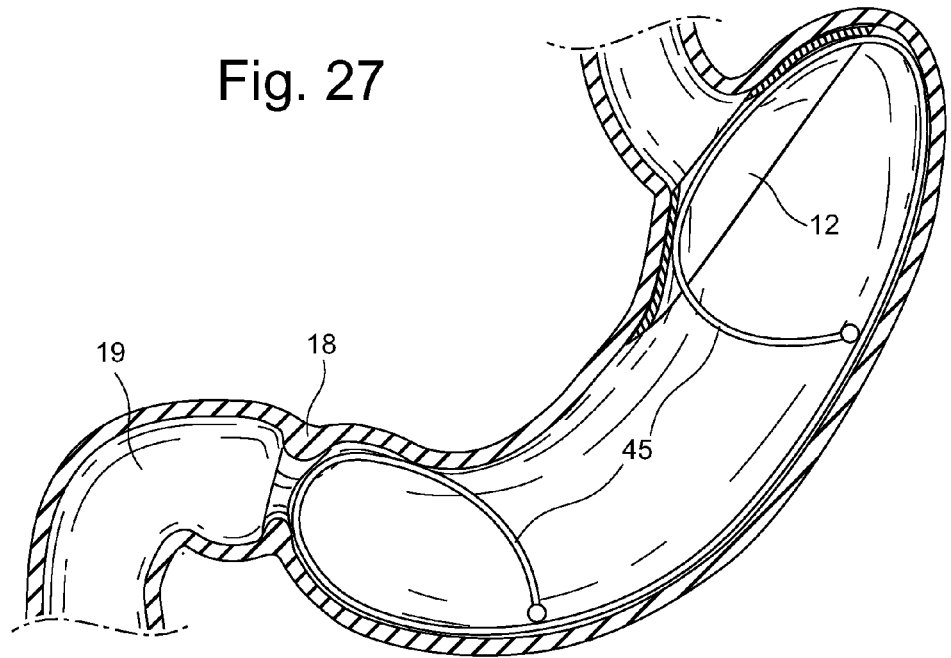
FIG. 27 depicts a side view of the embodiment of the present invention shown in FIG. 26, located within a cross-section of a stomach that is undergoing contraction due to peristalsis.

FIGS. 26 and 27 show an alternate embodiment of the two-element design where the positioning element 13 is a spring with open loop 45 where the loops 45 are allowed to flex as needed to maintain the relative position of the device 10 within the stomach. A mechanical stop for maximum compression is supplied by only allowing the spring to flex until the loop 45 has closed. This ensures that a minimum profile is maintained to prevent the device 10 from potentially migrating past the pyloric valve 18 and into the duodenum 19.

Figure 28:
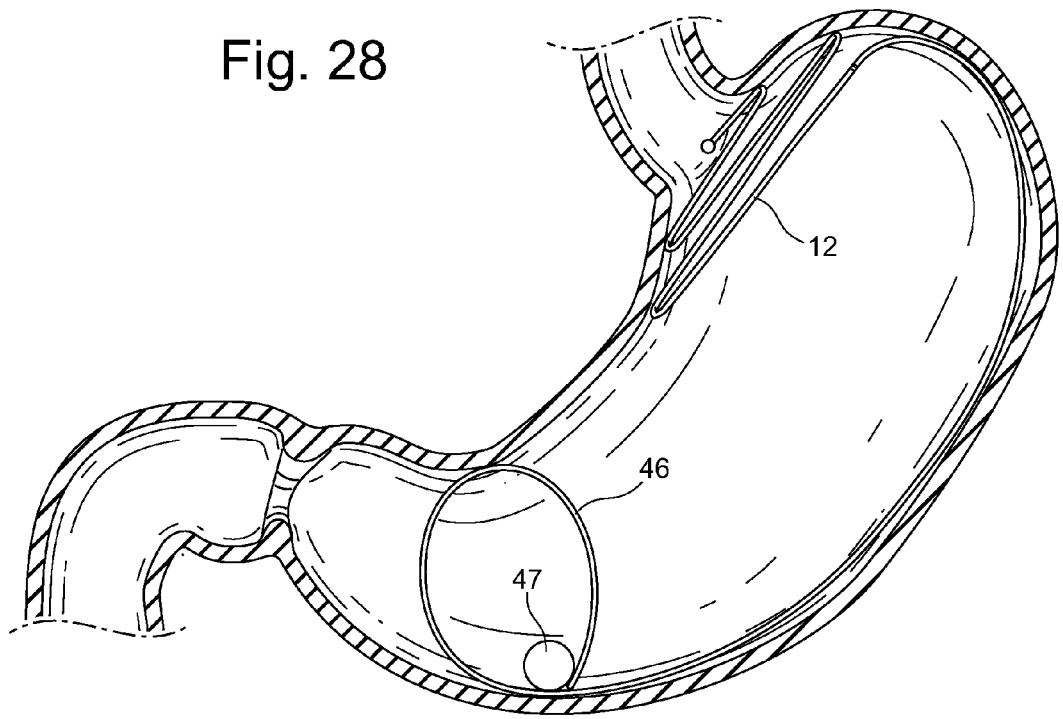
FIG. 28 depicts a side view of an embodiment of the bariatric device of the present invention, located within a cross-section of a stomach.
Figure 29:
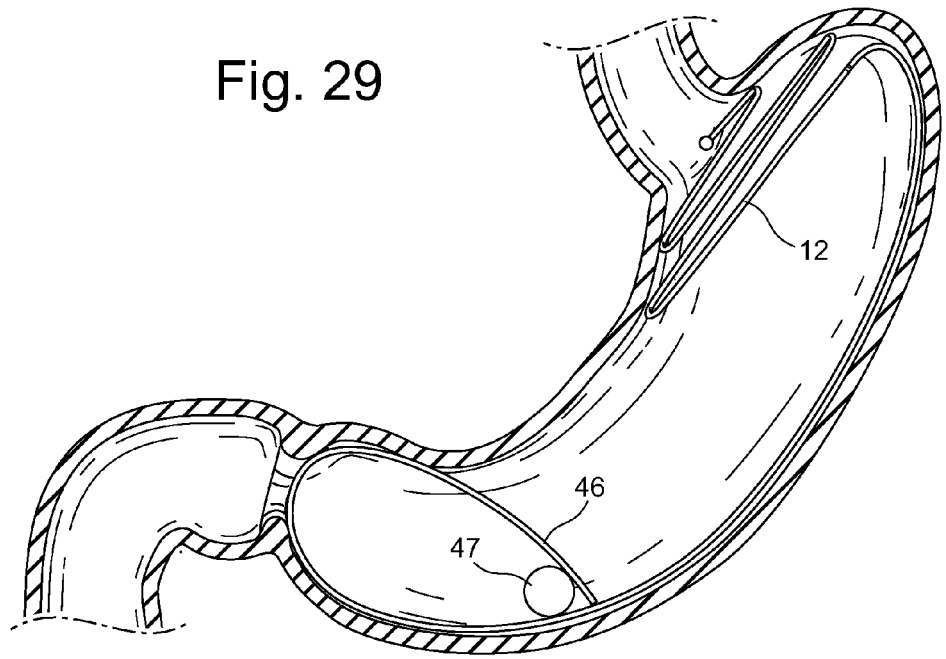
FIG. 29 depicts a side view of the embodiment of the present invention shown in FIG. 28, located within a cross-section of a stomach that is undergoing contraction due to peristalsis.

FIGS. 28 and 29 show another alternate embodiment of the two-element design where the cardiac element 12 is in the form of a spiral and the positioning element 13 is a closed loop 46. The closed loop 46 is allowed to compress as needed during peristalsis to maintain its relative position. This also shows a mechanical stop 47 that could be added inside the loop to prevent the loop from over flexing. The cardiac element 12 could also be a sphere as shown or ring as shown in other figures.

Figure 30:
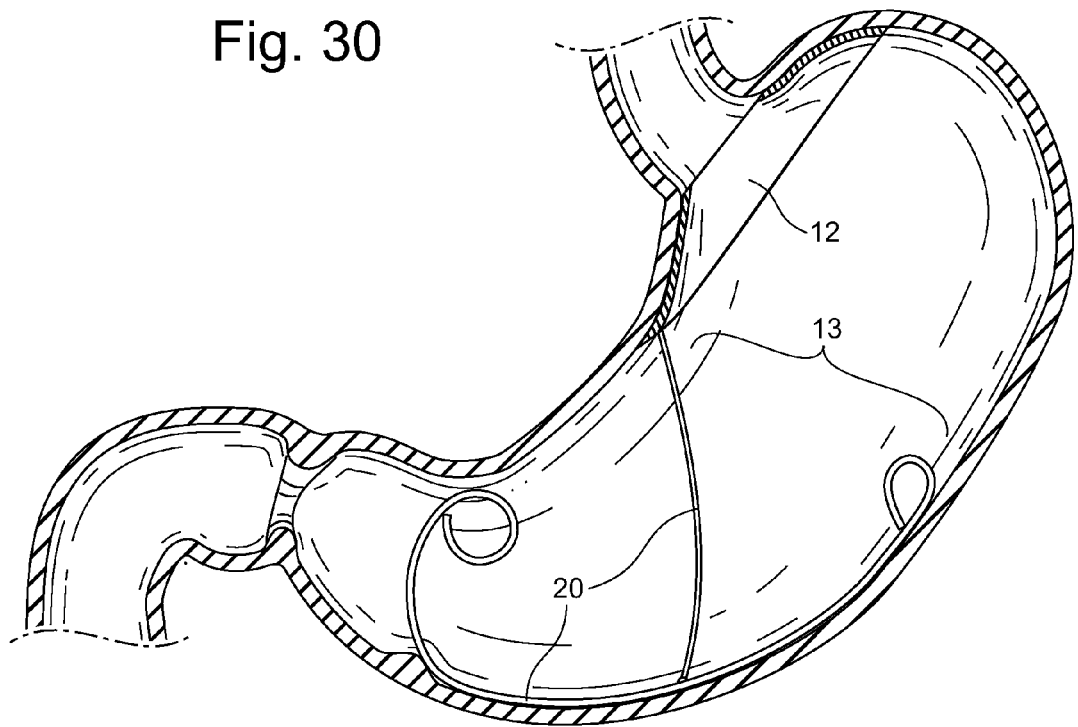
FIG. 30 depicts a side view of an embodiment of the bariatric device of the present invention, located within a cross-section of a stomach.

FIG. 30 shows a device 10 similar to one shown in FIG. 8A where the positioning element 13 contains two members 20. One member 20 could contain a loop that could intermittently engage the pyloric region 42 to prevent undue migration.

Figure 31:
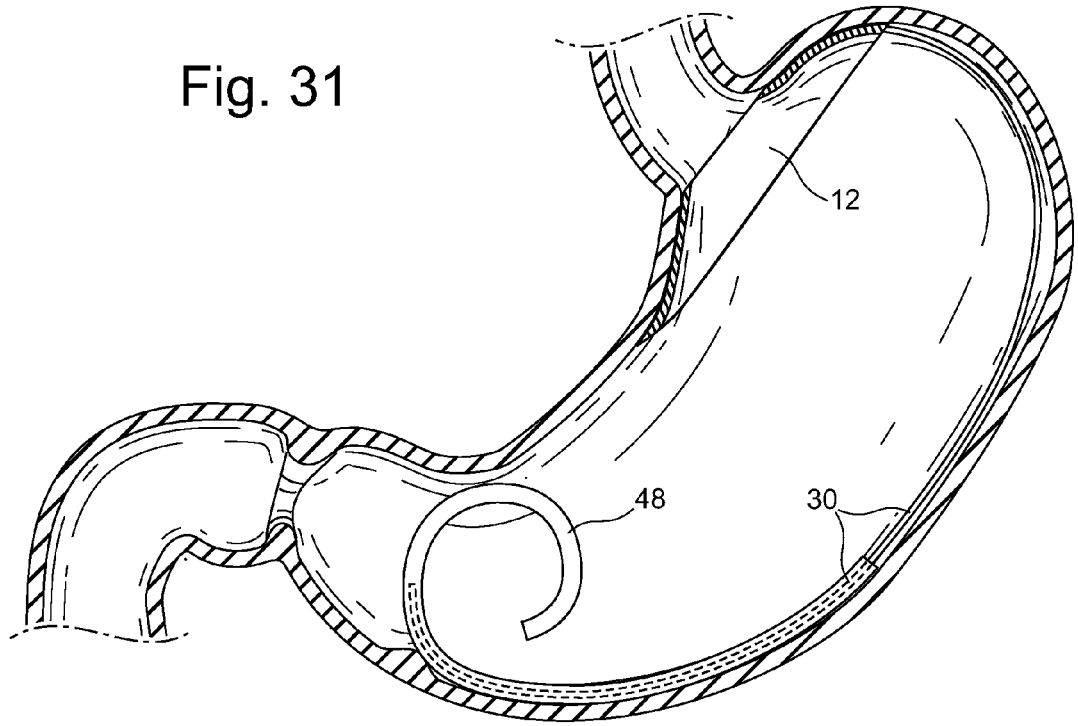
FIG. 31 depicts a side view of an embodiment of the bariatric device of the present invention, located within a cross-section of a stomach.

Another alternative to this design would be to have a connecting element 25 made up of two members 30 that can slide relative to one another to accommodate for stomach motion. See FIG. 31. This drawing shows how a flexible wire or ribbon, the connecting element 25, could fit inside of less flexible pre-curved pyloric element 48. As the stomach contracts, the connecting element 25 could slide or into the pre-curved pyloric element 48 to reduce the overall length during stomach contraction. Since the connecting element 25 would resist the permanent curvature, it would spring back out of the pre-curved pyloric element 48 to regain its length when the contraction was completed.

Another embodiment to accommodate for stomach contractions would allow the pyloric element 26 to flex and slide along the lower stomach region or pyloric region 42. In this embodiment, the pyloric element 26 and connecting element 25 could be combined into a single member. The pyloric element 26 could be a flexible ribbon with an open curve in the end. This curve could flex to create a closed loop which would allow the device 10 to slide within the lower stomach segment to maintain the position of the cardiac element 12 and not migrate beyond the pyloric valve 18.

In yet another embodiment, the connecting element 25 may be made up of two or more members 30. See FIGS. 32A and 32B. As shown in the drawing, the cardiac element 12 would contact the upper stomach or cardiac region 40, while pyloric element 26 contacts the lower stomach or pyloric region 42. The connecting element 25 has three members 30, which are shown as curved wires or ribbons. One member 30 curves to match the lesser curve 16 (LC), while two other members 30 curve to match a median line between the lesser and greater curve 17 (GC), and curve to contact the anterior and proximal surfaces of the stomach to maintain its position even during peristalsis. FIG. 32A shows an optional location for the pyloric element 26 in the pyloric region 42. FIGS. 33A and 33B shows a similar embodiment with another optional location for the pyloric element 26 closer to the pyloric valve 18.

In another embodiment, peristaltic motion may cause the device 10 to move inside the stomach and could cause the pyloric element 26 to slide from the relative locations such as those shown in FIGS. 34A, 34B and 35. These drawings show a three-element embodiment where the connecting element 25 may have four members 30. FIGS. 34A, 34B and 35 depict a similar embodiment to FIGS. 33A and 33B, but with an additional element to match the greater curve 17. During peristalsis, the greater curve 17 will shorten, and the member 30 that matches could curve inward to a convex form. After the peristaltic action is complete, the member 30 may spring back to its original concave form. Using these concepts, additional members 30 for the connecting element 25 may be used beyond the three and four members 30 described here, and could be located in a variety of locations along the midline, lesser curve 16 or greater curve 17 or any combination.

Figure 36A:
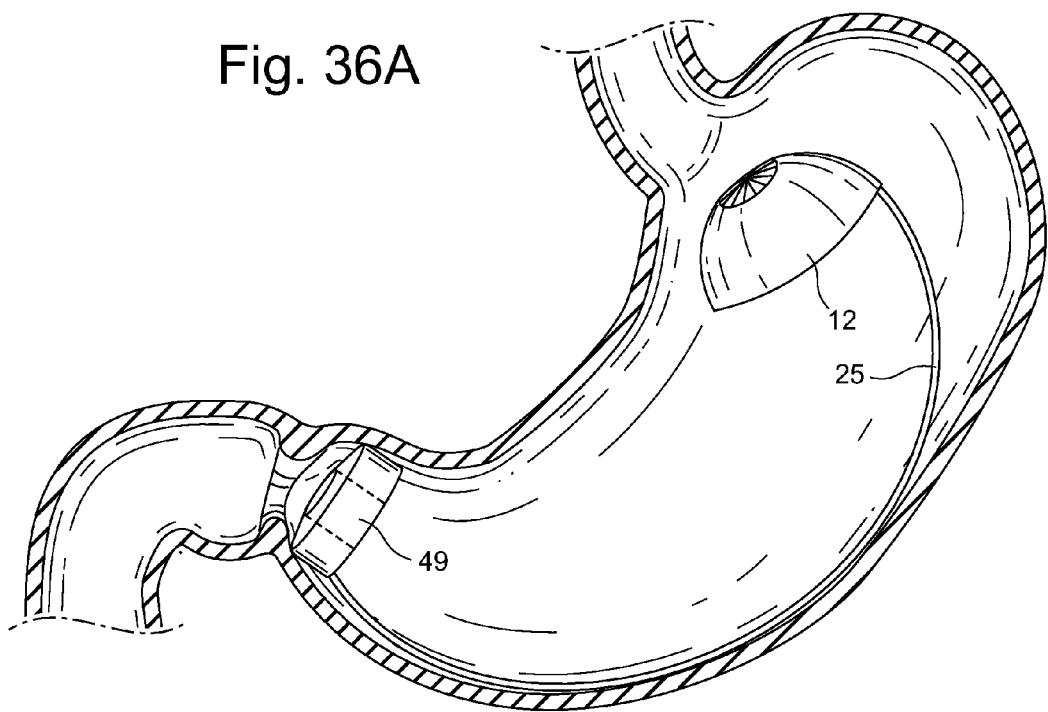
FIG. 36A depicts a side view of an embodiment of the bariatric device of the present invention, located within a cross-section of a stomach.
Figure 36B:
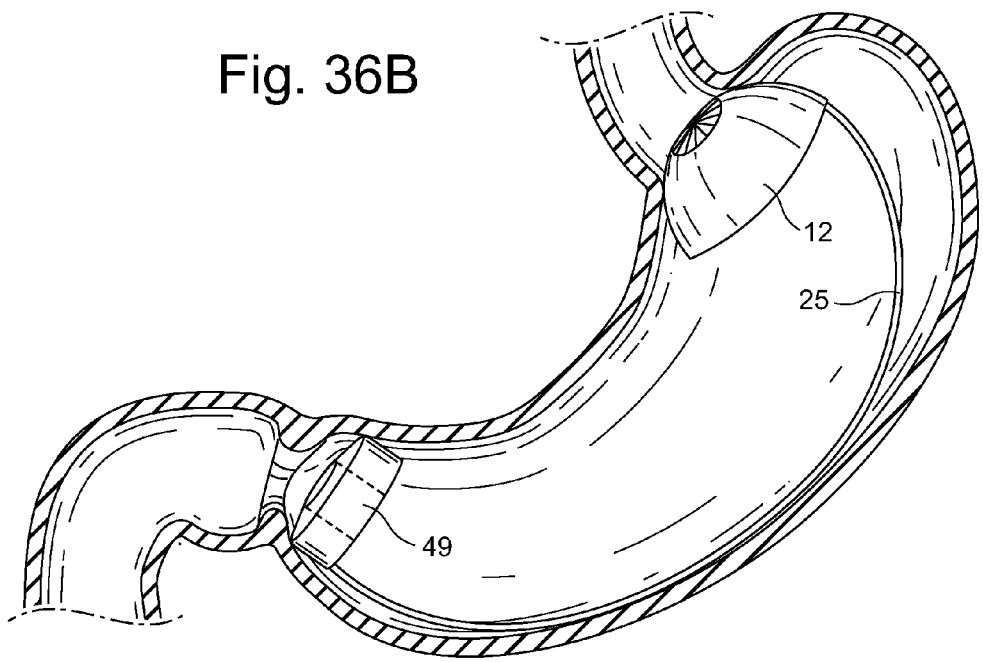
FIG. 36B depicts a side view of the embodiment of the present invention shown in FIG. 36A, located within a cross-section of a stomach that is undergoing contraction due to peristalsis.

FIGS. 36A and 36B depict an embodiment where the cardiac element 12 may be allowed to intermittently contact the upper stomach during peristalsis. The pyloric element may be a rigid or semi-rigid ring 49 and the connecting element 25 may be a spring to connect to the cardiac element 12. In this embodiment, the ring 49 could engage the lower stomach at a fixed diameter when the stomach is at rest. Compression of the stomach during peristalsis would push the ring 49 towards the upper stomach to allow the cardiac element 12 to intermittently contact the upper stomach and/or cardiac area 40. This may be advantageous to prevent overstimulation of the upper stomach or for other purposes.

Figure 37A:
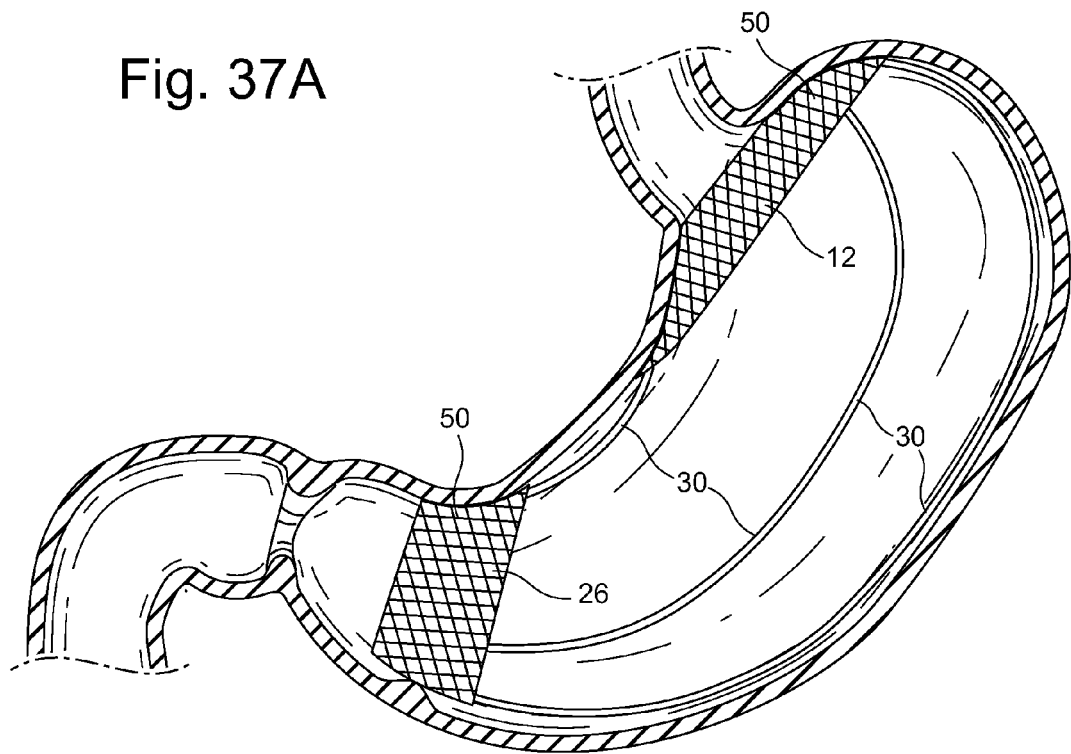
FIG. 37A depicts a side view of an embodiment of the bariatric device of the present invention, located within a cross-section of a stomach.
Figure 37B:
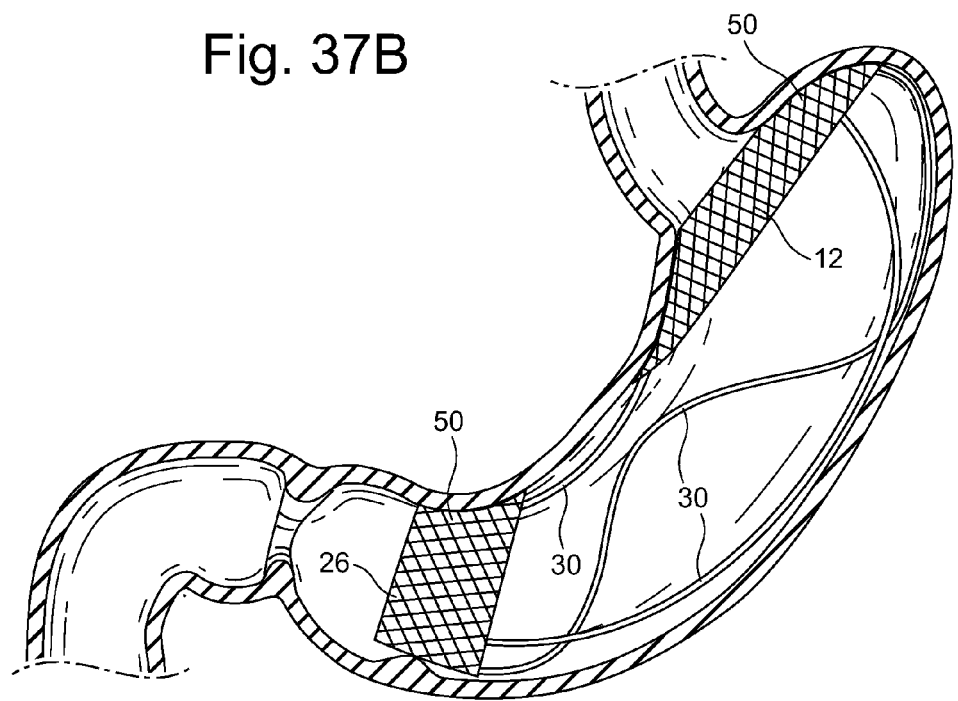
FIG. 37B depicts a side view of the embodiment of the present invention shown in FIG. 37A, located within a cross-section of a stomach that is undergoing contraction due to peristalsis.

In yet another set of embodiments, the bariatric device 10 in either the two- or three-element embodiments may be self expanding. FIGS. 37A and 37B depict an alternative embodiment where the cardiac and pyloric elements 12, 26 are self expanding. These elements could be self expanding or have a portion that is self expanding to allow the device 10 to flex with peristalsis, but maintain tension to spring open to apply pressure or contact and position within the stomach. The self expanding portion could be made of Nitinol, silicone, polyurethane, Teflons, stainless steel or other suitable materials or combinations of suitable materials. FIGS. 37A and 37B shows a Nitinol wire mesh pattern 50 applied to a frusto-conical shape to create a shell. The Nitinol wire may act as a stiffening member within the cardiac and pyloric elements 12, 26. The Nitinol wire could be arranged in many different patterns to allow for the appropriate amount of self expansion while allowing the element to compress during peristalsis. The array pattern could include circular arrays, angular arrays, linear arrays, or other suitable arrays. The pattern could be woven or a continuous spiral.

The self expanding function may also assist in deployment by allowing the device 10 to compress and then regain its shape. A preferred method of deployment is to compress the bariatric device 10 into a long narrow shape, which is then placed in a deployment tube, sheath or catheter. The collapsed and encased device 10 is then guided down the patient's esophagus 32 and into the stomach, where the bariatric device 10 is released from the deployment tube or catheter. Once released, the device 10 would expand to its original operational shape. The stiffening member, such as Nitinol wire, may provide adequate stiffness to expand the elements into their operational shape, and maintain that general shape during operation, while allowing flexibility to accommodate peristalsis.

The embodiment depicted in FIGS. 37A and 37B show the cardiac and pyloric elements 12, 26 connected by a connecting element 25 with multiple curved members, which are shown to be a wire mesh array 50, but could be made of Nitinol wire, silicone, teflon another suitable material, or a combination of these materials. The four members of the connecting element 25 have different lengths to allow for proper alignment and seating within the stomach. FIG. 37B depicts how during peristalsis, the stomach will contract and its profile will reduce. The bariatric device 10 may shift and flex within the stomach, but the self expansion feature allows it to spring open and maintain its general position correctly. The connecting element 25 could have a pre-curved bend to form a living hinge to direct where the element to flex during peristalsis as shown in 37B.

As shown in FIGS. 37A and 37B, a preferred embodiment of the cardiac element 12 may be a substantially flattened frusto-conical shape, defining a substantially circular opening that is adapted to correspond to the esophageal/cardiac opening of a stomach. Those figures also show that a preferred embodiment of the pyloric element 26 may be a steep frusto-conical shape, or a tapered cylinder, which is adapted to fit the pyloric region 42 of the stomach, and preferably sized so that it does not migrate past the pyloric valve 18. As discussed above, these elements may have a wide variety of shapes or may be inflatable, and these are only examples The four connecting members may be constructed from 2 full loops or 2 loops connected together to create a "FIG. 8" structure. The loops could be contoured to generally follow the curves of the stomach, and could be connected to the pyloric and cardiac elements 26, 12 in a variety of locations. The loops could be oriented to intersect at a variety of locations to provide different configurations with varying structural resistance and flexure points. For example, FIGS. 38A and 38B depict a bariatric device 10 where there are 2 separate closed loops 51 and the loops 51 are crossed in the pyloric element 26 so that the wires do not obstruct the distal opening of the element. The loops 51 are then aligned in a parallel pattern where they are attached to the cardiac element 12. This allows the cardiac element 12 to follow the contours of the loops 51 even when the device 10 is laid flat and the loops 51 are compressed together as could be the case inside the stomach. This could allow for more uniform curved contact of the cardiac element 12 with the cardia 40 and adjacent fundus 41. The parallel orientation of the loops 51 along the cardiac element 12 would provide less resistance of the device 10 just below the GE junction for a more gentle response.

Figure 39A:
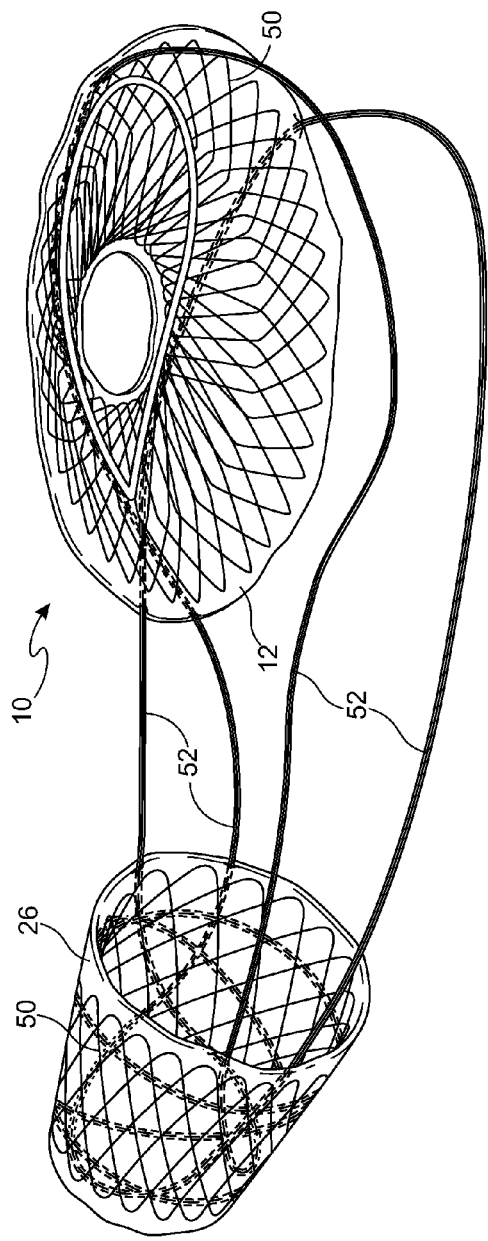
FIG. 39A depicts an underside perspective view of an embodiment of the bariatric device of the present invention.
Figure 39B:
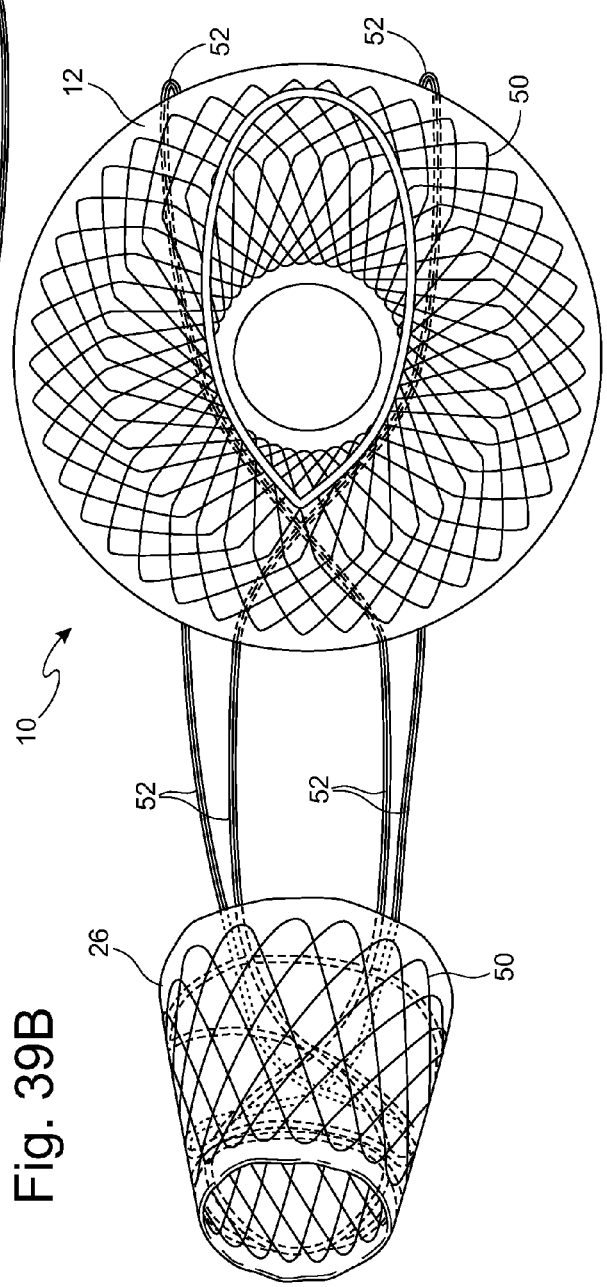
FIG. 39B depicts a top view of an embodiment the bariatric device of the present invention of the present invention.

In another embodiment, the 2 loops 52 are connected in a "FIG. 8" pattern where the loops are 52 crossed in the pyloric element 26 and do not obstruct the distal opening of the pyloric element 26. See FIG. 39. The loops 52 cross again just below the opening of the cardiac element 12, which allows the cardiac element 12 to flare more when the device 10 is laid flat and the loops 52 are compressed together such as could be the case inside the stomach. This could allow for more focused, linear contact of the cardiac element 12 with the cardia 40 and adjacent fundus 41 in the stomach. The cross of the loops 52 below the opening of the cardiac element 12 would provide more structural strength of the device 10 just below the GE junction 38 for more acute response. To increase the acute response, a stiffening member such as a wire loop or other could be added cardiac element 12 to direct stiffness in a desired area. FIG. 39 shows one possible orientation for a stiffening member, but other orientations, shapes and additional members could be added to generate a specific response.

Where the connecting element 25 is formed from loops, the loops could be formed from Nitinol wire and then coated in an acid-resistant coating 53 such as silicone or silicone covering. These loops could also be made of stainless steel, teflons or other suitable materials or combinations of materials. The loops could be closed or connected in a variety of ways. For the example of Nitinol, the loops could be closed by a glue joint where the wire loop ends are glued inside of another tube. They could also be closed by a crimping, swaging, or welding. The loops could also be left open, if a feature is added for adjustability and it is preferred to have the loops open with both ends fixed to the elements as needed.

The contact members of the elements may be comprised of a variety of materials. For example, the Nitinol wire pattern of the cardiac, pyloric, and or connecting and/or positioning elements 12, 26, 25, 13 may be exposed for direct contact with the stomach or the wire could be covered or sealed in another material, such as silicone, PTFE, polyurethane or other suitable materials. For example, FIG. 40A depicts a pyloric element 26 where the wire mesh 50 is covered in another material to create a smooth surface for the contact member 54 to facilitate sliding within the stomach. Alternatively, FIG. 40B shows the wire exposed to the stomach mucosa surface. This shows how the wire array 50 could be arranged and formed to add a wavy pattern to increase to profile of the wire above the element's nominal surface, which in this case is shown as a cone with the wire protruding above the cones surface. This would allow the wire to act as a macro texture surface for the contact member 54 to grip the stomach surface to reduce sliding or it could provide a macro texture for tissue ingrowths. The Nitinol may be treated with a surface finish, passivation or coating to improve its acid resistance within the stomach.

The contact and stiffening members of the elements may be separate, entirely integrated, or both. For example, if a cardiac element 12 is made entirely of Nitinol wire, the wire acts as both a contact member and a stiffening member. The same would apply if an element were made entirely of silicone; the silicone would act as both a stiffening and contact member. In another embodiment, where Nitinol wire is embedded in another material such as silicone, the Nitinol wire acts as a stiffening member and the silicone acts as a contact member. In another embodiment, the Nitinol wire may be partially exposed and partially covered by the silicone (and/or on the interior of the element), in which case the Nitinol wire acts as both a stiffening and contact member. In certain embodiments, the combination of materials may act as a stiffening member. For example, an embodiment where the contact member is silicone with Nitinol wire embedded, the silicone may act in conjunction with the Nitinol to provide more stiffness than the Nitinol could achieve alone. Various combinations of stiffening and contact members may be apparent to those skilled in the art.

Yet another embodiment with self expanding features is depicted in FIG. 41. In this embodiment, the cardiac, pyloric, and connecting elements 12, 26, 25 are all combined into a single unit, which contours to follow the general shape of the stomach but designed to maintain outwardly biasing pressure at upper and lower stomach regions. The self expansion feature will allow the device 10 to flex and give during peristalsis, but would allow the device 10 to spring open to maintain its position and function. The wire array 55 could be designed to encourage more expansion in one area than in another, or be stiffer in one area or another, to further improve the function of the device 10.

Figure 42B:
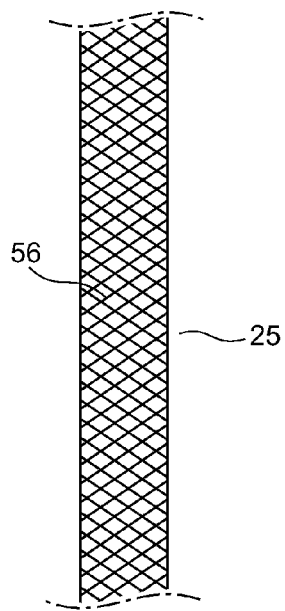
FIG. 42B depicts a side view of a connecting element of an embodiment of the present invention.
Figure 42C:
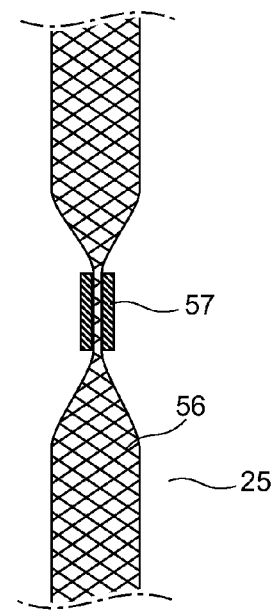
FIG. 42C depicts a side view of a connecting element of an embodiment of the present invention.
Figure 42D:
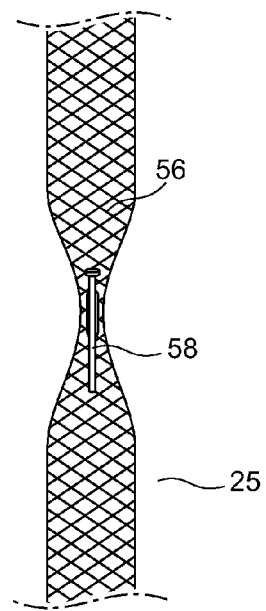
FIG. 42D depicts a side view of a connecting element of an embodiment of the present invention.

Yet another embodiment with self expanding features is depicted in FIG. 42A, where the cardiac, pyloric, and connecting elements 12, 26, 25 all have self expanding portions. The cardiac and pyloric elements 12, 26 are generally frusto-conical in shape and contain a Nitinol wire pattern 50 for radial and longitudinal expansion. The connecting element 25 is also self expanding and connects the cardiac and pyloric elements 12, 26. The connecting element 25 can compress and expand to maintain and appropriate amount of pressure on the upper and lower stomach and to maintain the device 10's position. The connecting element 25 could be just a bare Nitinol wire array 50 or it could be covered with silicone or other suitable material(s). As described for previous embodiments, the connecting element 25 could match the greater or lesser curve 16, or go down the center of the stomach or be a combination of both. Covering the device 10 with another material could constrain the compressibility of the length of the device 10, which may be desirable in order to achieve pressure and/or contact at various portions of the stomach. There may also be another member down the center of the Nitinol tubular array 56 to increase stiffness and to adjust the length. FIG. 42B shows the connecting element 25 made up of a wire array 56 at rest. FIGS. 42C and 42D show how the length of this element 25 may be adjusted to elongate the length. Adjustability of the length would allow the device 10 to be adjusted to custom fit the device 10 to the patient. FIG. 42C shows how an additional ring or feature 57 could be applied to the outside of the tube to reduce the diameter and increase the length. FIG. 42D shows how a pin or clip 58 may be placed inside the mesh array 56 to increase the length which subsequently would reduce the diameter. These adjustability features could be applied to any of the self expanding features.

Figure 43:
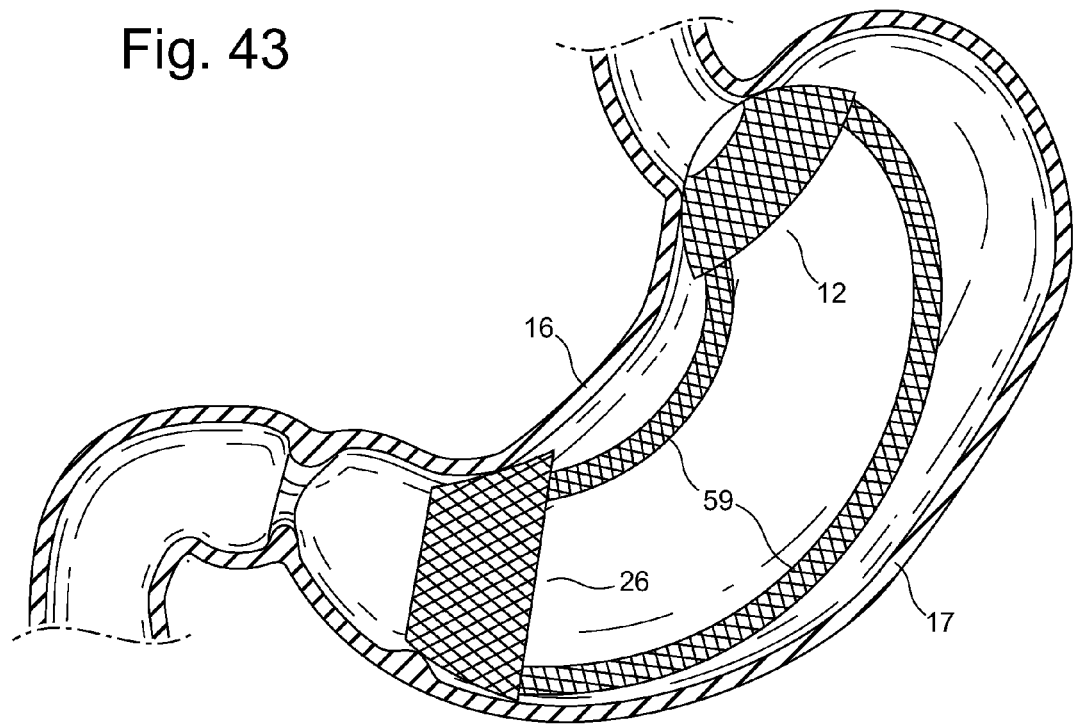
FIG. 43 depicts a side view of an embodiment of the bariatric device of the present invention, located within a cross-section of a stomach.

FIG. 43 shows a similar embodiment to above but shows that the connecting element 25 could contain multiple self expanding members 59. This figure shows one member 59 along the lesser curve 16 and two members 59 along the midline between the lesser and greater curves 16, 17, which contact the anterior and posterial surfaces of the stomach walls. These could all contain expansion features as mentioned above. Although FIG. 43 depicts three members 59 in the connecting element 25, it could contain two, four, or any number of members. These members could match the lesser curve 16, greater curve 17, stomach midline or all any combination of these.

As mentioned above, a preferred device 10 has adjustability or adaptability to match any changes in the patient over time. A variation of the above embodiments would be to allow the device 10 to be adjustable via an adjustment element 60. This adjustability could be in the length, shape, angle or stiffness of the cardiac, pyloric, connecting, and/or positioning elements 12, 26, 25, 13.

The bariatric device 10 could be adjustable to allow for adjustment at the time of placement or could be adjusted at a later time. This adjustability could be achieved by having a variable spring tension in one of the elements to allow the device 10 to extend, contract, or distort as needed. It could also be achieved by adding an expansion joint 75 in a member to elongate or compress as needed. This expansion could be a manual adjustment performed by the physician in the office through a gastroscopic procedure. This expansion could be achieved by various mechanisms, including but not limited to those operated by: rotating a threaded member, ratcheting backwards or forwards, a hydraulic mechanism, a pneumatic mechanism, a cam, a tension mechanism, a telescoping mechanism or other elongation or contraction mechanisms. The outer surface of the connecting element 25 and/or positioning element 13 is preferably smooth with rounded or gently angled edges to prevent irritation of the stomach during peristalsis, although sharp angles may be preferred in some applications. To create a smooth interface, these elements could be encased in a sleeve or sheath that could be removed or remained fixed during the expansion. A sheath may not be required if the expansion joint 75 is designed with smooth contours on its own.

Manual Actuation

The device 10 could also be adjusted by manual means inside the stomach by using a gastroscopic instrument to come into direct contact with the device 10.

The instrument could also act as a pusher or puller to activate a pulley mechanism or a clipping mechanism. For example, the positioning and/or connecting element 13, 25 could be a ratchet or strut with multiple positional features such as holes, grooves, teeth or wedging action. The device 10 could have a feature to engage the ratchet teeth or positional features such as a pin or clip or other. The instrument could retract the pin or compress the clip and then reposition this feature in the next available location.

In another embodiment, the members of the connecting element 25 could have multiple beads or spheres 62 that are captured by a cuff or ring retainer on the cardiac element 12. An instrument could be used to expand the cuff to pull the bead through for positioning. Similarly, the cuff could have a keyway retainer feature that allows the bead to only fit through a specific location and then lock into position where the beads connect to the wire or ribbon or tube.

Figure 44A:
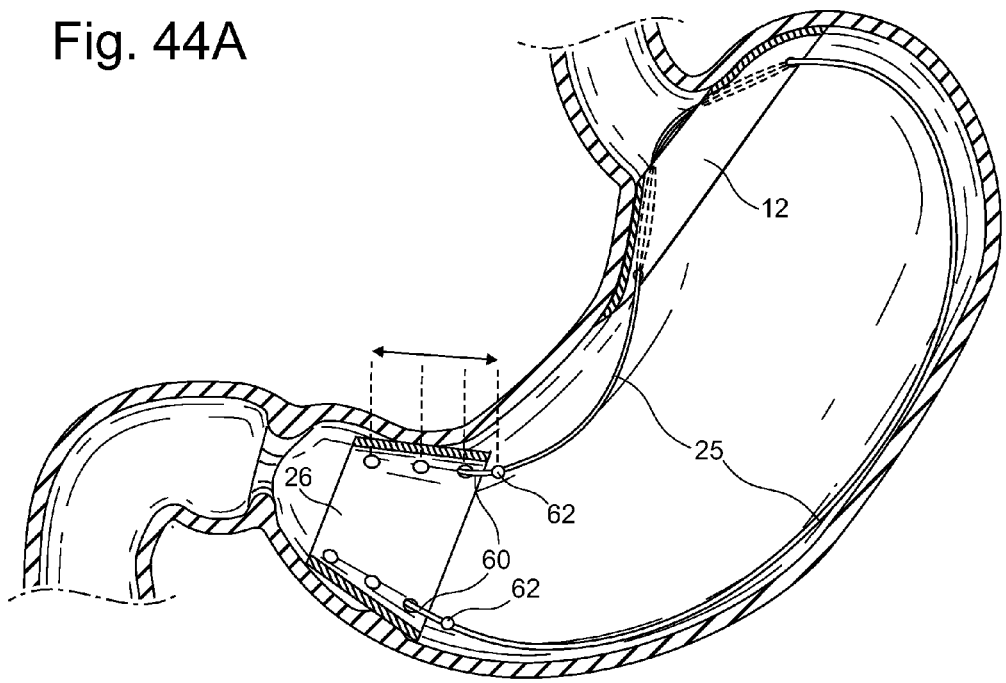
FIG. 44A depicts a side view of an embodiment of the bariatric device of the present invention, located within a cross-section of a stomach.
Figure 44B:
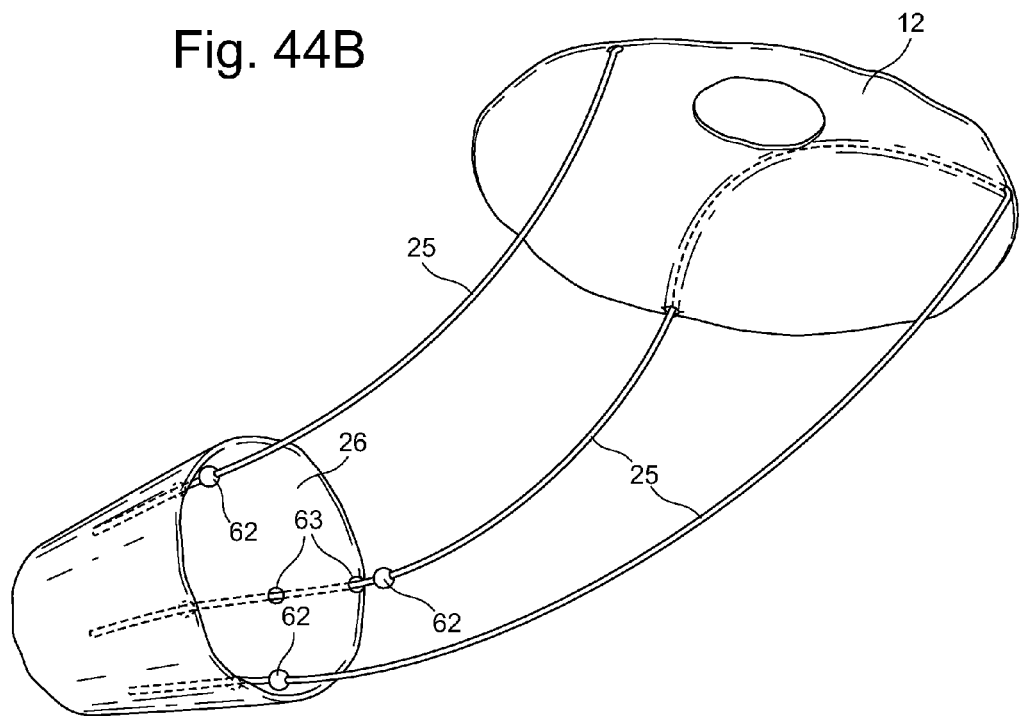
FIG. 44B depicts an underside perspective view of an embodiment of the present invention.
Figure 45A:
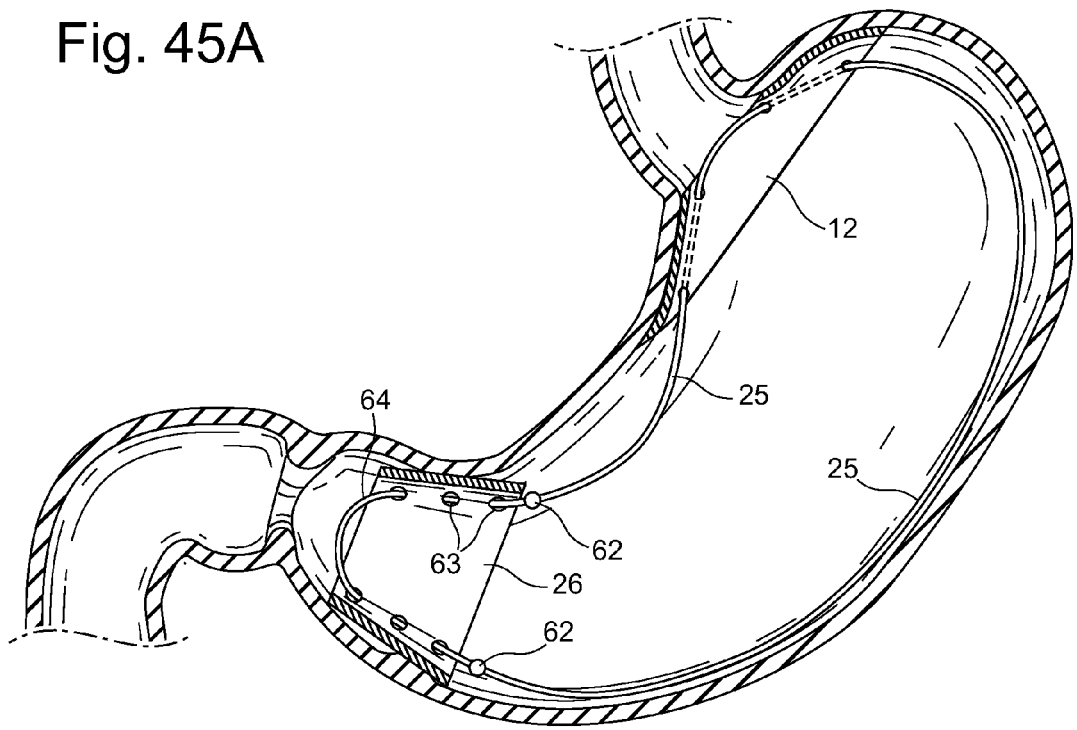
FIG. 45A depicts a side view of an embodiment of the bariatric device of the present invention, located within a cross-section of a stomach.
Figure 45B:
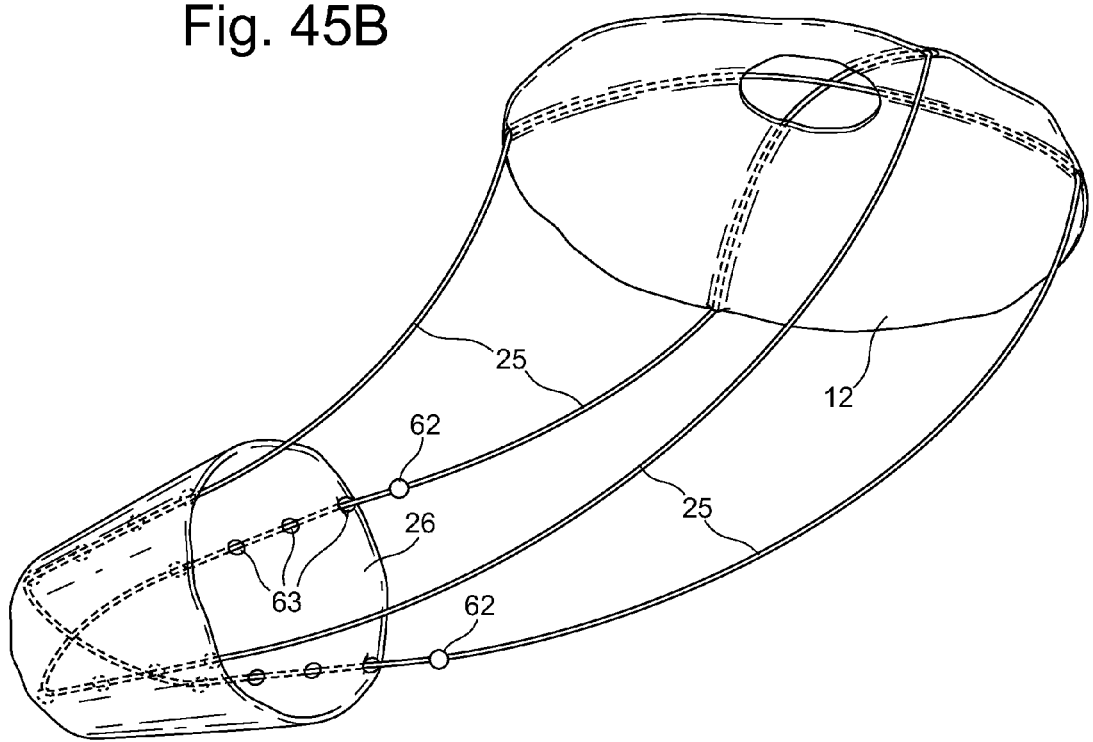
FIG. 45B depicts an underside perspective view of an embodiment of the present invention.
Figure 46A:
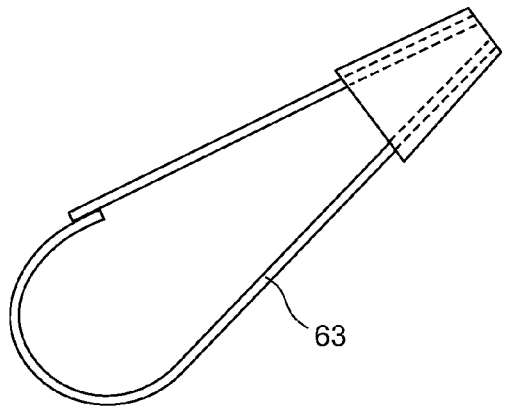
FIG. 46A depicts a side view of strap retainer of an embodiment of the present invention.
Figure 46B:
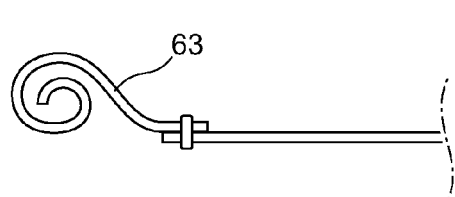
FIG. 46B depicts a side view of strap retainer of an embodiment of the present invention.
Figure 46C:
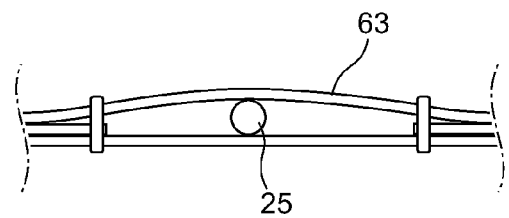
FIG. 46C depicts an end view of strap retainer of an embodiment of the present invention.
Figure 46D:
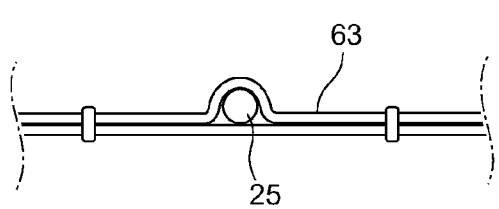
FIG. 46D depicts an end view of strap retainer of an embodiment of the present invention.
Figure 46E:
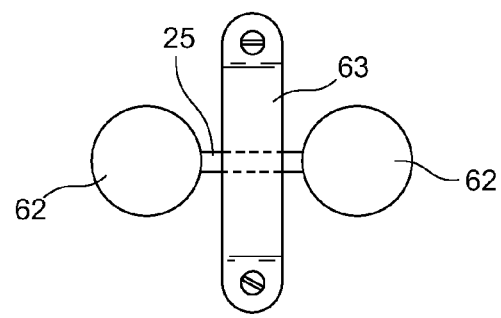
FIG. 46E depicts a top view of strap retainer retaining a member with two positional beads of an embodiment of the present invention.

FIGS. 44A and 44B, shows a similar feature in the pyloric element 26 where the adjustment element 60 is a single wire. FIGS. 45A and 45B shows an adjustment element 60 in the pyloric element 26 where there could be a full loop 64 that has expansion features on both sides of the loop 64. These features could be beads or clips 62 that can be pulled through a mechanical feature such as a hole or strap retainer 63 and held in place. FIGS. 46A, 46B, 46C, 46D, and 46E show side views and top views of optional retaining features 63 that allow for expansion to let a bead or arrowhead 62 pass, but then close to hold the feature in position.

FIGS. 47A, 47B, 47C and 47D shows several examples of compressible clips 65 acting as a "bead" or positional feature that could be used for adjustability. For example a retainer strap 63 of silicone could be bonded on both sides to create a narrow passageway 66 where the clip 65 could be placed in the compressed position, and then expand open after passing through the strap 63 to maintain its position. Several straps 63 could be bonded in a row to create several positional locations. FIGS. 47B and 47D shows the clip 65 in is open, relaxed state, where 47C shows the clip 65 in a compressed state where it can pass through the retainer strap 63.

Figure 48:
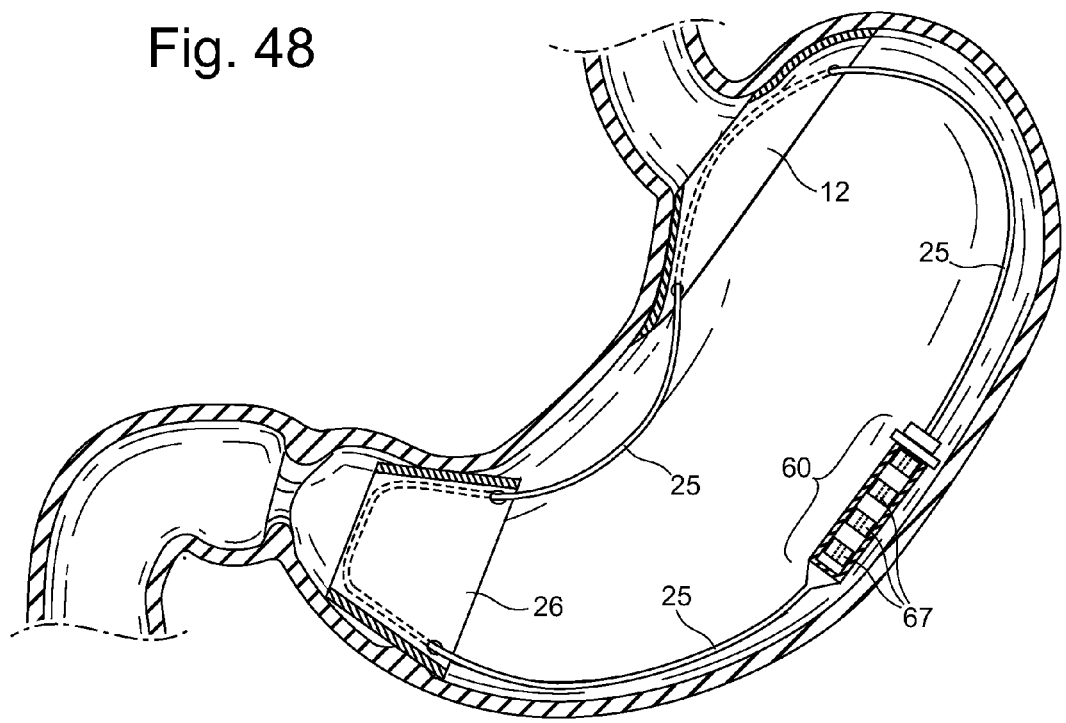
FIG. 48 depicts a side view of an embodiment of the bariatric device of the present invention, located within a cross-section of a stomach.
Figure 49A:
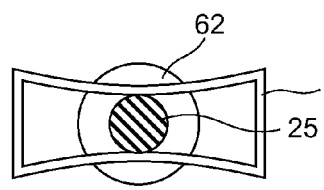
FIG. 49A depicts an end view of a retainer clip in a relaxed and closed state, and a bead on a member shown in cross section, of an embodiment of the present invention.
Figure 50A:
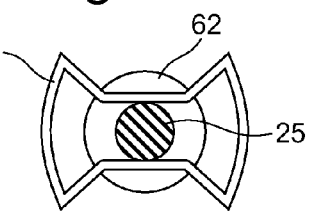
FIG. 50A depicts an end view of a retainer clip in a relaxed and closed state, and a bead on a member shown in cross section, of an embodiment of the present invention.
Figure 51A:
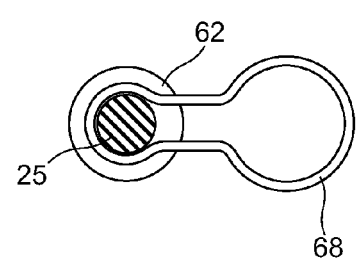
FIG. 51A depicts an end view of a keyway, and a bead on a member shown in cross section, of an embodiment of the present invention.
Figure 49B:
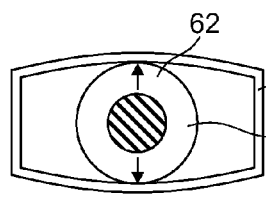
FIG. 49B depicts an end view of a retainer clip shown in FIG. 49A in a compressed and open state, and a bead on a member shown in cross section.
Figure 50B:
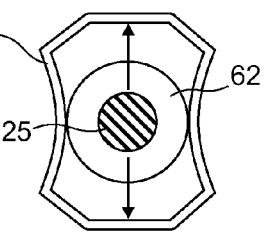
FIG. 50B depicts an end view of a retainer clip shown in FIG. 50A in a compressed and open state, and a bead on a member shown in cross section.
Figure 51B:
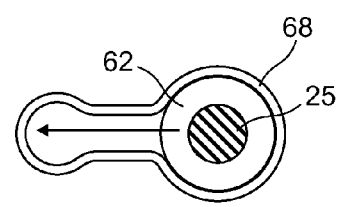
FIG. 51B depicts an end view of a keyway shown in FIG. 51A, and a bead on a member shown in cross section that has translated its position relative to FIG. 51A.

FIG. 48 shows an adjustment element 60 with another option for adjustability where one or more compressible clips 67 are added to one of the connecting element members which has several positional locations. A clip retainer fixed to one side of the connecting element 25 could be compressed to open the clip 67 and then advance it over the positional features such as a bead 62, and then allow it to spring closed to fix the location of the device 10. FIGS. 49A and 50A show the clips 67 in their relaxed, closed positions where 49B and 50B show the clips 67 in their compressed, open positions sufficient to let the bead 62 pass. FIGS. 51A and 51B show options for a keyway for translational adjustability.

Figure 52A:
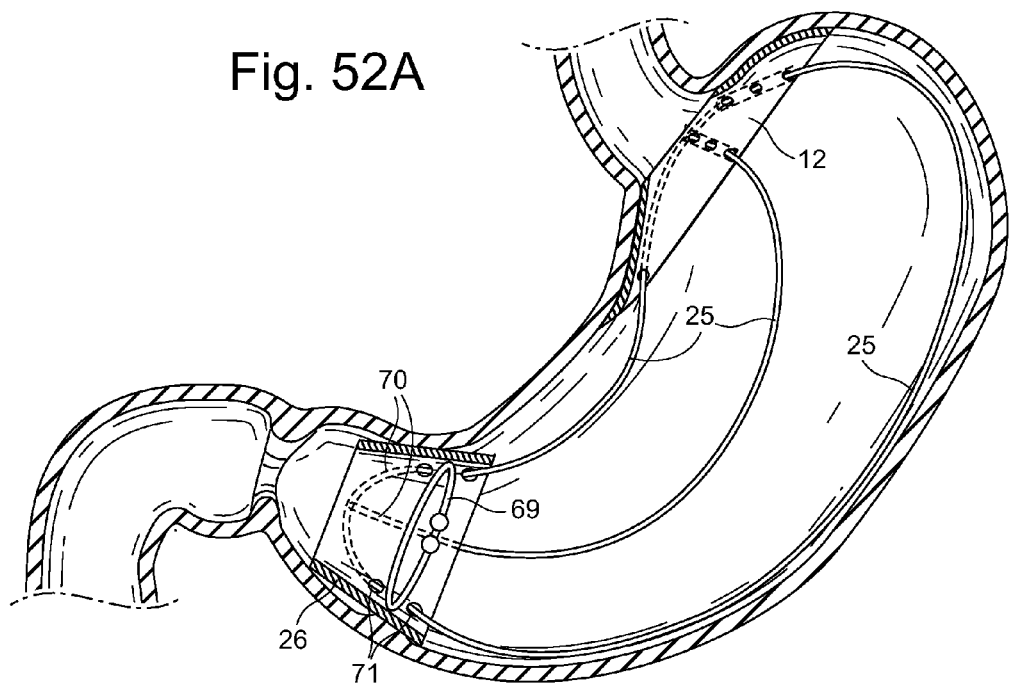
FIG. 52A depicts a side view of an embodiment of the bariatric device of the present invention, located within a cross-section of a stomach.
Figure 52B:
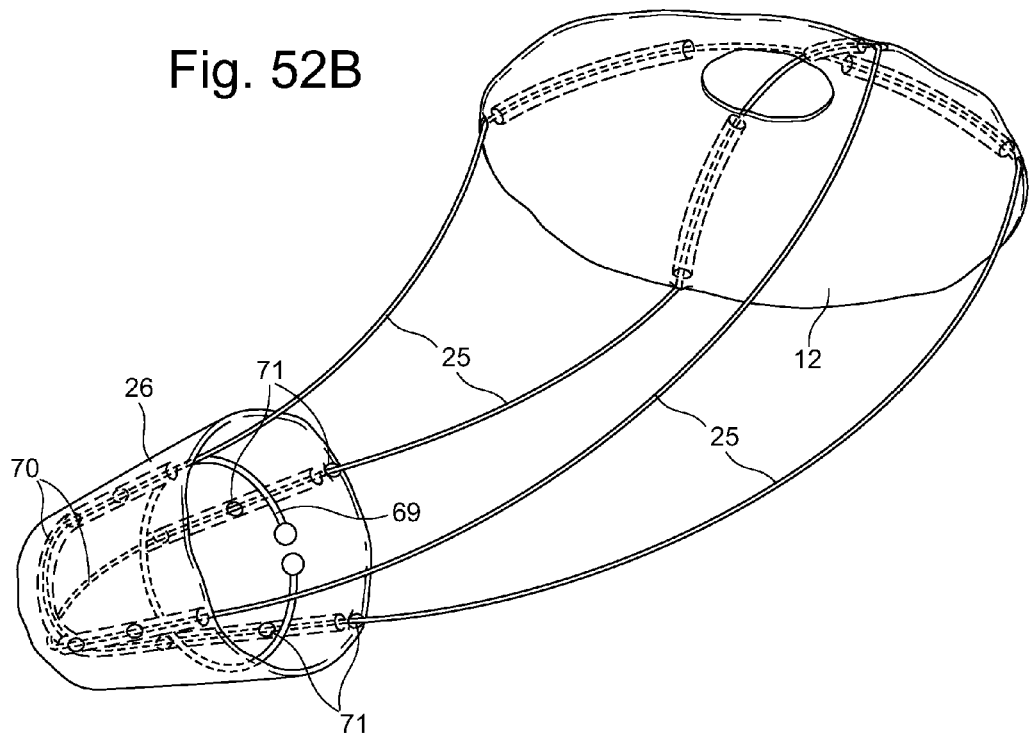
FIG. 52B depicts an underside perspective view of an embodiment of the present invention.

FIGS. 52A and 52B depict another option for adjustability where a locking ring 69 is used to fix the location of the connecting loops 70 into the pyloric element 26. The pyloric element 26 could have several positional features 71 connected to it. The loop 70 could also have several positional features 72 attached to it. When the positional features of the pyloric element 72 and connecting loop 70 are aligned, a locking ring 69 could be placed inside to hold the position of the elements together and to alter the length of the whole device 10 to be longer or shorter. In another embodiment shown in FIGS. 53 and 54, the ring 69 could be fixed to the pyloric element 26 and compressed to capture the positional features 72 located along the connecting element 25.

In another embodiment, an instrument could act as a screw driver to rotate a member to thread the two elements 73 closer or farther apart. See FIG. 55.

Figure 56:
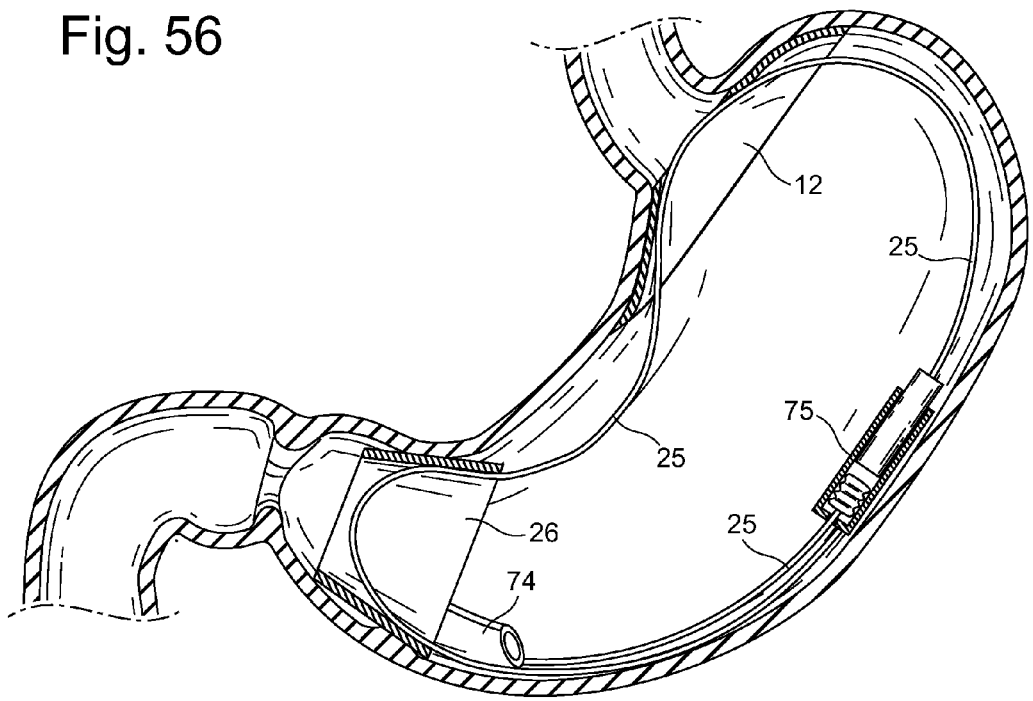
FIG. 56 depicts a side view of an embodiment of the bariatric device of the present invention, located within a cross-section of a stomach.

The instrument could also have a needle to inject fluid into an inflation element 74. Such an element may be a self sealing membrane to increase or decrease the length, diameter or stiffness through positive displacement of an expandable body. The self sealing membrane could be an injection port or it could be a self sealing surface on the expandable body, or the entire expandable body could be comprised of a self sealing surface. In all descriptions below, the term inflation element 74 can also refer to an injection port or to an area on the expandable body with a self sealing membrane. The self sealing membrane could also be a self sealing valve which can be accessed by a blunt needle or tube to allow access to add or remove fluid. FIG. 56 shows an inflation element 74 fixed to the pyloric element 26 or the connecting element 25. This valve or port could be connected by a fluidic path to an expandable body such as a sealed inflatable body inside of an expansion joint 75 such as a piston and cylinder. The valve could be accessed by an endoscopic instrument with a blunt end, while an injection port could be accessed by an endoscopic instrument with a non-coring needle where saline or other suitable fluid could be injected or removed from the port which would allow the inflatable body to expand or contract to control the length of expansion. Although this figure shows one expansion joint 75, the device 10 could contain one or more with a manifold set up to deliver fluid from the port to all of the expansion joints. In an alternative embodiment, the system could also have an expandable body such as a syringe type joint which would not require a sealed internal inflatable body.

Figure 57:
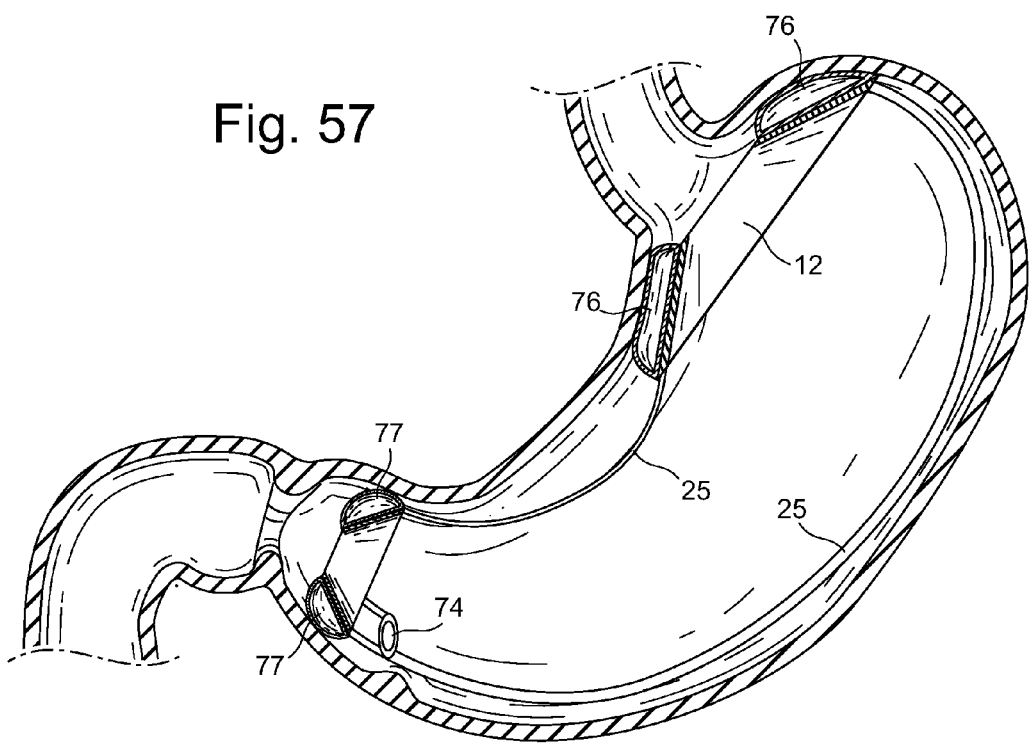
FIG. 57 depicts a side view of an embodiment of the bariatric device of the present invention, located within a cross-section of a stomach.
Figure 58A:
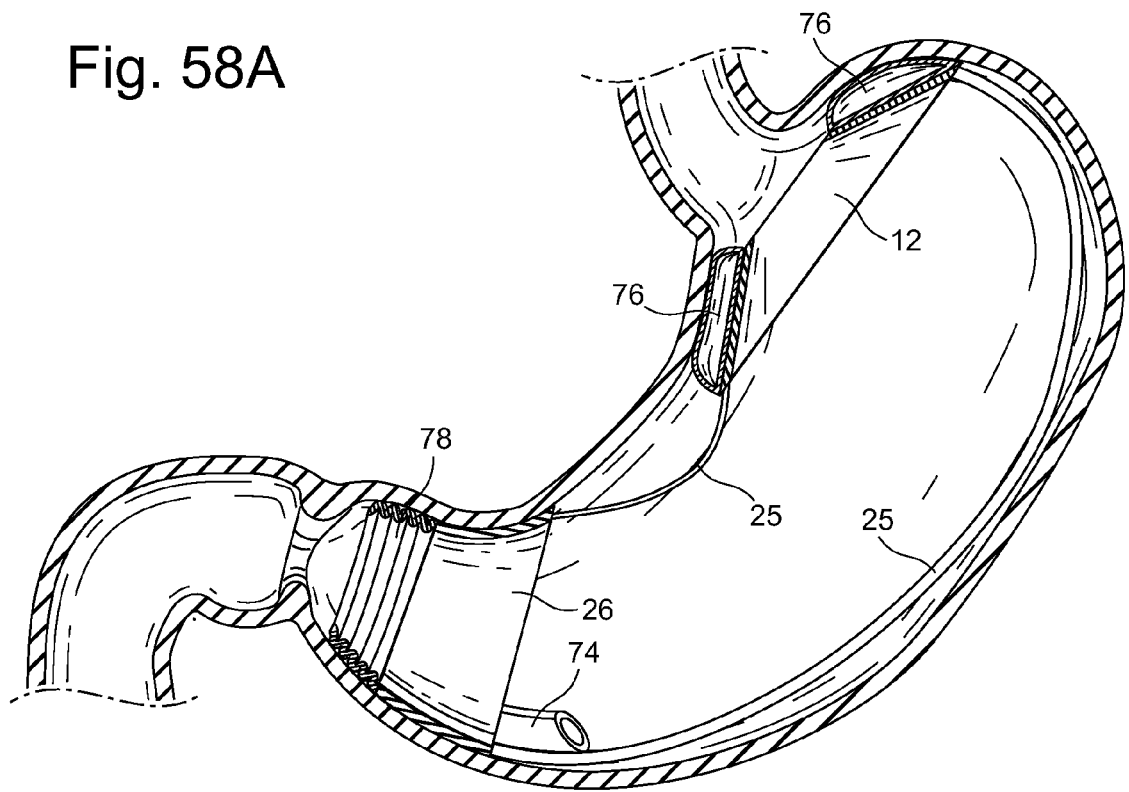
FIG. 58A depicts a side view of an embodiment of the present invention, having an adjustment mechanism in the pyloric element in an uninflated state, located within a cross-section of a stomach.
Figure 58B:
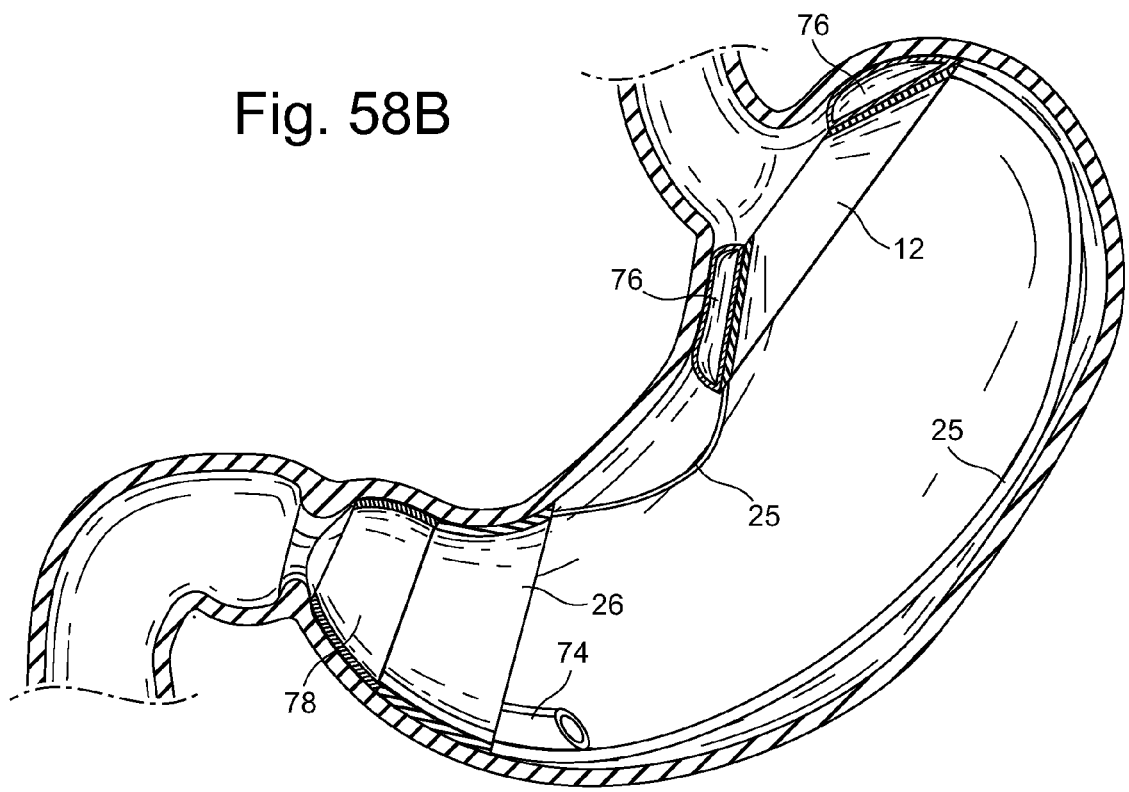
FIG. 58B depicts a side view of the embodiment shown in FIG. 58A, having an adjustment mechanism in the pyloric element in an inflated state, located within a cross-section of a stomach.
Figure 59:
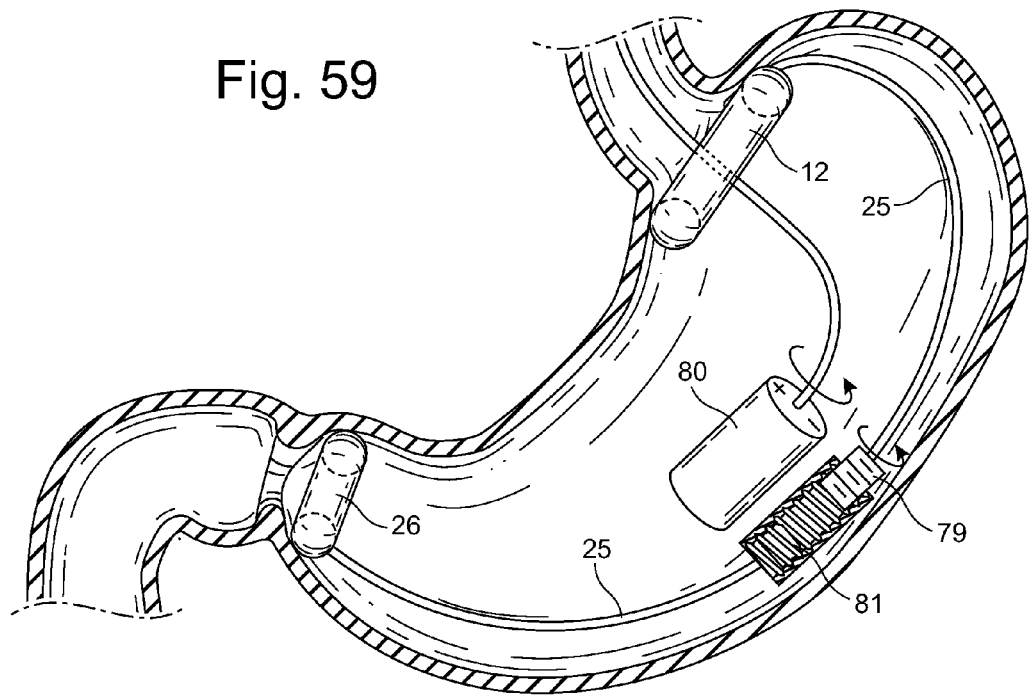
FIG. 59 depicts a side view of an embodiment of the bariatric device of the present invention, located within a cross-section of a stomach.
Figure 60:
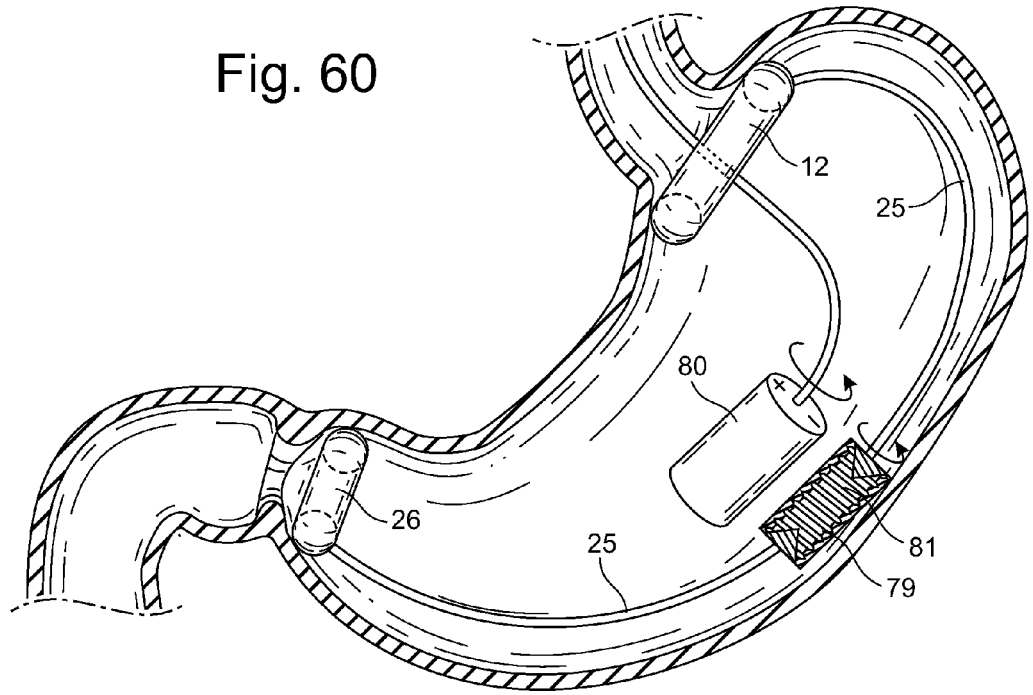
FIG. 60 depicts a side view of an embodiment of the bariatric device of the present invention, located within a cross-section of a stomach.

In another embodiment, the cardiac and/or pyloric element(s) 12, 26 could be equipped with one or more inflatable bodies, to increase or decrease the size of those element(s). For example, in FIG. 57, an inflatable body 76 is depicted atop the cardiac element 12, with an inflation element 74 such as a valve or an injection port on the connecting element 25. Inflating fluid, which could be saline, water, air, or other suitable substances, may be inserted or removed through the inflation element 74 to increase or decrease the size of the inflatable body 76. In such manner, the amount of contact and/or pressure imparted by the cardiac element 12 on the cardiac region 40 and/or the upper region of the stomach may be adjusted, either while the device 10 is in the stomach, or prior to placement. This balloon could cover the entire cardiac surface or could only cover portions of the cardiac surface to direct the inflation for a specific response. There may be one or more inflatable portions on the cardiac element 12. FIG. 57 also depicts a similar inflatable body 77 on the outside surface of the pyloric element 26. This could be accessed in the same manner as the cardiac inflatable body described above. Similarly, the inflatable body 77 could cover the whole surface of the pyloric element or could be have a portion or multiple portions for a desired effect. FIGS. 58A and 58B, shows a linearly inflatable body 78 on the bottom or distal surface of the pyloric element 26 to primarily allow for elongation of the element. The device 10 could contain linear and radial inflatable bodies.

A gastroscopic instrument could also deliver heat directly to an expandable body such as a heat expanding mechanism (such as one made of Nitinol) for expansion of a wax or wax-like expansion member.

For example, a Nitinol clip could clip into a positional location on a strut. The instrument could heat the clip to release and then reposition it into a different location, remove the heat and allow the clip to re-engage the positional feature to lock it into place.

The instrument could also have an inflatable body or a balloon to allow for physical contact with the device 10 to disengage a feature for repositioning into another location.

Magnetic actuation. Another adjustment mechanism could use magnets. See FIGS. 59, 60, and 61A and 61B.

For example, the positioning and/or connecting element 13, 25 could contain a thread with a magnetic nut 79 placed over it. Another strong magnet, the controller magnet 80, could be placed in close proximity to the implanted magnet to cause it to rotate. The rotation of the controller magnet 80 could create a magnetic field which would cause the internal magnet 79 to turn allowing it to advance and retreat along the threaded member 81.

The controller magnet 80 could either be external to the body or it could be placed on the end of a gastroscopic instrument for close proximity.

The controller magnet could be a magnet or an electromagnet to increase the intensity of the field and to improve magnetic coupling to ensure actuation.

The controller magnet 80 could also be multiple magnets to improve magnetic coupling.

Figure 63:
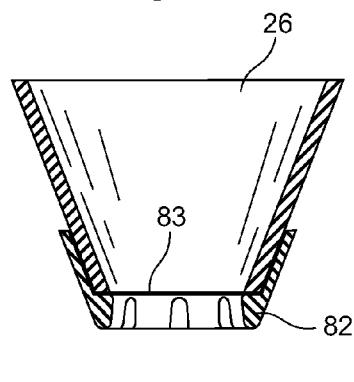
FIG. 63 depicts a cross-section view of an alternative embodiment of the adjustment cone shown in FIG. 62.
Figure 64:
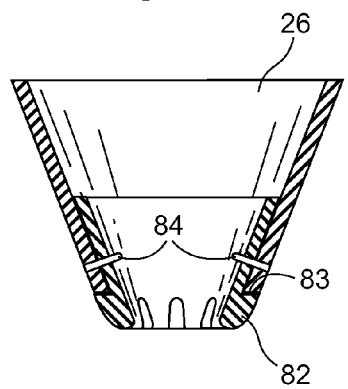
FIG. 64 depicts a cross-section view of an alternative embodiment of the adjustment cone shown in FIG. 62.

Another means of manually adjusting the length of the device 10 would be to have modular pieces that could attach or adhere to the cardiac or pyloric elements 12, 26. For example, an additional frusto-cone 82 could be placed over the pyloric element 26 to increase the length of the overall design. Several could be stacked together to create a variety of lengths. See FIGS. 62, 63 and 64. Stacking frusto-cones 82 could also be distanced from one another with a balloon on either frusto-cone to increase the distance between the two.

A variation of this embodiment would be to have an additional member that could be collapsible or compressible and inserted down the center of the pyloric element 26. Once it passes the pyloric element distal surface 83, the modular element 82 would expand and attach to the outer surface. Several modular elements 82 could be stacked together to create a variety of lengths. See FIGS. 62 and 63.

An alternative embodiment could have an additional element that could also pass down the center of the pyloric element 26 and expand past the distal surface 83, but with a clip 84 that would allow it to remain clipped to the inside surface. See FIG. 64. The attachment mechanism could be positionally based so that the element could be repositioned to several locations for a variety of lengths.

There could be several other means for manually actuating the design for repositioning.

As another variation of the above embodiments, the manual expansion mechanism could be adjusted remotely by an apparatus outside the body, and/or automated. The expansion could be achieved by a small motor that could be driven by an implanted power source or driven by a remote power source such as induction. The automated expansion could also be achieved by a pump, a syringe type plunger, a piezoelectric crystal, a bellows, a Nitinol motor, a pH responsive material that changes shape, thermal expansion of a gas, fluid or solid (example wax) expansion, magnet forces or any other type automated expansion or compression mechanism.

The control for activating this mechanism could be a remote control using a radiofrequency signal which can pass through tissue. The remote control could also be achieved by magnetic fields, time varying magnetic fields, radio waves, temperature variation, external pressure, pressure during swallowing, pH of any frequency or any other type of remote control mechanism.

Figure 65:
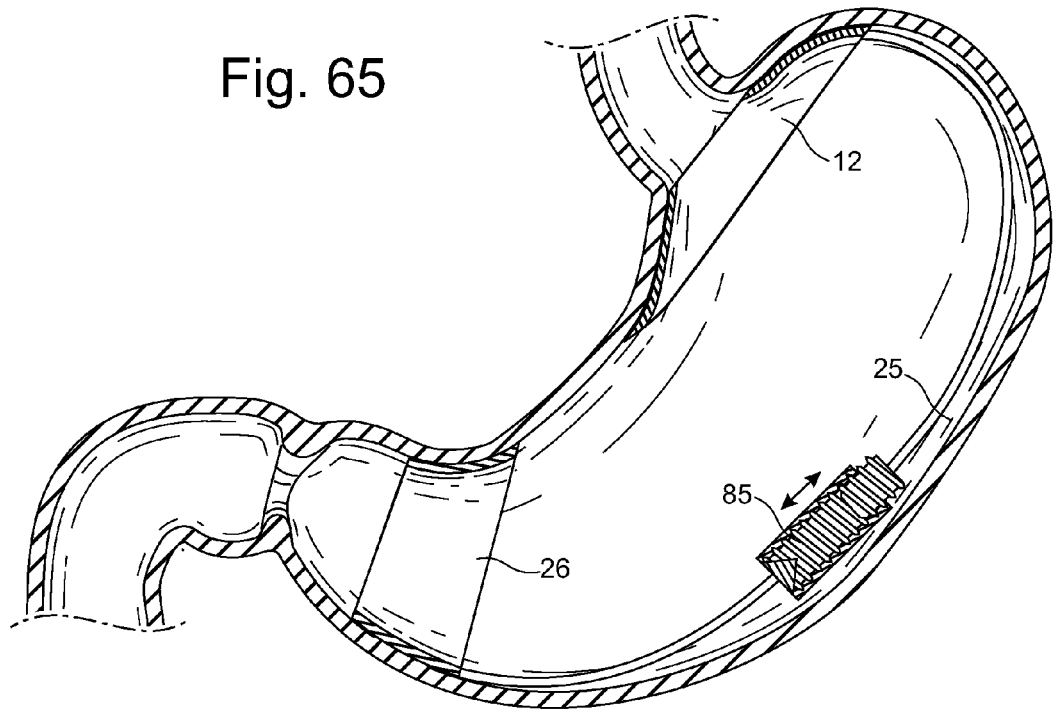
FIG. 65 depicts a side view of an embodiment of the present invention, equipped with adjustment mechanism shown in cross section, located within a cross-section of a stomach.

Actuation Mechanisms
Stepper Motor:
To adjust the length of the positioning and/or connecting element 13, 25 to increase the direct force onto the upper stomach or cardia 40, the adjusting element could be the positioning and/or connecting element 13, 25 entirely or partially comprised of a flexible, semi-flexible or rigid screw. A stepper motor 85 could be placed onto the flexible thread and could drive forward or back to allow the positioning and/or connecting element 13, 25 to draw together or push apart the elements. See FIGS. 65 and 55. These figures represent a threaded element that can be drawn together or apart.

The adjusting element may require power to drive the motor 85. The power could be supplied by an implanted power source such as a battery or it could be powered externally by induction through the coupling of an external antenna and an internal antenna.

An option would be to embed the internal antenna into any or all of the elements. This would allow for fewer structures in the design by encasing the antenna inside of one or more of the existing elements. The antenna could be a simple ring at the top or bottom or obliquely on either element or it could be placed in the wall of the device 10. The internal antenna could also be attached by a tether, free floating inside the esophagus, stomach or intestine. These could be made from materials to make them MRI compatible and/or MRI safe. This feature could be applied towards any actuation method where it is powered by induction.

For induction, an external hand held controller 86 may be required to transmit power for coupling. See FIGS. 66 and 67. The controller 86 could be set up to auto detect the internal antenna's presence and identify when coupling between the two antennas was adequate to allow for transmission and powering to take place, and to inform the user of function. This external controller 86 could then be used to display the distance that the stepper motor 85 had been advanced or retracted to allow the physician to control the adjustment. Similarly, the external controller 86 could be used for communication and control signals as an interface between the physician and the placed device 10. This feature could be applied towards any actuation method powered by induction.

An external antenna would be required for induction and could be placed into an external handheld controller 86. This could be placed directly against or close to the patient's body at the height of the internal bariatric device 10. The antenna could be housed with the other controller electronics in a single unit. This feature could be applied towards any actuation method powered by induction.

Another alternative would be to have the external antenna in the form of a belt 87 that would wrap around the patients abdomen at the height of the device 10 to better align the antennas for improved coupling. This feature could be applied towards any actuation method powered by induction. See FIG. 67.

The location of the actuation mechanism could also be inside any of the elements, or above or below any of them, or another location as would be best suited for the anatomy and function of the device 10. This feature could be applied towards any actuation method. Actuation could be accomplished by allowing the screw to be pushed or pulled inside any of the elements to embed the adjustment mechanism internally to one of the other elements. Other actuations mechanisms such as those listed above or others could also be used for this adjustment.

Induction could also be powered by an intragastric instrument. The instrument could have a flexible shaft that could fit through the mouth and down the esophagus or down the working channel of a gastroscope. Once the instrument was placed within or near the esophagus or stomach, it would allow the instrument to be in close proximity with the actuation mechanism in the device 10. The end of the instrument could have antenna(e) to allow for inductive powering and/or communication with the actuation mechanism for adjustment. This feature could be applied towards any actuation method.

Piezoelectric Motor

The adjustment could also be achieved by a piezoelectric element or motor 85. See FIGS. 65 and 55. These figures represent a threaded element that can be drawn together or apart.

There are several types of piezomotors that could be used for linear actuation. For example, a motor from NewScale Technologies (www.newscaletech.com) called the Squiggle Motor could be used which is very low profile and can be actuated when powered. Other motors or actuation mechanisms could also be used, and the Squiggle motor is just used as an example. In this example, there is a rigid screw that passes through the center of a threaded piezoelectric "tube" or element. When powered the piezoelectric element flexes side to side along the central axis to create an oscillating "hula hoop" action which causes it to translate axially along the rigid screw. The Squiggle motor could be attached to the positioning and/or connecting element 13, to advance or retract the cardiac and/or the pyloric element 12, 26. Alternatively, the Squiggle motor could be placed in between any of the elements. Alternatively, more than one Squiggle motor could be placed at these locations. One of the advantages of a piezoelectric motor 85 is that it would allow the device 10 to be MRI compatible and safe. As mentioned with the stepper motor 85 above, the piezoelectric motor 85 could be powered by an internal power source such as a battery or it could be powered by remote induction. The remote induction could be by a handheld external controller or it could be by a gastroscopic instrument placed down the esophagus. This motor could be encased in other materials to keep it dry and protected from the stomach environment.

Another embodiment of a piezoelectric actuated motor 85 would be to have a rotating piezoelectric member that could thread along one or two threaded members similar to a worm gear.

Another embodiment of a piezoelectric actuated motor 85 would be to have a piezoelectric crystal that elongates or flexes to actuate another member.

All of the piezoelectric motors 85 may contain a sealed housing such as an expandable metal or plastic bellows to prevent moisture of fluid from contacting the piezoelectric elements.

Magnetic Actuation

As mentioned above in the manual adjustment section, another adjustment mechanism could use magnets.

For example, at least a portion of the second element could be a semi-flexible thread or rigid thread with a magnetic nut placed over it. Another strong magnet, named a controller magnet 80, could be placed in close proximity to the implanted magnet to cause it to rotate. The rotation of the controller magnet 80 could create a magnetic field which would cause the internal magnet to turn allowing it to advance and retract along the threaded member.

The controller magnet 80 could either be external to the body or it could be placed on the end of a gastroscopic instrument for close proximity.

The controller magnet 80 could be a magnet or an electromagnet to increase the intensity of the field and to improve magnetic coupling to ensure actuation.

The controller magnet 80 could also be multiple magnets to improve magnetic coupling.

Nitinol Actuation

The adjustment element could also be actuated by Nitinol or a substance with similar properties. When a current is passed through Nitinol, it heats and causes the Nitinol to change its shape. Nitinol can expand into a variety of different shapes. A linear actuator could be made from Nitinol to advance or retract along an actuation member.

Heat could be generated from an implanted battery or it could be delivered by induction.

The second element could have multiple positional features such as holes, grooves, teeth or a wedging feature. A Nitinol clip could have a feature to engage these positional features. The Nitinol clip could be heated to change shape to allow it to advance or retract into different positional features to increase or decrease the length.

There are other Nitinol actuations that could be provided as well.

Ultrasound Motor

Another adjustment mechanism could be by use of an ultrasound motor or one powered by external ultrasound. This could use external ultrasound equipment to send sonic waves into the body to actuate the motor. This would also provide an MRI compatible option without requiring an internal power source or induction.

Hydraulic Actuation

The adjustment element 60 could also be actuated through hydraulic means for radial expansion or linear actuation as previously described. The cardiac or pyloric element 12, 26 could be inflated with a fluid to increase the diameter or length of the device 10 to increase pressures against the upper stomach or cardia 40, and pyloric region 42. It could increase in volume by accessing a self sealing membrane such as a self sealing drug delivery port, self sealing membrane on the expandable body, or a self sealing valve attached to the device 10. The inflation could be achieved by a piezoelectric pump, a peristaltic pump, a positive displacement pump or a syringe pump.

Piezoelectric pump: The pump could be comprised of a piezoelectric element which can flex to propel fluid directly or a member that could propel fluid. For example, a piezoelectric disk could be captured in a housing with an incoming channel and an outgoing channel. The disk could be powered to cause it to flex into a dome shape to push fluid into the outgoing channel. A valve would be required to close the incoming channel to ensure directional flow to the outgoing channel. Similarly, the piezoelectric Squiggle motor as described above could be used to linearly actuate a fluid up or down a tube to hydraulically actuate position.

Stepper motor pump: Actuation could be achieved by a stepper motor where the motor linearly actuates to compress a reservoir or syringe to move fluid within a tube or constrained volume.

Wax expansion pump: Fluid could also be propelled by a wax expansion mechanism. When wax is heated to melting it expands by approximately 30%. A solid plug of wax could be heated to expand and drive fluid through a valve to hydraulically actuate lengthening. The lengthening structure could be made to move only in one direction, so that when the wax cools it will not contract. The wax expansion could also be used to actuate other adjustment mechanisms.

Peristaltic pump: The members could also be driven by a peristaltic pump. In this mechanism, the external diameter of a cylindrical actuator could be used to compress a length of tubing to create an occlusion. The cylindrical actuator could be rotated along the tube to drive fluid forward or backwards inside the tube. The peristaltic pump could also be actuated by a stepper motor or by a piezoelectric element or other.

Gas expansion/propellant pump: The length could also be actuated by a gas expansion pump where a gas like Freon or others could be used to expand when exposed to a higher temperature. Similar principles to the devices like the Codman pump could be used. This change in volume could drive the pump forward. Similarly, there could be compressed gas constrained in a pressure vessel with a valve. The valve could be remotely activated to allow gas to propel a syringe, fluid or to compress a constrained volume.

Positive displacement pump: There are implant grade positive displacement pumps that are available on the market for drug delivery that could be used to displace a specific amount of fluid for hydraulic inflation of the adjustment element 60.

Syringe pump: A syringe pump could be made by advancing fluid through a syringe. The syringe could be actuated by a stepper motor, a piezoelectric actuator, a magnet or by a Nitinol actuator as described above.

Hydrogel: the adjustment element could also be inflated by use of a hydrogel to absorb fluids and could be actuated by changes in temperature, pH or tonicity to change shape or volume Hypertonic fluid: the adjustment element 60 could also be inflated by using a hypertonic fluid in the inflation area and allowing it to absorb fluid across a semi permeable membrane.

Mechanical means for diametrical changes. Similar to the inflation, elongation, and shortening embodiments described above, the device 10 could change diameter by various actuation mechanisms. All of the above-described mechanisms could also be adapted for use for a diametric change instead of a linear change.

As a variation of the embodiments discussed above, the device 10 could have a sensor 88 that could sense a parameter such as pressure, motion, peristalsis, tension, pH, temperature, or other appropriate parameters, or various parameter combinations. The sensor 88 could output a signal to be used by an actuation element to actuate an adjustment element, to a memory element such as a microchip, or be read by a remote reader or remote controller.

Figure 68:
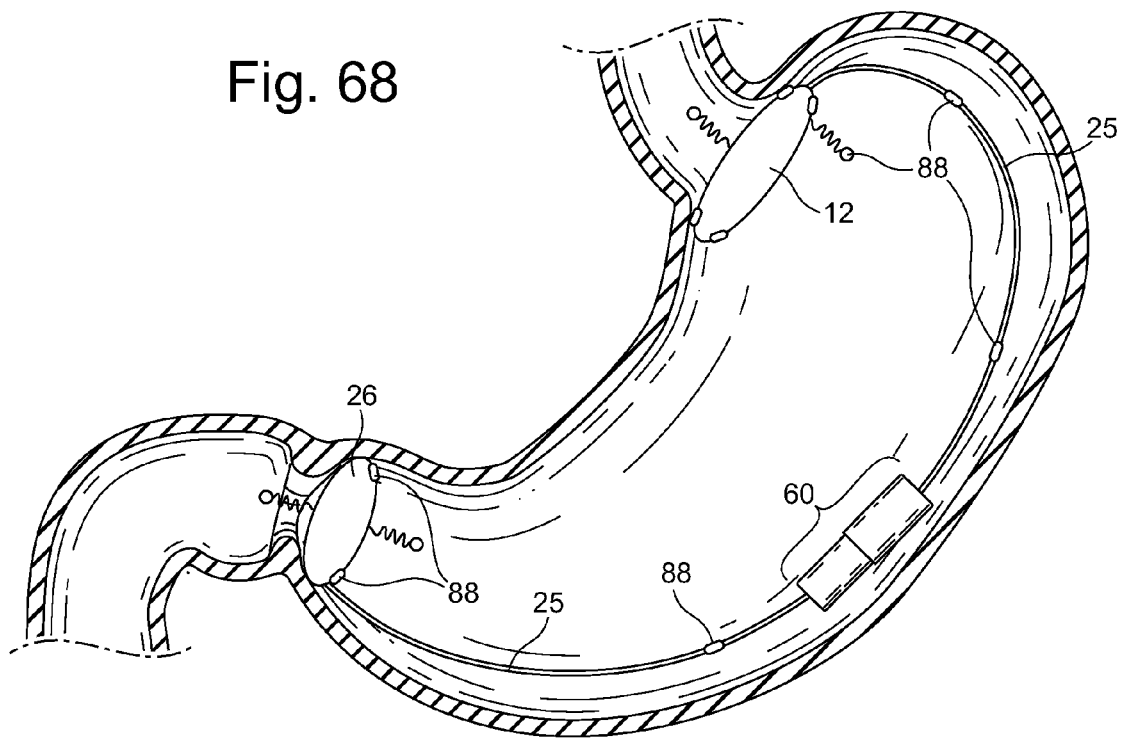
FIG. 68 depicts a side view of an embodiment of the bariatric device of the present invention, located within a cross-section of a stomach.
Figure 69:
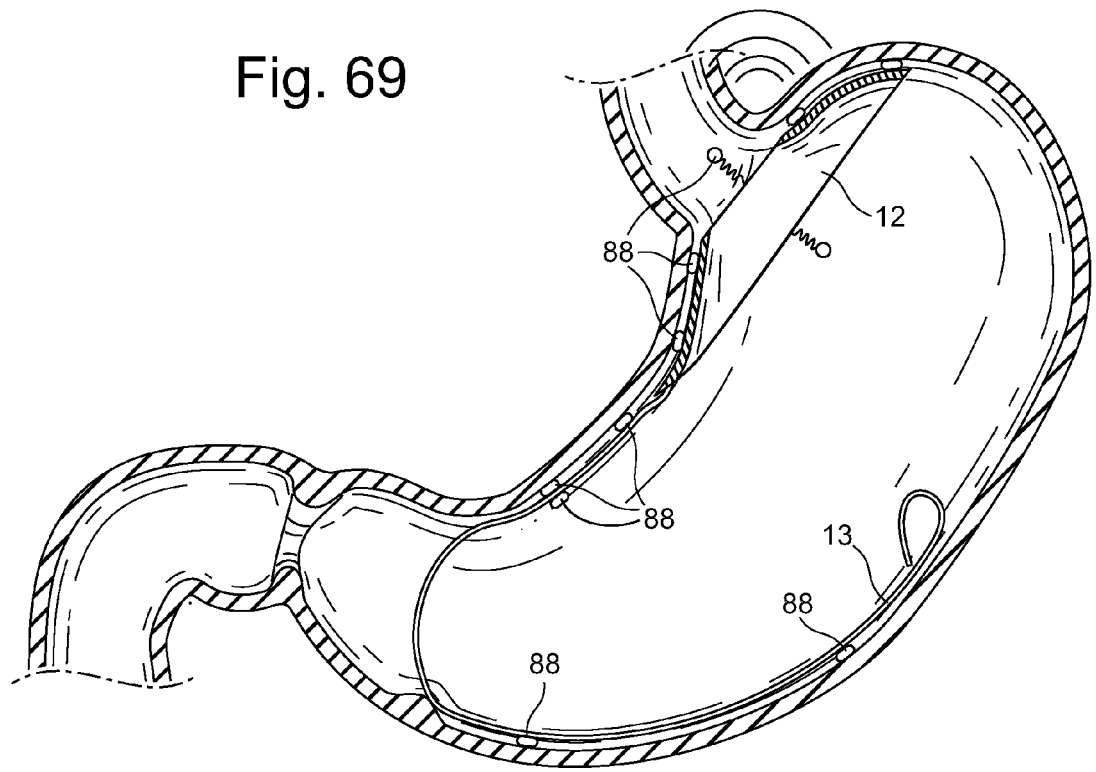
FIG. 69 depicts a side view of an embodiment of the bariatric device of the present invention, located within a cross-section of a stomach.

Sensors 88 could be used to gather important patient data to understand performance, patient status or whether an adjustment needs to be performed. For ease of use and compatibility with the body, wireless sensors would be preferred. The sensors 88 could be direct tissue contact, intermittent patient contact or could monitor the intraluminal pressure inside GI tract. The data could be used for no other reason than to just monitor patient status. FIGS. 68 and 69 depict sensors 88, which could be embedded in any of the elements or it could be tethered to any of the elements to allow it to be suspended inside the GI tract. Based on the sensed parameter, the device 10 could be adjusted. The adjustment could have an open or closed loop system increasing or decreasing the applied force, pressure or sensed parameter. The sensed parameter could detect whether the device 10 was not at an ideal condition, and could then send a signal to a control mechanism for automatically adjusting the system. This mechanism could be under physician control (open system) or without physician control (closed system). It could also control the shape of the cardiac, pyloric, connecting, and/or positioning elements 12, 26, 25, 13 to vary stiffness, size, length, form or shape. In general, the sensor 88 could sense a parameter and then adjust the device 10 as needed to bring the sensed parameter into the ideal range. There could be an algorithm that controls the ideal parameter or it could be based on a parameter range. The device 10 would be adjustable to meet the needs of the patient.

In an open loop system, the physician would have control of when the device 10 would adjust. The device 10 could be passive and only inductively powered when in close proximity to an external controller under the supervision of a physician. For example, in the clinic the physician could have a remote controller with the ability of powering the device 10 inductively, and then begin to monitor the sensors feedback signals to see physical parameters of the patient at baseline such as pressure of the device 10 against the cardia. The sensor monitoring could also be performed while the patient is eating or drinking, or not eating or drinking. As the patient consumes, the esophageal and stomach peristaltic waves will increase in intensity as they propel the food or drink from the mouth to the stomach. A sensor 88 could detect when these waves increase in amplitude, frequency, and pressure. The parameter could read on the external controller by the physician, and then the physician could send a signal to the automated expansion mechanism in the device 10 to adjust the device. The physician could then query the sensor 88 again to determine whether the device 10 was in the ideal settings and whether the pressure against the cardia or sensed parameter was optimized. The physician could iteratively control the amount of adjustment and monitor the parameters until the ideal condition was met.

Alternatively, the physician could read the parameter signals while under his supervision, but have the sensors 88 send a signal directly to the automated expansion mechanism to adjust until the device 10 was within the ideal parameters. The data collected could be analyzed by the controller for averages, minimums, maximums and standard deviations over time and use an algorithm to determine the ideal settings. The controller could then monitor and adjust on its own until the ideal conditions were met, but while the physician was present to verify all conditions and verify patient acceptance.

In a closed loop system, the device 10 would be active with its own integrated power source. The device 10 could wake up at routine intervals to monitor or could monitor all the time. The data collected could be analyzed for averages, minimums, maximums and standard deviations over time and use an algorithm to determine the ideal settings. As the patient begins to consume food or drink, the device sensors 88 would detect the sensed parameter and signal the automated expansion/contraction mechanism to adjust the device 10 as needed. In this embodiment, the device 10 could be fully automated and would not require intervention from an outside individual.

In either the open or closed loop system, there could be multiple sensors 88 on the device 10 to determine the pressure or force areas, or other sensed parameters on the device 10 and where it needs to be varied to meet the ideal conditions for the stomach. In the case where the positioning and/or connecting element 13, 25 has multiple components, this could be used to align the device 10 in the stomach to provide a custom fit for each person. There could also be a mechanism to adjust the alignment of the cardiac and/or pyloric elements 12, 26 relative to the connecting and/or positioning element 25, 13. The sensor(s) 88 could have a built in power source or it could have a remote power source such as induction so that it would only wake up and activate when an external controller was brought near.

The device 10 could have integrated memory to allow storage of patient and device 10 data. This could include but is not limited to the serial number, the patient's information such as name, patient number, height, weight; the physician's name, the adjustment history including the date and time, the amount adjustment and the sensed parameters. For the active device, there could be 24 hour data recording of key parameters or there could be data collected at key intervals throughout the day to detect when the patient is eating and whether they are being compliant with their eating. It could record weight tracking, BMI or other data as needed which could be queried by an external controller. This data could also be downloaded into a physician's patient tracking database for ease of patient tracking. Similarly, this data could be downloaded and tracked on an internet tracking website, where the patient could log on and see their history and progress. The patient could add information to the website such as weight or an eating log, adverse events or other conditions that the physician or patient would like to track.

In the open system, the physician could choose to collect and record data as needed at the time of the adjustment such as weight, date, time, and adjustment amount or other.

For an open loop system, the device 10 could be adapted to allow for remote adjustments over the phone. This would be especially advantageous for patients living in rural areas where they are far from their physician's office. It could also be for convenience of having an adjustment without having to travel to the physician's office. This would allow a physician to discuss the patient's progress with the patient directly and then query the device sensor 88 to see how the device performance is. Based on the feedback of the device 10, the physician could then adjust the patient.

In yet another embodiment, the device 10 could have an emitter element for dispensing a drug, hormone or bioactive agent to further induce satiety, weight management or other disease management such as diabetes. The drug could be a weight management drug currently on the market or one to be developed. Similarly, it could be a satiety hormone or other bioactive agent. In the published literature, there is a growing mass of information on satiety hormones. The bioactive agent could be applied by the emitter element through a drug eluting coating, a reservoir with a pump, or a permeable membrane placed on the device 10 where the drugs could pass from the device 10 into the gut. The emitter element could release such substances in response to a signal from a sensor 88, a timed basis, or other release criteria. The device 10 could have a tube that trails into the intestines to allow the drug to be delivered downstream where the pH is higher and would not destroy the bioactive agent.

The device 10 could have a surface finish or macrotexture for gripping the stomach. If the device 10 could grip the inner mucosa of the stomach, it could elongate or expand to further stretch the stomach in key areas to induce further satiety as needed. For example, the cardiac element 12 could be a conical spiral with a surface texture that lightly grips the mucosa and or stomach musculature. If the spiral were made of Nitinol or other temperature-sensitive substance, the device 10 could expand the spiral by a variation of temperature. By applying a temperature variation, such as by drinking a hot liquid or otherwise, the device 10 could expand and cause a satiety response. The surface could be multiple protuberances, barbs, a rough bead blast, or other finishes suitable for gripping the stomach wall.

Figure 70:
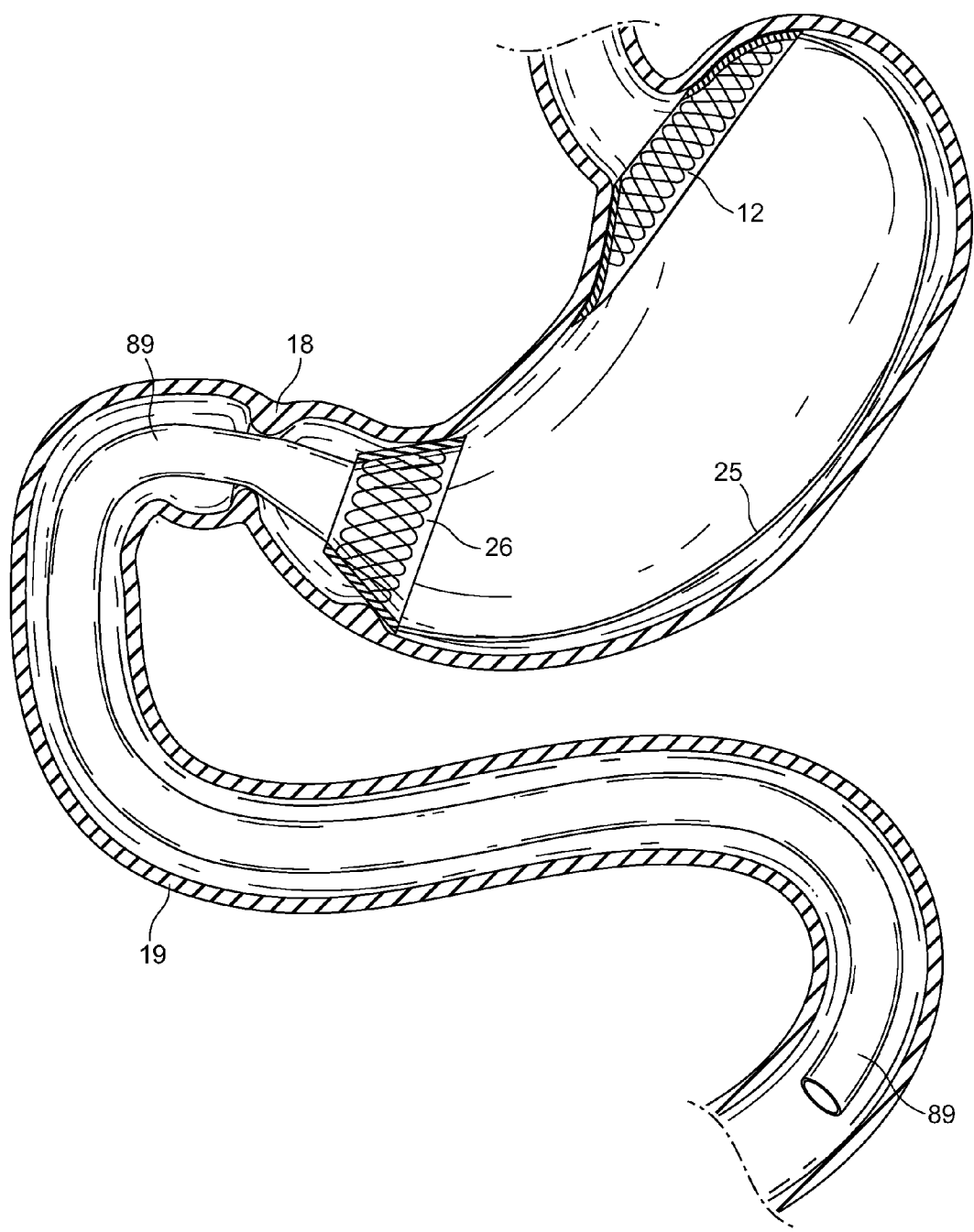
FIG. 70 depicts a side view of an embodiment of the bariatric device of the present invention, located within a cross-section of a stomach and a duodenum.
Figure 71A:
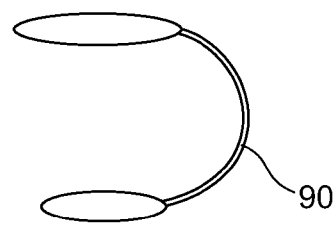
FIG. 71A depicts a side view of an adjustment mechanism in an unexpanded state, of an embodiment of the present invention.
Figure 71B:
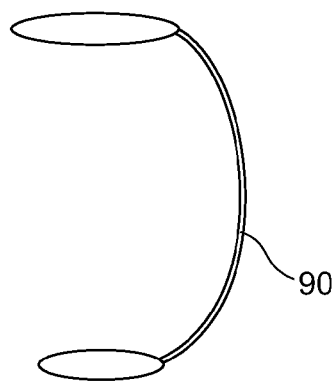
FIG. 71B depicts a side view of an adjustment mechanism shown in FIG. 71A, in an expanded state.
Figure 72A:
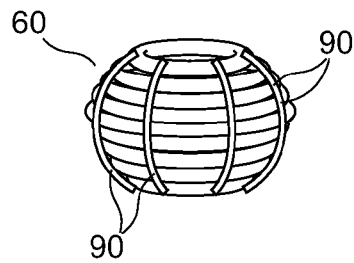
FIG. 72A depicts a side view of an adjustment mechanism in an unexpanded state, of an embodiment of the present invention.
Figure 72B:
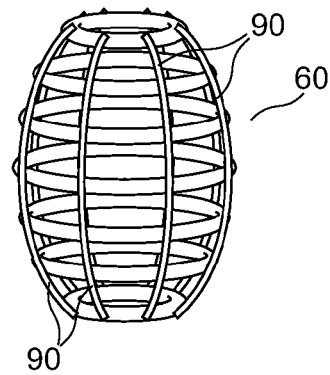
FIG. 72B depicts a side view of an adjustment mechanism shown in FIG. 72A, in an expanded state.
Figure 73A:
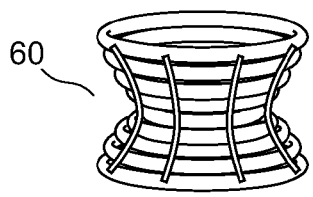
FIG. 73A depicts a side view of an adjustment mechanism in an unexpanded state, of an embodiment of the present invention.
Figure 73B:
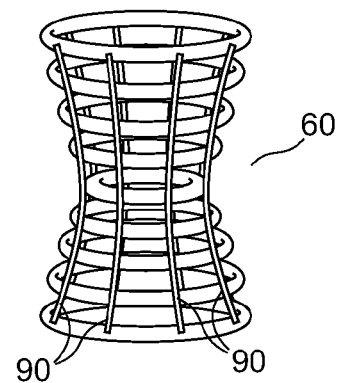
FIG. 73B depicts a side view of an adjustment mechanism shown in FIG. 73A, in an expanded state.

The device 10 could have a thin flexible tube 89 attached to the pyloric element 26 that could trail into the duodenum 19 to act as a barrier to food absorption. See FIG. 70. This tube 89 would be of similar diameter to the duodenum 19 and all food passing through the pyloric element 26 would pass directly into this sleeve. Similar to the rerouting performed in a gastric bypass or Roux en Y bypass, the sleeve 89 would be approximately 100 cm long, but could be longer or shorter depending on the amount of malabsorption required. This tube 89 may be made of an acid resistant material such as Teflon, PTFE, ePTFE, FEP, silicone, elastomers or other acid resistant materials.

As a variation of the device 10, it could incorporate electrical stimulation to the stomach musculature, stomach nerves or the vagus to further improve satiety stimulation and weight loss. Energy used for this stimulation could be RF, ultrasound, microwave cryogenic, laser, light, electrical, mechanical or thermal. The device 10 could have leads incorporated that could embed into the stomach wall or be surgically placed around a nerve, or the stimulation could be applied directly through surface contact of the device 10 to the stomach mucosa.

In yet another embodiment, the bariatric device 10 may have an adjustment element 60 that is equipped with a temporary expansion/contraction element 90 that may allow for temporary adjustment based on activation of a material property, sensor 88 or mechanism of the device 10. This could be applied to any of the above-discussed embodiments. See FIGS. 71A, 71B, 72A, 72B, 73A, and 73B. It may be desirable for the temporary expansion/contraction element 90 to adjust only upon eating, and then retract after eating. It may be desirable for the device 10 to adjust with the pH cycle of the patient where pH will be higher prior to eating and then lower after eating. This would allow for intermittent stimulation of the stretch receptors to avoid receptor fatigue over time. For example, the material could be heat sensitive using materials such as Nitinol, which could expand after consuming a hot liquid. Similarly, the device 10 could have a sensor 88 or material that is pH or glucose sensitive or detect the presence of food, which could activate the temporary expansion/contraction element 90 to expand when a certain threshold for pH has been reached or glucose or fat is present after eating. Similarly, this temporary expansion/contraction element 90 could be activated by a magnetic field such as swallowing a magnetic pill that could temporarily expand the device 10. In this example, the magnetic pill would be small enough and shaped appropriately for passage through the gastrointestinal tract, and biocompatible. The patient could consume the electromagnetic pill when a satiety signal was desired. It may also be desirable for the device 10 to adjust based on time or sleep cycle such that the device 10 adjusts at specific times of the day or when the patient lays horizontal. Other parameters or mechanisms to trigger the temporary expansion could be used.

Placement

As mentioned above, a tube, catheter, or sheath may be required to protect the anatomy during placement of the device 10 down the esophagus and into the stomach. It could be a simple flexible tube such as silicone or urethane tube to aid in straightening and compressing the device 10 while it is being introduced. Insertion of the device 10 into the tube would require compression of the device 10 into a narrow, insertable shape. A standard gastroscopic tool could be used to push or pull the device 10 down the tube. Similarly, a custom gastroscopic tool or sheath could be used to introduce the device 10 into the stomach through the esophagus or other narrow opening.

Figure 74:
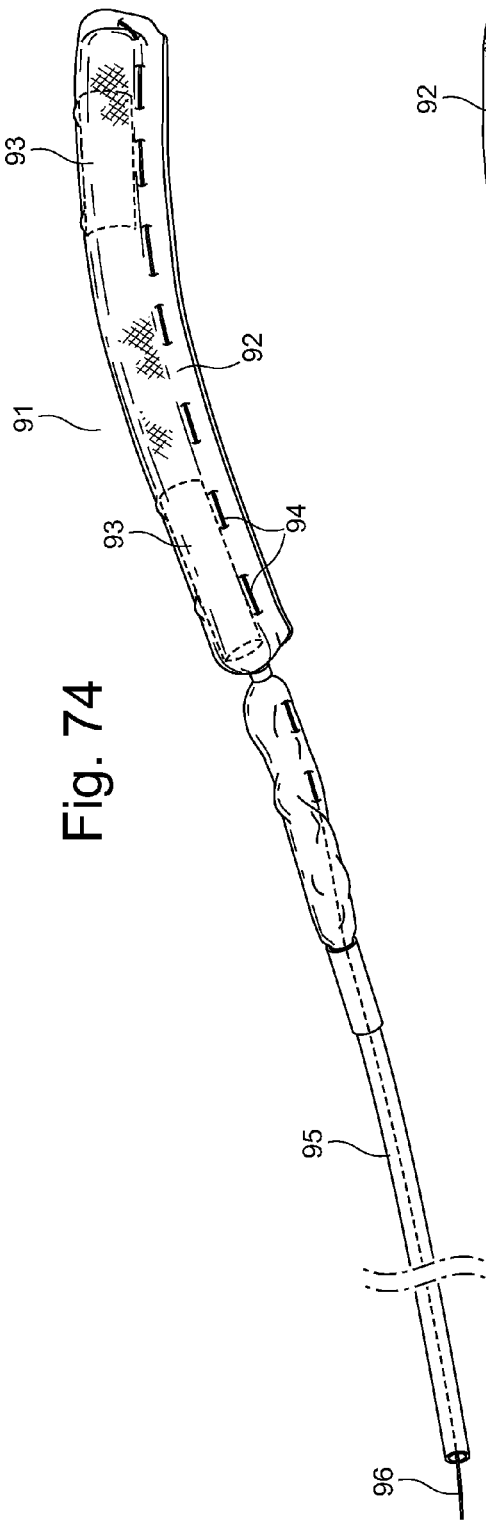
FIG. 74 depicts a side view of a delivery sheath containing a medical device.
Figure 75:
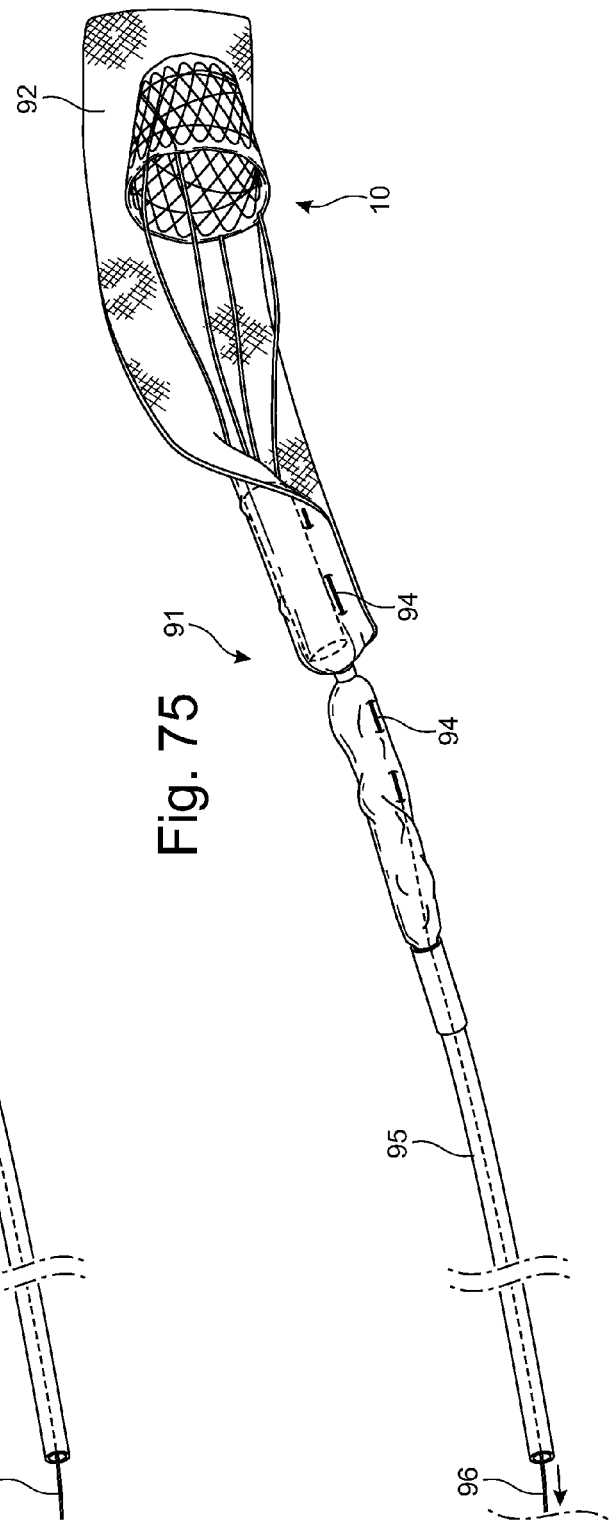
FIG. 75 depicts a side view of the delivery sheath shown in FIG. 74, partially opened to show an expanded medical device.

A delivery sheath 91 may be used to insert the device 10 though the esophagus 32 or other narrow opening into the stomach for placement. In one such embodiment, a lightweight fabric, sheeting or material 92 may be used for the sheath 91, made of a suitable material that is thin, flexible, soft, smooth, compliant, adequately lubricious to slide down the esophagus 32 and adequately strong to hold the device 10 in a compressed state 93 such as fabrics made from polymers such as nylon, teflons, eptfe, polyester, or polymer coated fabrics such as ptfe coated cotton or other fabrics or other sheeting materials. Although a fabric could be used for the material 92, other substances may be used, such as silicone, polyurethane, thin walled plastic or other suitable substances. First, the bariatric device 10 may be compressed into a narrow shape to fit inside the sheath 91, and held in a compressed state by a tube, fixtures, or the like. Then the material 92 may be draped around the compressed device 10 lengthwise, and secured in a closed position with a deployment member 94. The material 92 could also be closed with a deployment member 94 and the collapsed device 93 then inserted inside the closed sheath 91. The deployment member 94 could be a small gauge wire or lace placed in a single straight stitch along the length of the material 92 around the compressed device 93, as shown in FIGS. 74 and 75. The deployment member 94 may be of any of a variety of suitable materials. In a preferred embodiment, the deployment member 94 is a single thin wire, preferably capable of holding its original shape even after being bent. Such wire could be made of Nitinol, spring steel, small diameter braided cable or spiral wound guide wire, or other suitable material. Although a deformable wire could be used, it may be more difficult to remove for placement if the bends become too extreme during handling. The deployment member 94 may also be thread material, such silk, rayon, nylon, polyester, eptfe thread, ptfe coated thread and the like. The deployment member 94 may be terminated by stitching the deployment member 94 around the distal end (the end inserted into the body first) of the material 92 to close the distal end of the sheath 91, and turned back around and inserted inside the material 92 towards the proximal end.

Alternatively, the distal end of the deployment member 94 may be secured in a pocket attached to the interior or exterior of the material 92 at or near the distal end of the sheath. For the deployment member 94 such pocket may be in the form of a plastic cap, silicone cap or other suitable material that will protect the wire end from poking or snagging tissue during placement. In such an embodiment, the distal end of the material 92 may be folded over towards the proximal end like an envelope so that the deployment member 94 may secure the distal end of the sheath material 92 without having to stitch around the end. The pocket may then be attached to the material 92 at or near the fold.

The deployment member's proximal end 96 may extend far enough so that it may be accessed outside the patient after the device 10 is placed into the deployment position in the stomach. Preferably, a thin tube 95 made of silicone or plastic is secured to the proximal end of the material 92, and the deployment member 94 is routed inside the tube 95. Such a tube 95 may be independently secured to the material 92 so that the distal end of the tube 95 is just inside the proximal end of the material 92. Then the compressed device 10 may be placed within the material 92 and secured with the deployment member 94. The result is a package with a compressed device 93 inside the closed material 92 and a tube 95 also secured inside the proximal end of the material 92, with the deployment member 94 running through the tube 95. For adequate stiffness for placement, an additional guide wire may be needed to be placed down the center the sheath assembly.

For placement, such a sheath package is placed into the esophagus 32 or other narrow opening or surgical incision, and routed into the stomach. Once in deployment position, the deployment member 94 is pulled through the tubing 95, which releases the closure of the sheath. The device 10 will then expand or regain its operational shape. Then the tube 95, along with the material 92, may be removed from the patient leaving only the device 10 in place.

The delivery sheath 91 may be used for any delivery of any medical device through a narrow opening. If the medical device is naturally narrow, or can be compressed, deflated, or other means of holding it in a narrow shape, it may be placed in a delivery sheath 91 as discussed above. After the deployment member 94 is pulled through the tubing 95, the medical device may expand or rebound into its operational shape, whether by its construction of shape-retaining materials, or by mechanical, hydraulic, pneumatic, or other means.

Measurement Tool

To select the appropriate size device or device adjustment for the patient, a measurement tool may be used. This tool would allow measurement of the lesser and greater curves, 16, 17 of the stomach, the distance between the pyloric and cardiac elements, or other features of the stomach.

Figure 76:
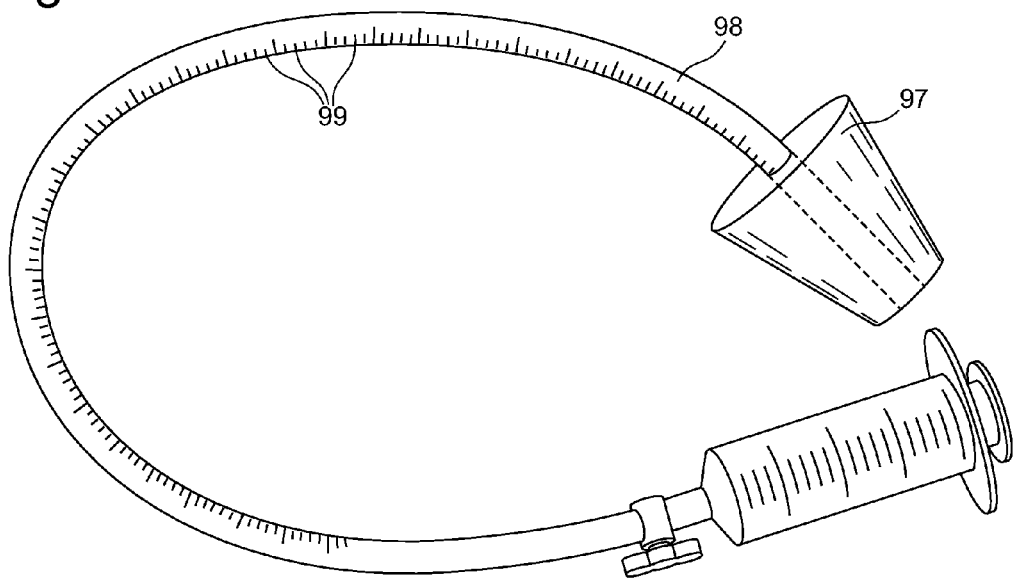
FIG. 76 depicts a side view of an embodiment of a stomach measurement device.

In one embodiment, the measurement tool has an inflatable body 97 that is in the same general shape as the pyloric element 26. This balloon may be affixed to a central tube 98 to allow for a pathway where air can be passed to inflate and deflate the balloon 97. The central tube 98 may also provide a handle for placing the balloon 97 and maneuvering the balloon into position in the pyloric region 42. The central tube 98 measurement member may be used alone or in conjunction with additional measurement members. See FIGS. 76 and 77. For placement, the inflatable body 97 would be deflated to collapse it to a narrow, low profile, and preferably inserted into the stomach through the esophagus 32. See FIG. 78.

A measurement member could be affixed to the inflatable body with adequate length to start a measurement at the base of the pyloric inflatable body 97 and measure along the lesser curve 16 or greater curve 17 to the gastroesophogeal (GE) junction. This measurement member could be long enough to pass up the esophagus for manipulation outside the body or could be long enough to pass the GE junction. This measurement member may be equipped with measurement markings 99, which could be a thin measurement tape 100, a tube with length markings 101, the central tube coupled with the inflatable body, or a clear tube with a plunger to allow for visualization of the plunger with the measurement on the plunger. For the clear tube/plunger embodiment, the measurement markings could be on the tube for visualization by the gastroscope, or the measurement markings may be on the plunger such that when the bottom or other part of the plunger is aligned with the stomach feature, the measurement is read outside the body by viewing the markings on the plunger relative to a point on the tubing. Once the inflatable body 97 is in position in the pyloric region 42, the inflatable body 97 could be inflated to match the shape and profile of the pyloric element 26. Alternatively, the inflatable body 97 may be inflated in the stomach and then pushed into the pyloric region 42.

Once the inflatable body 97 is seated in the proper position, various features of the stomach may be measured. For the lesser curve measurement, the inflatable body 97 may be positioned so that the measurement member is located along the lesser curve 16. Under gastroscope visualization, the measurement member could then be pulled up to position in the GE junction by the member itself or by an instrument, and the measurement reading noted. For the greater curve measurement, the inflatable body may be positioned so that the measurement member is located along the greater curve 17. Under gastroscope visualization, the measurement member could then be pushed into position along the greater curve 17 and up through the GE junction by the member itself or by an instrument, and the measurement reading noted. The measurement members could be made of silicone, an elastomer or other material that is compliant and smooth. The measurement member should be of adequate strength to maintain a good measurement, but be smooth and complaint for placement down the esophagus and for conforming to the stomach's anatomy.

Figure 77:
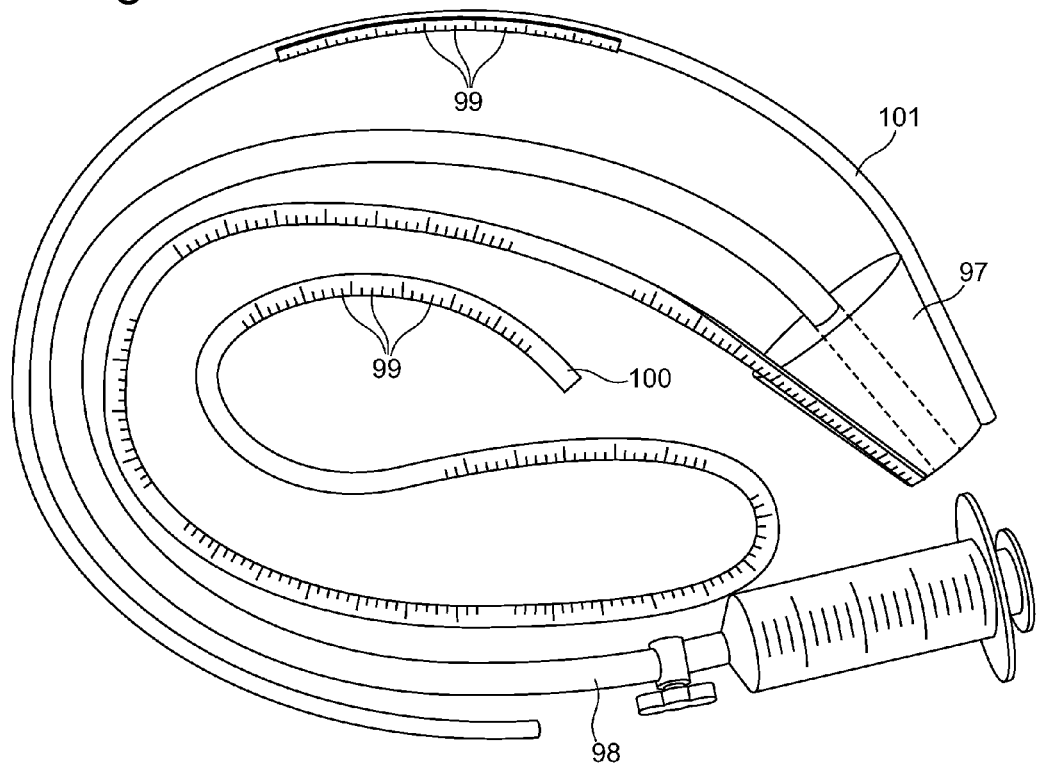
FIG. 77 depicts a side view of an embodiment of a stomach measurement device showing the frusto-conical member in an inflated state.

In another embodiment, the instrument may contain two measurement members on opposing sides of the inflatable body to measure the greater and lesser curves at the same time as shown in FIG. 77. In another embodiment, the central tube 98 could also be used as a measurement member and pushed to flex and contour along the greater or lesser curve 16 for a measurement. See FIG. 76. Preferably, the inflatable body 97 matches shape of the pyloric element 26 of the device 10, but it could also take another shape such as a sphere to approximate the size of the pyloric element 26. The inflatable body may also be shaped for other measurement uses, and adapted to fit whatever area of the stomach may be required. Alternatively, the inflatable body could be replaced with a non-inflatable body if needed. In the embodiment where the central tube 98 is used for measurement, the central tube 98 could be offset from the center of the inflatable body 97 to allow it to better contour to the greater or lesser curves 17, 16.

In another embodiment, the measurement tool may contain a fixed pyloric member and a moveable cardiac member that can translate along a central tube 98 to approximate the distance between the two members in the recipient's stomach. The central tube 98 may contain measurement markings 99 that can be visualized once the cardiac member has been positioned. The cardiac member may include a pressure sensor to guide when adequate pressure has been incurred to represent proper seating of the cardiac device 10 in the stomach.

In another embodiment, the measurement tool may comprise an inflatable balloon at the pylorus and an inflatable balloon near the cardia. As the cardiac balloon is inflated, it may approximate the location of the cardia. The cardia balloon may contain a pressure sensor internally or externally to guide when an appropriate contact pressure to the cardia has been achieved to approximate the size.

Removal

For removal, a flexible tube such as a standard overtube could be used with a standard or custom endoscopic tool. The tube may be placed down the esophagus and the tool then placed down the lumen of the overtube. A standard tool such as a grasper or snare could grasp the device 10 and pull it up the tube. The device 10 would be straightened by the overtube for removal from the stomach and esophagus.

In another embodiment, the elements may incorporate a collapsing mechanism designed to collapse the element into a compact shape for removal. For example, FIGS. 79 and 80 depict a pyloric element 26 with a constriction member 102 comprising a wire or thread sewn spirally around, through, or inside the length of the element. The constriction member 102 could also be sewn through eyelets or features attached to the inside of the pyloric or cardiac element 26, 12. The ends of the constriction member 102 may be connected. When the constriction member 102 is pulled, it tightens the circumference of the pyloric element 26 like a drawstring, which collapses the element down to a narrow profile that can be safely removed through the esophagus or other narrow opening, or ease its placement into a tube for removal. Similar collapsing mechanisms can be installed in the cardiac, connecting, and/or positioning elements 12, 25, 13. The constriction member 102 could be made from Nitinol, stainless steel wire, ptfe thread, eptfe thread or ptfe coated threads or other suitable materials. The constriction member 102 could be integrated into the elements in a variety of patterns such as a continuous spiral, two spirals of reversing orientation, or other.

Figure 81A:
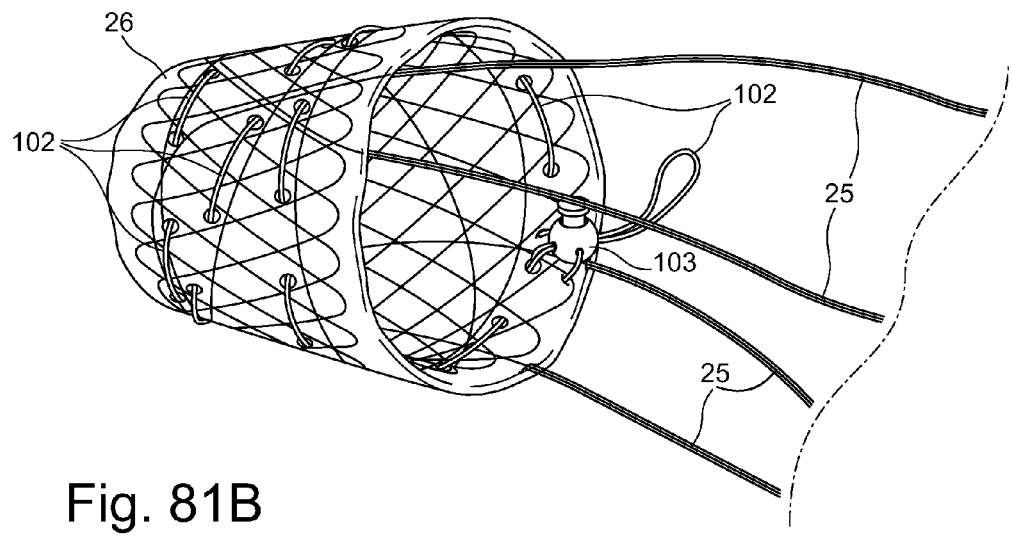
FIG. 81A depicts a perspective view of a pyloric element equipped with a constriction element with a mechanical stop, in an embodiment of the present invention.
Figure 81B:
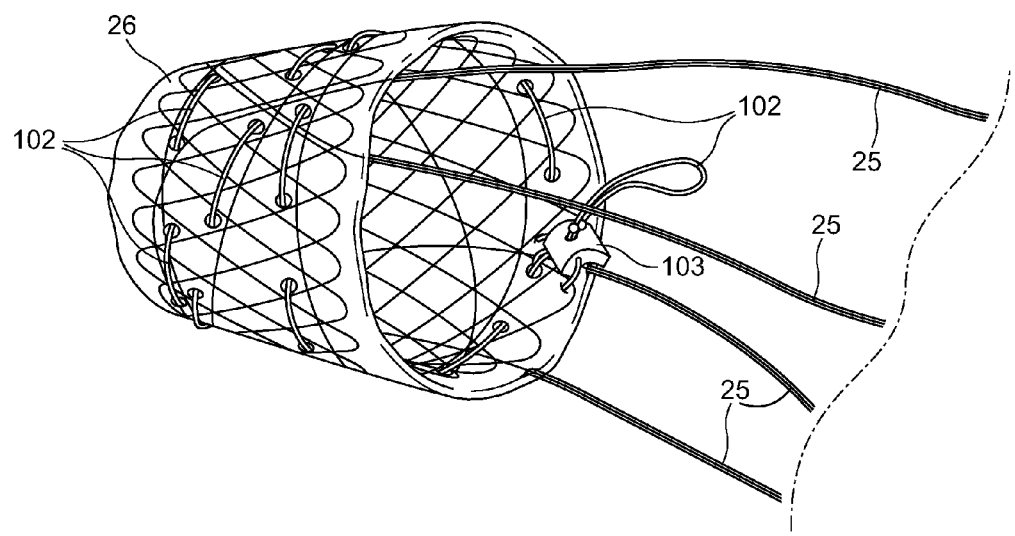
FIG. 81B depicts a perspective view of a pyloric element equipped with a constriction element with a mechanical stop, in another embodiment of the present invention.
Figure 82:
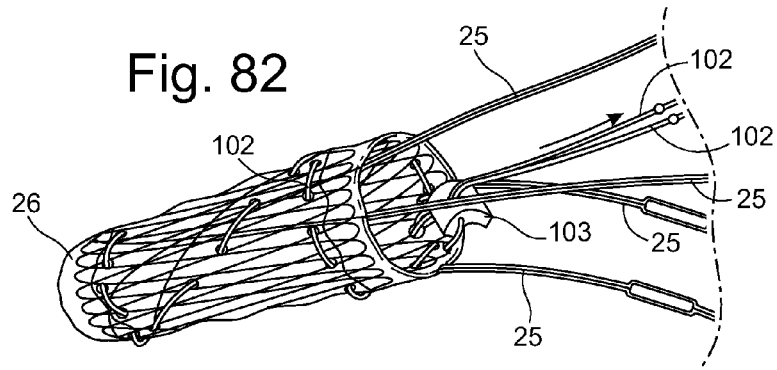
FIG. 82 depicts a perspective view of the pyloric element shown in FIG. 81B, with the constriction element engaged to constrict the pyloric element.

The constriction member 102 may also be threaded through a retaining element 103 to aid in maintaining the collapsed position such as a drawstring cord stop or the like. See FIGS. 81A, 81B and 82. This figure shows a stop element that is affixed to the pyloric element 26 and the constriction member is threaded through. For example, this mechanical stop 103 could be a thick sheet of silicone with a slit or small hole punched through the center section, and the retrieval drawstring is pulled through the opening. When the constriction member 102 is pulled, it is drawn through this stop element 103 and the mechanical stop applies resistance to the retrieval drawstring to hold the device 10 in the collapsed state. To further improve the holding capacity of the mechanical stop 103, a feature could be added to the retrieval drawstring 102 such as a knot tied or an arrowhead or bead attached to the drawstring that allows the feature to be pulled through the slit of the mechanical stop 103, but creates a mechanical interference to prevent the drawstring from pulling back through the stop. The mechanical stop could also be a cord stop 103 as shown in 81A.

The foregoing description of the preferred embodiments of the invention has been presented for the purposes of illustration and description. It is not intended to be exhaustive or to limit the invention to the precise form disclosed. Many modifications and variations are possible in light of the above teaching. It is intended that the scope of the invention not be limited by this detailed description, but by the claims and the equivalents to the claims appended hereto.

INDUSTRIAL APPLICABILITY

This invention may be industrially applied to the development, manufacture, and use of bariatric devices for weight loss purposes.

What is claimed is:

1. A bariatric device for placement into a stomach to achieve weight loss, comprising:
   a. a cardiac element, the cardiac element comprising:
      i. a first contact member having a substantially flattened frustoconical shape, the first contact member defining a substantially circular opening adapted to correspond to the cardiac opening of a stomach, the first contact member being constructed of materials flexible enough to be collapsed for placement and expanded for operation; and
      ii. a first wire stiffening member inside the first contact member that can be collapsed for placement and will cause the first contact member to substantially return to and maintain its desired shape in the stomach after the cardiac element is expanded for operation;
   b. a pyloric element, the pyloric element comprising:
      i. a second contact member adapted to engage the pyloric region of the stomach, having a steep frustoconical shape, sized to prevent the pyloric element from passing through the stomach's pyloric valve, the second contact member being constructed of materials flexible enough to be collapsed for placement and expanded for operation; and
      ii. a second wire stiffening member inside the second contact member that can be collapsed for placement and will cause the second contact member to substantially return to and maintain its desired shape in the stomach after the pyloric element is expanded for operation; and
      iii. an opening sized and adapted to allow chyme in the stomach to pass from the stomach through the pyloric valve; and
   c. a connecting element coupled with the pyloric element and the cardiac element, constructed of resilient shape-holding material and shaped so that it causes the cardiac element to at least intermittently contact the upper stomach.

2. The bariatric device of claim 1, wherein the connecting element is constructed to impart an outwardly biasing force against both the pyloric element and cardiac element, and consequently an outwardly biasing force by the pyloric element and cardiac element against the pyloric region of the stomach and the upper stomach, respectively.

3. The bariatric device of claim 2, wherein the device is further equipped with an adjustment element, the adjustment element constructed such that the location or orientation of the cardiac element relative to the pyloric element is adjustable while in the stomach.

4. The bariatric device of claim 2, wherein the device is further equipped with an adjustment element, the adjustment element constructed such that the outwardly biasing force of the cardiac element or pyloric element is adjustable while in the stomach.

5. The bariatric device of claim 1, wherein the connecting element is comprised of a plurality of members.

6. The bariatric device of claim 1, further comprising:
   an inflatable body coupled with the cardiac element, such that when inflated, the inflatable body increases the contact or force between the cardiac element and the upper stomach.

7. The bariatric device of claim 6, wherein the inflatable body is in the deflated shape of a substantially flattened frusto cone or frusto cone section, coupled with the top of the cardiac element.

8. The bariatric device of claim 6, wherein the inflatable body is coupled with an inflation element positioned to allow inflating fluid to be inserted or removed while the bariatric device is in the stomach.

* * * * *